(12) United States Patent
Bertoletti et al.

(10) Patent No.: US 8,603,810 B2
(45) Date of Patent: Dec. 10, 2013

(54) T-CELL HAVING A T-CELL RECEPTOR THAT RECOGNIZES EPITOPE HBC18-27 OF HEPATITIS B VIRAL CORE ANTIGEN

(75) Inventors: Antonio Bertoletti, Singapore (SG); Adam Gehring, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 154 days.

(21) Appl. No.: 12/991,904

(22) PCT Filed: May 7, 2009

(86) PCT No.: PCT/SG2009/000165
§ 371 (c)(1),
(2), (4) Date: Nov. 9, 2010

(87) PCT Pub. No.: WO2009/136874
PCT Pub. Date: Nov. 12, 2009

(65) Prior Publication Data
US 2011/0070208 A1    Mar. 24, 2011

Related U.S. Application Data

(60) Provisional application No. 61/051,974, filed on May 9, 2008.

(51) Int. Cl.
*C12N 5/00* (2006.01)
*A61K 48/00* (2006.01)

(52) U.S. Cl.
USPC ...................................... 435/325; 424/93.21

(58) Field of Classification Search
USPC ...................................... 435/325; 424/93.21
See application file for complete search history.

(56) References Cited

U.S. PATENT DOCUMENTS

| 6,322,789 | B1 * | 11/2001 | Vitiello et al. | 424/189.1 |
| 7,368,118 | B2 | 5/2008 | Chisari | |
| 2005/0232935 | A1 * | 10/2005 | Chisari | 424/189.1 |

FOREIGN PATENT DOCUMENTS

| WO | 2006031221 A1 | | 3/2006 |
| WO | WO2006031221 A2 | * | 3/2006 |
| WO | WO 2007034489 A2 | * | 3/2007 |
| WO | WO 2007/034489 | * | 8/2007 |
| WO | 2008042814 A2 | | 4/2008 |
| WO | WO 2008042814 A2 | * | 4/2008 |

OTHER PUBLICATIONS

Bertoletti (Hepatology, 1997, vol. 26, pp. 1027-1034).*
Chen (Antiviral Research, 2001, vol. 52, pp. 99-111).*
Maini (Eur. J. Immunol. 2000, vol. 30, p. 3067-3078).*
Gehring (J. Hepatology, 2011, vol. 55, p. 103-110).*
Bohne (Gastroenterology, Jan. 2008, vol. 134, pp. 239-247).*
Schumacher (Nature, 2002, vol. 2, pp. 512-519).*
Bohne et al., "T Cells Redirected Against Hepatitis B Virus Surface Proteins Eliminate Infected Hepatocytes," Gastroenterology 134:239-247, 2008.
Chen et al., "Modeling the T-helper cell response in acute and chronic hepatitis B virus infection using T-cell receptor transgenic mice," Antiviral Research 52:99-111, 2001.
Schumacher, "T-Cell Receptor Gene Therapy," Nature Reviews 2:512-519, 2002.
Engels et al., "Retroviral Vectors for High-Level Transgene Expression in T Lymphocytes," *Human Gene Therapy*, 14:1155-1168, 2003.
Gehring et al., "The Level of Viral Antigen Presented by Hepatocytes Influences CD8 T-Cell Function," *Journal of Virology*, 81(6):2940-2949, 2007.
Karlin et al., "Methods for assessing the statistical significance of molecular sequence features by using general scoring schemes," *Proc. Natl. Acad. Sci. USA*, 87:2264-2268, 1990.
Strain et al., "Native and Recombinant Human Hepatocyte Growth Factors are Highly Potent Promoters of DNA Synthesis in both Human and Rat Hepatocytes," *J. Clin. Invest.*, 87:1853-1857, 1991.
Sun et al., "Stable HepG2- and Huh7-based human hepatoma cell lines for efficient regulated expression of infectious hepatitis B virus," *Journal of Hepatology*, 45:636-645, 2006.

* cited by examiner

*Primary Examiner* — Michael C. Wilson
(74) *Attorney, Agent, or Firm* — Seed IP Law Group PLLC

(57) ABSTRACT

There is provided at least one isolated cell comprising at least one HBV epitope-reactive exogenous T cell receptor and/or fragment thereof, and methods for producing them. In particular, there is provided polynucleotides, constructs and vectors encoding at least one HBV epitope-reactive exogenous T cell receptor for use in the treatment of Hepatitis B Virus (HBV) and Hepatocellular Carcinoma (HCC). The invention further provides kits and methods of detection of HBV and HCC.

3 Claims, 12 Drawing Sheets

A

B

A

B

SEQUENCE LISTING

<160> NUMBER OF SEQ ID NOS: 58

<210> SEQ ID NO 1
<211> LENGTH: 21
<212> TYPE: DNA
<213> ORGANISM: Homo sapiens
<220> FEATURE:
<221> NAME/KEY: misc_feature
<223> OTHER INFORMATION: Complementarity Determining Region 1 (CDR1) for
      alpha 3 chain of wild type TCR

<400> SEQUENCE: 1
aaaactagta taaacaattt a                                              21

<210> SEQ ID NO 2
<211> LENGTH: 24
<212> TYPE: DNA
<213> ORGANISM: Homo sapiens
<220> FEATURE:
<221> NAME/KEY: misc_feature
<223> OTHER INFORMATION: Complementarity Determining Region 2 (CDR2) for
      alpha 3 chain of wild type TCR

<400> SEQUENCE: 2
ttaatacgtt caaatgaaag agag                                           24

<210> SEQ ID NO 3
<211> LENGTH: 42
<212> TYPE: DNA
<213> ORGANISM: Homo sapiens
<220> FEATURE:
<221> NAME/KEY: misc_feature
<223> OTHER INFORMATION: Complementarity Determining Region 3 (CDR3) for
      alpha 3 chain of wild type TCR

<400> SEQUENCE: 3
tgtgctacgt ggctctctgg ttctgcaagg caactgacct tt                       42

<210> SEQ ID NO 4
<211> LENGTH: 822
<212> TYPE: DNA
<213> ORGANISM: Homo sapiens
<220> FEATURE:
<221> NAME/KEY: Misc_feature
<223> OTHER INFORMATION: Alpha chain of wild type TCR
<220> FEATURE:
<221> NAME/KEY: Misc_feature
<223> OTHER INFORMATION: Alpha 3 chain of wild type TCR

<400> SEQUENCE: 4
atggaaactc tcctgggagt gtctttggtg attctatggc ttcaactggc tagggtgaac     60
agtcaacagg gagaagagga tcctcaggcc ttgagcatcc aggagggtga aaatgccacc    120
atgaactgca gttacaaaac tagtataaac aatttacagt ggtatagaca aaattcaggt    180
agaggccttg tccacctaat tttaatacgt tcaaatgaaa gagagaaaca cagtggaaga    240
ttaagagtca cgcttgacac ttccaagaaa gcagttcct tgttgatcac ggcttcccgg     300
gcagcagaca ctgcttctta cttctgtgct acgtggctct ctggttctgc aaggcaactg    360
acctttggat ctgggacaca attgactgtt tacctgata tccagaaccc tgaccctgcc     420
gtgtaccagc tgagagactc taaatccagt gacaagtctg tctgcctatt caccgatttt    480
gattctcaaa caaatgtgtc acaaagtaag gattctgatg tgtatatcac agacaaaact    540
gtgctagaca tgaggtctat ggacttcaag agcaacagtg ctgtggcctg gagcaacaaa    600

-continued

```
tctgactttg catgtgcaaa cgccttcaac aacagcatta ttccagaaga caccttcttc    660
cccagcccag aaagttcctg tgatgtcaag ctggtcgaga aaagctttga aacagatacg    720 aacctaaaact ttcaaaacct gtcagtgatt gggttccgaa tcctcctcct gaaagtggcc   780
gggtttaatc tgctcatgac gctgcggctg tggtccagct ga                      822
```

```
<210> SEQ ID NO 5
<211> LENGTH: 21
<212> TYPE: DNA
<213> ORGANISM: Homo sapiens
<220> FEATURE:
<221> NAME/KEY: Misc_feature
<223> OTHER INFORMATION: Complementarity Determining Region 1 (CDR1) for
      alpha 3 chain of optimised TCR

<400> SEQUENCE: 5
aagacatcaa tcaacaactt g                                              21
```

```
<210> SEQ ID NO 6
<211> LENGTH: 24
<212> TYPE: DNA
<213> ORGANISM: Homo sapiens
<220> FEATURE:
<221> NAME/KEY: Misc_feature
<223> OTHER INFORMATION: Complementarity Determining Region 2 (CDR2) for
      alpha 3 chain of optimised TCR

<400> SEQUENCE: 6
ctgattcgga gtaatgagcg ggaa                                           24
```

```
<210> SEQ ID NO 7
<211> LENGTH: 42
<212> TYPE: DNA
<213> ORGANISM: Homo sapiens
<220> FEATURE:
<221> NAME/KEY: Misc_feature
<223> OTHER INFORMATION: Complementarity Determining Region 3 (CDR3) for
      alpha 3 chain of optimised TCR

<400> SEQUENCE: 7
tgtgctacat ggctgagtgg cagcgcacgg caattgactt tt                       42
```

```
<210> SEQ ID NO 8
<211> LENGTH: 822
<212> TYPE: DNA
<213> ORGANISM: Homo sapiens
<220> FEATURE:
<221> NAME/KEY: Misc_feature
<223> OTHER INFORMATION: Alpha 3 chain of optimised TCR

<400> SEQUENCE: 8
atggagaccc ttctgggagt gtccctcgtg attctgtggc tgcagcttgc tcgggtgaat     60
tctcagcagg gcgaggaaga cccgcaggcc cttagcattc aggaagggga gaacgctacc    120
atgaattgct catacaagac atcaatcaac aacttgcagt ggtaccgtca gaactctggg    180
agaggactcg tgcacctgat cctgattcgg agtaatgagc gggaaaaaca ctctggaagg    240
ctgagggtga ccctcgatac tctaaaaaa tcctcctccc tgctgataac cgccagcagg    300
gccgccgaca ccgcttccta cttctgtgct acatggctga gtggcagcgc acggcaattg   360
acttttggga gtggcactca gctgacagtg ctgcccgaca tccagaatcc agatcccgca    420
gtgtatcagc tgagagactc aaagtcaagt gacaagagtg tgtgcctgtt cactgatttt    480
gactctcaga ccaacgtctc tcagtctaag gacagcgacg tttacatcac tgacaaaact    540
gtgctggaca tgcgcagtat ggactttaaa tcaaattccg ccgtggcttg gagcaataag    600
```

```
tctgacttcg cctgtgctaa tgcttttaat aactccatca ttccggagga tacattttc    660 cctagccccg agtcatcctg cgacgtgaag ctggtggaga agtcattcga gaccgacacc    720
aatcttaact ttcagaacct gtccgttatc gggtttagaa tcctgctgct gaaggttgcc    780
ggattcaacc tgcttatgac gttgcgcctg tggtccagct ga                      822
```

<210> SEQ ID NO 9
<211> LENGTH: 7
<212> TYPE: PRT
<213> ORGANISM: Homo sapiens
<220> FEATURE:
<221> NAME/KEY: Misc_feature
<223> OTHER INFORMATION: Complementarity Determining Region 1 (CDR1) for
      alpha 3 chain of TCR

<400> SEQUENCE: 9

Lys Thr Ser Ile Asn Asn Leu
1               5

<210> SEQ ID NO 10
<211> LENGTH: 8
<212> TYPE: PRT
<213> ORGANISM: Homo sapiens
<220> FEATURE:
<221> NAME/KEY: Misc_feature
<223> OTHER INFORMATION: Complementarity Determining Region 2 (CDR2) for
      alpha 3 chain of TCR

<400> SEQUENCE: 10

Leu Ile Arg Ser Asn Glu Arg Glu
1               5

<210> SEQ ID NO 11
<211> LENGTH: 14
<212> TYPE: PRT
<213> ORGANISM: Homo sapiens
<220> FEATURE:
<221> NAME/KEY: Misc_feature
<223> OTHER INFORMATION: Complementarity Determining Region 3 (CDR3) for
      alpha 3 chain of TCR

<400> SEQUENCE: 11

Cys Ala Thr Trp Leu Ser Gly Ser Ala Arg Gln Leu Thr Phe
1               5                   10

<210> SEQ ID NO 12
<211> LENGTH: 273
<212> TYPE: PRT
<213> ORGANISM: Homo sapiens
<220> FEATURE:
<221> NAME/KEY: Misc_feature
<223> OTHER INFORMATION: Alpha 3 chain of TCR

<400> SEQUENCE: 12

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

```
Leu Arg Val Thr Leu Asp Thr Ser Lys Lys Ser Ser Leu Leu Ile
                85                  90                  95

Thr Ala Ser Arg Ala Ala Asp Thr Ala Ser Tyr Phe Cys Ala Thr Trp
        100                 105                 110

Leu Ser Gly Ser Ala Arg Gln Leu Thr Phe Gly Ser Gly Thr Gln Leu
        115                 120                 125

Thr Val Leu Pro Asp Ile Gln Asn Pro Asp Pro Ala Val Tyr Gln Leu
        130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
        180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
        210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
        260                 265                 270

Ser

<210> SEQ ID NO 13
<211> LENGTH: 21
<212> TYPE: DNA
<213> ORGANISM: Homo sapiens
<220> FEATURE:
<221> NAME/KEY: Misc_feature
<223> OTHER INFORMATION: Complementarity Determining Region 1 (CDR1) for
      beta 8 chain of wild type TCR

<400> SEQUENCE: 13
atttcaggac acgactacct t                                              21

<210> SEQ ID NO 14
<211> LENGTH: 24
<212> TYPE: DNA
<213> ORGANISM: Homo sapiens
<220> FEATURE:
<221> NAME/KEY: Misc_feature
<223> OTHER INFORMATION: Complementarity Determining Region 2 (CDR2) for
      beta 8 chain of wild type TCR

<400> SEQUENCE: 14
tactttaaca caacgttcc gata                                            24

<210> SEQ ID NO 15
<211> LENGTH: 45
<212> TYPE: DNA
<213> ORGANISM: Homo sapiens
<220> FEATURE:
<221> NAME/KEY: Misc_feature
<223> OTHER INFORMATION: Complementarity Determining Region 3 (CDR3) for
      beta 8 chain of wild type TCR

<400> SEQUENCE: 15
tgtgccagca gcaatcgggc gagctcctac aatgagcagt tcttc                    45
```

```
<210> SEQ ID NO 16
<211> LENGTH: 942
<212> TYPE: DNA
<213> ORGANISM: Homo sapiens
<220> FEATURE:
<221> NAME/KEY: Misc_feature
<223> OTHER INFORMATION: Beta 8 chain of wild type TCR

<400> SEQUENCE: 16
atggactcct ggaccctctg ctgtgtgtcc ctttgcatcc tggtagcaaa gcacacagat    60
gctggagtta tccaatcacc ccggcacgag gtgacagaga tgggacaaga agtgactctg   120
agatgtaaac caatttcagg acacgactac cttttctggt acagacagac catgatgcgg   180
ggactggagt tgctcattta ctttaacaac aacgttccga tagatgattc agggatgccc   240
gaggatcgat tctcagctaa gatgcctaat gcatcattct ccactctgaa gatccagccc   300
tcagaaccca gggactcagc tgtgtacttc tgtgccagca gcaatcgggc gagctcctac   360
aatgagcagt tcttcgggcc agggacacgg ctcaccgtgc tagaggacct gaaaaacgtg   420
ttcccacccg aggtcgctgt gtttgagcca tcagaagcag agatctccca cacccaaaag   480
gccacactgg tgtgcctggc cacaggcttc taccccgacc acgtggagct gagctggtgg   540
gtgaatggga aggaggtgca cagtggggtc agcacagacc cgcagcccct caaggagcag   600
cccgccctca tgactccag atactgcctg agcagccgcc tgagggtctc ggccaccttc   660
tggcagaacc ccgcaacca cttccgctgt caagtccagt tctacgggct ctcggagaat   720
gacgagtgga cccaggatag ggccaaacct gtcacccaga tcgtcagcgc cgaggcctgg   780
ggtagagcag actgtggctt cacctccgag tcttaccagc aaggggtcct gtctgccacc   840
atcctctatg agatcttgct agggaaggcc accttgtatg ccgtgctggt cagtgccctc   900
gtgctgatgg ccatggtcaa gagaaaggat tccagaggct ag                      942

<210> SEQ ID NO 17
<211> LENGTH: 21
<212> TYPE: DNA
<213> ORGANISM: Homo sapiens
<220> FEATURE:
<221> NAME/KEY: Misc_feature
<223> OTHER INFORMATION: Complementarity Determining Region 1 (CDR1) for
      beta 8 chain of optimised TCR

<400> SEQUENCE: 17
atctctgggc acgactacct g                                              21

<210> SEQ ID NO 18
<211> LENGTH: 24
<212> TYPE: DNA
<213> ORGANISM: Homo sapiens
<220> FEATURE:
<221> NAME/KEY: Misc_feature
<223> OTHER INFORMATION: Complementarity Determining Region 2 (CDR2) for
      beta 8 chain of optimised TCR

<400> SEQUENCE: 18
tattttaata caatgtgcc tatc                                            24

<210> SEQ ID NO 19
<211> LENGTH: 45
<212> TYPE: DNA
<213> ORGANISM: Homo sapiens
<220> FEATURE:
<221> NAME/KEY: Misc_feature
<223> OTHER INFORMATION: Complementarity Determining Region 3 (CDR3) for
      beta 8 chain of optimised TCR
```

```
<400> SEQUENCE: 19
tgtgcctcct ccaaccgggc ctcctcttat aacgagcagt tcttc                      45

<210> SEQ ID NO 20
<211> LENGTH: 942
<212> TYPE: DNA
<213> ORGANISM: Homo sapiens
<220> FEATURE:
<221> NAME/KEY: Misc_feature
<223> OTHER INFORMATION: Beta 8 chain of optimised TCR

<400> SEQUENCE: 20
atggacagct ggacactgtg ctgcgtgagc ctgtgcattc tggtggccaa gcacaccgac       60
gccggcgtga tccagagccc tcgccacgag gtgaccgaaa tgggccagga ggtgacactg      120
cgctgcaagc caatctctgg gcacgactac ctgttctggt acaggcagac catgatgagg      180
ggcctggaac tgctgatcta tttaataac aatgtgccta tcgatgactc tggcatgccc       240
gaggacaggt tctccgccaa gatgcccaac gccagcttct ccaccctgaa gatccagccc      300
tccgaaccta gggactccgc cgtgtacttc tgtgcctcct ccaaccgggc ctcctcttat      360
aacgagcagt tcttcggccc tggaacccgc ctgaccgtgc tggaggacct gaaaaatgtg      420
tttccccccg aggtggccgt gtttgaacca agcgaggccg agatcagcca cacacagaag      480
gccaccctgg tgtgtctggc caccggattc tatcccgatc acgtggagct gagctggtgg      540
gtgaacggga aggaggtgca ctctggcgtg agcaccgacc ctcagccact gaaagagcag      600
cccgccctga atgattctcg gtactgcctg tccagccgcc tgcgcgtgtc tgccaccttc      660
tggcagaacc cagaaatca cttcaggtgc caggtgcagt tctatgggct gagcgagaac      720
gacgaatgga cccaggacag agccaagcct gtgacacaga tcgtgtctgc cgaagcctgg      780
ggcagagccg actgcggctt taccagcgag agctaccagc agggcgtgct gtccgccaca      840
attctgtacg agatcctgct gggaaaggcc acactgtacg ccgtgctggt gagcgccctg      900
gtgctgatgg ccatggtgaa gcggaaagac tcccggggct ga                        942

<210> SEQ ID NO 21
<211> LENGTH: 7
<212> TYPE: PRT
<213> ORGANISM: Homo sapiens
<220> FEATURE:
<221> NAME/KEY: Misc_feature
<223> OTHER INFORMATION: Complementarity Determining Region 1 (CDR1) for
      beta 8 chain of TCR

<400> SEQUENCE: 21

Ile Ser Gly His Asp Tyr Leu
1               5

<210> SEQ ID NO 22
<211> LENGTH: 8
<212> TYPE: PRT
<213> ORGANISM: Homo sapiens
<220> FEATURE:
<221> NAME/KEY: Misc_feature
<223> OTHER INFORMATION: Complementarity Determining Region 2 (CDR2) for
      beta 8 chain of TCR

<400> SEQUENCE: 22

Tyr Phe Asn Asn Asn Val Pro Ile
1               5

<210> SEQ ID NO 23
```

```
<211> LENGTH: 15
<212> TYPE: PRT
<213> ORGANISM: Homo sapiens
<220> FEATURE:
<221> NAME/KEY: Misc_feature
<223> OTHER INFORMATION: Complementarity Determining Region 3 (CDR3) for
      beta 8 chain of TCR

<400> SEQUENCE: 23

Cys Ala Ser Ser Asn Arg Ala Ser Ser Tyr Asn Glu Gln Phe Phe
1               5                   10                  15

<210> SEQ ID NO 24
<211> LENGTH: 313
<212> TYPE: PRT
<213> ORGANISM: Homo sapiens
<220> FEATURE:
<221> NAME/KEY: Misc_feature
<223> OTHER INFORMATION: Beta 8 chain of TCR

<400> SEQUENCE: 24

Met Asp Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Asn Arg Ala Ser Ser Tyr Asn Glu Gln Phe Phe Gly Pro Gly
        115                 120                 125

Thr Arg Leu Thr Val Leu Glu Asp Leu Lys Asn Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300
```

```
Met Val Lys Arg Lys Asp Ser Arg Gly
305                 310

<210> SEQ ID NO 25
<211> LENGTH: 10
<212> TYPE: PRT
<213> ORGANISM: Hepatitis B virus
<220> FEATURE:
<221> NAME/KEY: Misc_feature
<223> OTHER INFORMATION: HBc18-27 epitope (Genotype A/D/E/F); (WT
      C18-27)

<400> SEQUENCE: 25

Phe Leu Pro Ser Asp Phe Phe Pro Ser Val
1               5                   10

<210> SEQ ID NO 26
<211> LENGTH: 10
<212> TYPE: PRT
<213> ORGANISM: Hepatitis B virus
<220> FEATURE:
<221> NAME/KEY: Misc_feature
<223> OTHER INFORMATION: HBc18-27 epitope (Genotype B/C); 27I

<400> SEQUENCE: 26

Phe Leu Pro Ser Asp Phe Phe Pro Ser Ile
1               5                   10

<210> SEQ ID NO 27
<211> LENGTH: 10
<212> TYPE: PRT
<213> ORGANISM: Hepatitis B virus
<220> FEATURE:
<221> NAME/KEY: Misc_feature
<223> OTHER INFORMATION: Natural Variant 1 of HBc18-27 epitope

<400> SEQUENCE: 27

Phe Leu Pro Asn Asp Phe Phe Pro Ser Val
1               5                   10

<210> SEQ ID NO 28
<211> LENGTH: 10
<212> TYPE: PRT
<213> ORGANISM: Hepatitis B virus
<220> FEATURE:
<221> NAME/KEY: Misc_feature
<223> OTHER INFORMATION: Natural Variant 2 of HBc18-27 epitope

<400> SEQUENCE: 28

Phe Leu Pro Asn Asp Phe Phe Pro Ser Ala
1               5                   10

<210> SEQ ID NO 29
<211> LENGTH: 10
<212> TYPE: PRT
<213> ORGANISM: Hepatitis B virus
<220> FEATURE:
<221> NAME/KEY: Misc_feature
<223> OTHER INFORMATION: Natural Variant 3 of HBc18-27 epitope

<400> SEQUENCE: 29

Phe Leu Pro Ala Asp Phe Phe Pro Ser Ile
1               5                   10

<210> SEQ ID NO 30
<211> LENGTH: 10
<212> TYPE: PRT
<213> ORGANISM: Hepatitis B virus
```

-continued

<220> FEATURE:
<221> NAME/KEY: Misc_feature
<223> OTHER INFORMATION: Natural Variant 4 of HBc18-27 epitope

<400> SEQUENCE: 30

Phe Leu Pro Val Asp Phe Phe Pro Ser Ile
1               5                   10

<210> SEQ ID NO 31
<211> LENGTH: 10
<212> TYPE: PRT
<213> ORGANISM: Hepatitis B virus
<220> FEATURE:
<221> NAME/KEY: Misc_feature
<223> OTHER INFORMATION: Natural Variant 5 of HBc18-27 epitope

<400> SEQUENCE: 31

Phe Leu Pro Thr Asp Tyr Phe Pro Ser Val
1               5                   10

<210> SEQ ID NO 32
<211> LENGTH: 10
<212> TYPE: PRT
<213> ORGANISM: Hepatitis B virus
<220> FEATURE:
<221> NAME/KEY: Misc_feature
<223> OTHER INFORMATION: Natural Variant 6 of HBc18-27 epitope

<400> SEQUENCE: 32

Phe Leu Pro Ser Asp Phe Tyr Pro Pro Val
1               5                   10

<210> SEQ ID NO 33
<211> LENGTH: 10
<212> TYPE: PRT
<213> ORGANISM: Hepatitis B virus
<220> FEATURE:
<221> NAME/KEY: Misc_feature
<223> OTHER INFORMATION: Natural Variant 7 of HBc18-27 epitope; 26G

<400> SEQUENCE: 33

Phe Leu Pro Ser Asp Phe Phe Pro Gly Val
1               5                   10

<210> SEQ ID NO 34
<211> LENGTH: 10
<212> TYPE: PRT
<213> ORGANISM: Hepatitis B virus
<220> FEATURE:
<221> NAME/KEY: Misc_feature
<223> OTHER INFORMATION: Natural Variant 8 of HBc18-27 epitope; 25M, 26G

<400> SEQUENCE: 34

Phe Leu Pro Ser Asp Phe Phe Met Gly Val
1               5                   10

<210> SEQ ID NO 35
<211> LENGTH: 10
<212> TYPE: PRT
<213> ORGANISM: Hepatitis B virus
<220> FEATURE:
<221> NAME/KEY: Misc_feature
<223> OTHER INFORMATION: Natural Variant 9 of HBc18-27 epitope; 23Y

<400> SEQUENCE: 35

Phe Leu Pro Ser Asp Tyr Phe Pro Ser Val
1               5                   10

```
<210> SEQ ID NO 36
<211> LENGTH: 10
<212> TYPE: PRT
<213> ORGANISM: Hepatitis B virus
<220> FEATURE:
<221> NAME/KEY: Misc_feature
<223> OTHER INFORMATION: Natural Variant 10 of HBc18-27 epitope; 24L

<400> SEQUENCE: 36

Phe Leu Pro Ser Asp Phe Leu Pro Ser Val
1               5                   10

<210> SEQ ID NO 37
<211> LENGTH: 10
<212> TYPE: PRT
<213> ORGANISM: Hepatitis B virus
<220> FEATURE:
<221> NAME/KEY: Misc_feature
<223> OTHER INFORMATION: Natural Variant 11 of HBc18-27 epitope; 21P

<400> SEQUENCE: 37

Phe Leu Pro Pro Asp Phe Phe Pro Ser Val
1               5                   10

<210> SEQ ID NO 38
<211> LENGTH: 10
<212> TYPE: PRT
<213> ORGANISM: Hepatitis B virus
<220> FEATURE:
<221> NAME/KEY: Misc_feature
<223> OTHER INFORMATION: Natural Variant 12 of HBc18-27 epitope; 27A

<400> SEQUENCE: 38

Phe Leu Pro Ser Asp Phe Phe Pro Ser Ala
1               5                   10

<210> SEQ ID NO 39
<211> LENGTH: 10
<212> TYPE: PRT
<213> ORGANISM: Hepatitis B virus
<220> FEATURE:
<221> NAME/KEY: Misc_feature
<223> OTHER INFORMATION: Natural Variant 13 of HBc18-27 epitope; 24Y

<400> SEQUENCE: 39

Phe Leu Pro Ser Asp Phe Tyr Pro Ser Val
1               5                   10

<210> SEQ ID NO 40
<211> LENGTH: 18
<212> TYPE: DNA
<213> ORGANISM: Homo sapiens
<220> FEATURE:
<221> NAME/KEY: Misc_feature
<223> OTHER INFORMATION: Complementarity Determining Region 1 (CDR1) for
      alpha 12 chain of wild type TCR

<400> SEQUENCE: 40
gaccgaggtt cccagtcc                                                 18

<210> SEQ ID NO 41
<211> LENGTH: 15
<212> TYPE: DNA
<213> ORGANISM: Homo sapiens
<220> FEATURE:
<221> NAME/KEY: Misc_feature
<223> OTHER INFORMATION: Complementarity Determining Region 2 (CDR2) for
      alpha 12 chain of wild type TCR

<400> SEQUENCE: 41
```

```
<210> SEQ ID NO 42
<211> LENGTH: 39
<212> TYPE: DNA
<213> ORGANISM: Homo sapiens
<220> FEATURE:
<221> NAME/KEY: Misc_feature
<223> OTHER INFORMATION: Complementarity Determining Region 3 (CDR3) for
      alpha 12 chain of wild type TCR

<400> SEQUENCE: 42
tgtgccgtga acctctatgc aggcaacatg ctcaccttt                            39

<210> SEQ ID NO 43
<211> LENGTH: 825
<212> TYPE: DNA
<213> ORGANISM: Homo sapiens
<220> FEATURE:
<221> NAME/KEY: Misc_feature
<223> OTHER INFORMATION: Alpha 12 chain of wild type TCR

<400> SEQUENCE: 43
atgatgaaat ccttgagagt tttactagtg atcctgtggc ttcagttgag ctgggtttgg     60
agccaacaga aggaggtgga gcagaattct ggacccctca gtgttccaga gggagccatt    120
gcctctctca actgcactta cagtgaccga ggttcccagt ccttcttctg gtacagacaa    180
tattctggga aaagccctga gttgataatg ttcatatact ccaatggtga caaagaagat    240
ggaaggttta cagcacagct caataaagcc agccagtatg tttctctgct catcagagac    300
tcccagccca gtgattcagc cacctacctc tgtgccgtga acctctatgc aggcaacatg    360 ctcaccttg gagggggaac aaggttaatg gtcaaacccc atatccagaa ccctgaccct    420
gccgtgtacc agctgagaga ctctaaatcc agtgacaagt ctgtctgcct attcaccgat    480
tttgattctc aaacaaatgt gtcacaaagt aaggattctg atgtgtatat cacagacaaa    540
actgtgctag acatgaggtc tatggacttc aagagcaaca gtgctgtggc ctggagcaac    600
aaatctgact tgcatgtgc aaacgccttc aacaacagca ttattccaga agacaccttc    660
ttccccagcc cagaaagttc ctgtgatgtc aagctggtcg agaaaagctt tgaaacagat    720
acgaacctaa actttcaaaa cctgtcagtg attgggttcc gaatcctcct cctgaaagtg    780
gccgggttta atctgctcat gacgctgcgg ctgtggtcca gctga                   825

<210> SEQ ID NO 44
<211> LENGTH: 6
<212> TYPE: PRT
<213> ORGANISM: Homo sapiens
<220> FEATURE:
<221> NAME/KEY: Misc_feature
<223> OTHER INFORMATION: Complementarity Determining Region 1 (CDR1) for
      alpha 12 chain of TCR

<400> SEQUENCE: 44

Asp Arg Gly Ser Gln Ser
1               5

<210> SEQ ID NO 45
<211> LENGTH: 5
<212> TYPE: PRT
<213> ORGANISM: Homo sapiens
<220> FEATURE:
<221> NAME/KEY: Misc_feature
<223> OTHER INFORMATION: Complementarity Determining Region 2 (CDR2) for
      alpha 12 chain of TCR
```

<400> SEQUENCE: 45

Ile Tyr Ser Asn Gly
1               5

<210> SEQ ID NO 46
<211> LENGTH: 13
<212> TYPE: PRT
<213> ORGANISM: Homo sapiens
<220> FEATURE:
<221> NAME/KEY: Misc_feature
<223> OTHER INFORMATION: Complementarity Determining Region 3 (CDR3) for
      alpha 12 chain of TCR

<400> SEQUENCE: 46

Cys Ala Val Asn Leu Tyr Ala Gly Asn Met Leu Thr Phe
1               5                   10

<210> SEQ ID NO 47
<211> LENGTH: 274
<212> TYPE: PRT
<213> ORGANISM: Homo sapiens
<220> FEATURE:
<221> NAME/KEY: Misc_feature
<223> OTHER INFORMATION: Alpha 12 chain of TCR

<400> SEQUENCE: 47

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Phe Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Asn Leu Tyr Ala Gly Asn Met Leu Thr Phe Gly Gly Gly Thr Arg
        115                 120                 125

Leu Met Val Lys Pro His Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
          260                 265                 270

Ser Ser

<210> SEQ ID NO 48
<211> LENGTH: 15
<212> TYPE: DNA
<213> ORGANISM: Homo sapiens
<220> FEATURE:
<221> NAME/KEY: Misc_feature
<223> OTHER INFORMATION: Complementarity Determining Region 1 (CDR1) for
      beta 7.8 chain of wild type TCR

<400> SEQUENCE: 48
tcgggtcatg tatcc                                                     15

<210> SEQ ID NO 49
<211> LENGTH: 18
<212> TYPE: DNA
<213> ORGANISM: Homo sapiens
<220> FEATURE:
<221> NAME/KEY: Misc_feature
<223> OTHER INFORMATION: Complementarity Determining Region 2 (CDR2) for
      beta 7.8 chain of wild type TCR

<400> SEQUENCE: 49
ttccagaatg aagctcaa                                                  18

<210> SEQ ID NO 50
<211> LENGTH: 42
<212> TYPE: DNA
<213> ORGANISM: Homo sapiens
<220> FEATURE:
<221> NAME/KEY: Misc_feature
<223> OTHER INFORMATION: Complementarity Determining Region 3 (CDR3) for
      beta 7.8 chain of wild type TCR

<400> SEQUENCE: 50
tgtgccagca gctcggactt tggcaatcag ccccagcatt tt                       42

<210> SEQ ID NO 51
<211> LENGTH: 933
<212> TYPE: DNA
<213> ORGANISM: Homo sapiens
<220> FEATURE:
<221> NAME/KEY: Misc_feature
<223> OTHER INFORMATION: Beta 7.8 chain of wild type TCR

<400> SEQUENCE: 51
atgggcacca ggctcctctg ctgggtggtc ctgggtttcc tagggacaga tcacacaggt     60
gctggagtct cccagtcccc taggtacaaa gtcgcaaaga gaggacagga tgtagctctc    120
aggtgtgatc caatttcggg tcatgtatcc ctttttggt accaacaggc cctggggcag     180
gggccagagt ttctgactta tttccagaat gaagctcaac tagacaaatc ggggctgccc    240
agtgatcgct tctttgcaga aaggcctgag ggatccgtct ccactctgaa gatccagcgc    300
acacagcagg aggactccgc cgtgtatctc tgtgccagca gctcggactt tggcaatcag    360
ccccagcatt ttggtgatgg gactcgactc tccatcctag aggacctgaa caaggtgttc    420
ccacccgagg tcgctgtgtt tgagccatca gaagcagaga tctcccacac ccaaaaggcc    480
acactggtgt gcctggccac aggcttcttc cctgaccacg tggagctgag ctggtgggtg    540
aatgggaagg aggtgcacag tggggtcagc acggacccgc agcccctcaa ggagcagccc    600
gccctcaatg actccagata ctgcctgagc agccgcctga gggtctcggc caccttctgg    660

```
cagaaccccc gcaaccactt ccgctgtcaa gtccagttct acgggctctc ggagaatgac    720
gagtggaccc aggatagggc caaacccgtc acccagatcg tcagcgccga ggcctggggt    780
agagcagact gtggctttac ctcggtgtcc taccagcaag gggtcctgtc tgccaccatc    840
ctctatgaga tcctgctagg gaaggccacc ctgtatgctg tgctggtcag cgcccttgtg    900
ttgatggcca tggtcaagag aaaggatttc tga                                 933
```

<210> SEQ ID NO 52
<211> LENGTH: 5
<212> TYPE: PRT
<213> ORGANISM: Homo sapiens
<220> FEATURE:
<221> NAME/KEY: Misc_feature
<223> OTHER INFORMATION: Complementarity Determining Region 1 (CDR1) for
      beta 7.8 chain of TCR

<400> SEQUENCE: 52

Ser Gly His Val Ser
1               5

<210> SEQ ID NO 53
<211> LENGTH: 6
<212> TYPE: PRT
<213> ORGANISM: Homo sapiens
<220> FEATURE:
<221> NAME/KEY: Misc_feature
<223> OTHER INFORMATION: Complementarity Determining Region 2 (CDR2) for
      beta 7.8 chain of TCR

<400> SEQUENCE: 53

Phe Gln Asn Glu Ala Gln
1               5

<210> SEQ ID NO 54
<211> LENGTH: 14
<212> TYPE: PRT
<213> ORGANISM: Homo sapiens
<220> FEATURE:
<221> NAME/KEY: Misc_feature
<223> OTHER INFORMATION: Complementarity Determining Region 3 (CDR3) for
      beta 7.8 chain of TCR

<400> SEQUENCE: 54

Cys Ala Ser Ser Ser Asp Phe Gly Asn Gln Pro Gln His Phe
1               5                   10

<210> SEQ ID NO 55
<211> LENGTH: 310
<212> TYPE: PRT
<213> ORGANISM: Homo sapiens
<220> FEATURE:
<221> NAME/KEY: Misc_feature
<223> OTHER INFORMATION: Beta 7.8 chain of TCR

<400> SEQUENCE: 55

Met Gly Thr Arg Leu Leu Cys Trp Val Val Leu Gly Phe Leu Gly Thr
1               5                   10                  15

Asp His Thr Gly Ala Gly Val Ser Gln Ser Pro Arg Tyr Lys Val Ala
                20                  25                  30

Lys Arg Gly Gln Asp Val Ala Leu Arg Cys Asp Pro Ile Ser Gly His
            35                  40                  45

Val Ser Leu Phe Trp Tyr Gln Gln Ala Leu Gly Gln Gly Pro Glu Phe
        50                  55                  60

Leu Thr Tyr Phe Gln Asn Glu Ala Gln Leu Asp Lys Ser Gly Leu Pro
65                  70                  75                  80

```
Ser Asp Arg Phe Phe Ala Glu Arg Pro Glu Gly Ser Val Ser Thr Leu
            85                  90                  95

Lys Ile Gln Arg Thr Gln Gln Glu Asp Ser Ala Val Tyr Leu Cys Ala
        100                 105                 110

Ser Ser Ser Asp Phe Gly Asn Gln Pro Gln His Phe Gly Asp Gly Thr
            115                 120                 125

Arg Leu Ser Ile Leu Glu Asp Leu Asn Lys Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Phe
305                 310

<210> SEQ ID NO 56
<211> LENGTH: 10
<212> TYPE: PRT
<213> ORGANISM: Hepatitis B virus
<220> FEATURE:
<221> NAME/KEY: Misc_feature
<223> OTHER INFORMATION: HBe370-79 epitope (Genotype A/D)

<400> SEQUENCE: 56

Ser Ile Val Ser Pro Phe Ile Pro Leu Leu
1               5                   10

<210> SEQ ID NO 57
<211> LENGTH: 10
<212> TYPE: PRT
<213> ORGANISM: Hepatitis B virus
<220> FEATURE:
<221> NAME/KEY: Misc_feature
<223> OTHER INFORMATION: HBc18-27 epitope (Genotype B)
<220> FEATURE:
<221> NAME/KEY: Misc_feature
<223> OTHER INFORMATION: HBe370-79 epitope (Genotype B)

<400> SEQUENCE: 57

Asn Ile Leu Ser Pro Phe Met Pro Leu Leu
1               5                   10

<210> SEQ ID NO 58
<211> LENGTH: 10
```

-continued

```
<212> TYPE: PRT
<213> ORGANISM: Hepatitis B virus
<220> FEATURE:
<221> NAME/KEY: Misc_feature
<223> OTHER INFORMATION: HBe370-79 epitope (Genotype C)

<400> SEQUENCE: 58

Asn Ile Leu Asn Pro Phe Leu Pro Leu Leu
1               5                   10
```

T-CELL HAVING A T-CELL RECEPTOR THAT RECOGNIZES EPITOPE HBC18-27 OF HEPATITIS B VIRAL CORE ANTIGEN

STATEMENT REGARDING SEQUENCE LISTING

The Sequence Listing associated with this application is provided in text format in lieu of a paper copy, and is hereby incorporated by reference into the specification. The name of the text file containing the Sequence Listing is 100125_404USPC_SEQUENCE_LISTING.txt. The text file is 31 KB, was created on Nov. 9, 2010, and is being submitted electronically via EFS-Web.

FIELD OF THE INVENTION

The present invention relates generally to the field of immune mediated therapies for treatment of Hepatitis B Virus (HBV) and HBV-related diseases such as cirrhosis and Hepatocellular carcinoma (HCC) and to methods of preparing these therapies. In particular, the immune mediated therapies may be in the form of cells expressing at least one HBV epitope-reactive exogenous T cell receptor and/or polynucleotides, vectors and/or polypeptides encoding the HBV epitope-reactive T cell receptor.

BACKGROUND OF THE ART

Hepatitis B virus (HBV) infects the liver of hominoidae, including humans, and causes an inflammation called hepatitis. It is a DNA virus and one of many unrelated viruses that cause viral hepatitis. HBV currently infects at least 350 million people worldwide. 75% of chronically infected HBV patients are living in Asia but the virus has a world-wide diffusion. For example, in the United States, approximately 1.5 million Americans, or about 0.5% of the population have HBV. The infection is especially more common in certain risk groups like men who have sex with other men, renal dialysis patients and persons with haemophilia. Chronic HBV infections affects 10 to 15% of first generation Asian Americans and approximately 5% of children adopted from Russia, Asia and Eastern Europe have chronic HBV infections. Chronic HBV infections may eventually lead to liver cirrhosis and Hepatocellular carcinoma (HCC), a fatal disease with very poor response to current chemotherapy.

Currently available methods of treatment for this global large reservoir of chronically infected subjects are challenging as existing drugs suppress but do not eliminate HBV. Though majority of HBV infected patients respond to currently available methods of treatment showing improvements in liver histology and serum Alanine transaminase (ALT) levels, almost all patients relapse when treatment is stopped. Furthermore, the more common methods of treatment of HBV involve the use of drugs such as lamivudine and adefovir. These drugs however, result in development of antiviral resistance in the patients, which occur in approximately 20% of patients treated with lamivudine and in about 3% of those treated with adefovir each year. Ultimately a large proportion of patients would develop resistance, at which point, the anti-viral drugs would have little effect.

There is thus a global need for an effective method of anti-viral therapy that results in an HBV specific immune response to efficiently and successfully eliminate the covalently closed circular form of HBV in a patient. Naturally occurring HBV-epitope specific T cells found in some subjects, lead to the subjects having an efficient and innate control of the HBV infection. Past studies have shown that patients with persistent/chronic HBV infection have their HBV-epitope specific T cells deleted or functionally altered. Therefore, increased knowledge of virus-host interactions during HBV infection has prompted speculation that therapeutic restoration of the defective anti-viral immunity present in patients with chronic infection could possibly lead to disease resolution. The validity of this concept was directly demonstrated in patients with chronic HBV infection who underwent bone marrow transplantation and received marrows from donors with natural immunity to HBV. Infusion of a healthy HBV-primed immune system led to resolution of chronic HBV infection in these patients. However, bone marrow transplantation is clearly not an easy therapeutic option for chronically HBV infected patients and attempts to boost HBV-specific immunity using various vaccines in patients with chronic hepatitis B have been disappointing.

A potential cause of failure of the therapeutic vaccine strategy is the fact that the immune system of HBV chronic carriers does not have the same efficiency and repertoire of specificities as that of healthy non-HBV infected subjects. Further, persistent high production of viral antigens in chronic HBV infected patients can delete or tolerize antigen-specific T cells. Chronic HBV infected patients are thus characterized by low/absent HBV-specific CD4+ and CD8+ T cell responses. Moreover, it has been speculated that both low T cell avidity and an ineffective cytokine profile generated in response to HBV infection may contribute to the development of chronic HBV infection rather than viral clearance.

Clearly, more effective therapies targeting molecules involved in the cytokine profile of HBV infected patients are necessary in order to reduce the worldwide morbidity and mortality from HBV infection and HBV-related malignancies.

SUMMARY OF THE INVENTION

The present invention addresses the problems above, and in particular provides a novel, efficient and effective method of treating HBV infection by redirecting the specificity of lymphocytes of chronic HBV infected patients using exogenous T cell receptor (TCR) transfer.

According to a first aspect, the present invention provides at least one isolated cell comprising at least one HBV epitope-reactive exogenous T cell receptor (TCR) and/or fragment thereof.

In particular, the HBV epitope may be HLA-A2 restricted. More in particular, the HBV epitope may comprise at least one hepatitis B core antigen or one hepatitis B envelope antigen, or a mutant thereof. Even more in particular, the HBV epitope may comprise HBc18-27, HBs370-79 and/or a mutant thereof. The HBc18-27 epitope may comprise at least one sequence selected from the group consisting of SEQ ID NOs:25 to 39. In particular, the HBc18-27 epitope may comprise sequence, SEQ ID NO:25. The HBs370-79 epitope may comprise at least one sequence selected from the group consisting of SEQ ID NO:56 to 58. In particular, the HBs370-79 epitope may comprise sequence SEQ ID NO:56.

In particular, the cell according to the present invention may further comprise at least one second HBV epitope-reactive exogenous TCR and/or fragment thereof, wherein the second HBV epitope may be different from the first HBV epitope. In particular, the first HBV epitope may be HBc18-27 and the second epitope may be HBs370-79.

The exogenous TCR may comprise at least one α-chain comprising at least one amino acid sequence selected from the group consisting of SEQ ID NO:9, SEQ ID NO:10 and SEQ ID NO:11 or mutants thereof. In particular, the exogenous TCR comprises at least one α-chain comprising the sequences SEQ ID NO:9, SEQ ID NO:10 and SEQ ID NO:11. The exogenous TCR may comprise at least one β-chain comprising at least one amino acid sequence selected from the group consisting of SEQ ID NO:21, SEQ ID NO:22 and SEQ ID NO:23 or mutants thereof. More in particular, the exogenous TCR may comprise at least one β-chain comprising the sequences SEQ ID NO:21, SEQ ID NO:22 and SEQ ID NO:23. All sequences are shown in Tables 1 and 2.

In particular, the exogenous TCR may comprise at least one α-chain having at least 80% amino acid identity to SEQ ID NO:12 or a fragment thereof and/or at least one β-chain having at least 80% amino acid identity to SEQ ID NO:24 or a fragment thereof. More in particular, the exogenous TCR may comprise at least one α-chain of SEQ ID NO:12 and/or at least one β-chain of SEQ ID NO:24.

The exogenous TCR may comprise at least one α-chain comprising at least one amino acid sequence selected from the group consisting SEQ ID NO:44, SEQ ID NO:45 and SEQ ID NO:46 or mutants thereof. In particular, the exogenous TCR comprises at least one α-chain comprising the sequences SEQ ID NO:44, SEQ ID NO:45 and SEQ ID NO:46. The exogenous TCR may comprise at least one β-chain comprising at least one amino acid sequence selected from the group consisting of SEQ ID NO:52, SEQ ID NO:53 and SEQ ID NO:54 or mutants thereof. More in particular, the exogenous TCR may comprise at least one β-chain comprising the sequences SEQ ID NO:52, SEQ ID NO:53 and SEQ ID NO:54. All sequences are shown in Tables 1 and 2.

In particular, the exogenous TCR may comprise at least one α-chain having at least 80% amino acid identity to SEQ ID NO:47 or a fragment thereof and/or at least one β-chain having at least 80% amino acid identity to SEQ ID NO:55 or a fragment thereof. More in particular, the exogenous TCR may comprise at least one α-chain of SEQ ID NO:47 and/or at least one β-chain of SEQ ID NO:55.

In particular, the cell according to the present invention may be at least one hematopoietic stem cell. More in particular, the cell may be at least one Peripheral Blood Lymphocytes (PBL)-derived T cell.

According to another aspect, the present invention provides at least one isolated polynucleotide comprising at least one sequence encoding at least one α-chain and/or at least one sequence encoding at least one β-chain wherein, the α-chain and β-chain may be part of at least one exogenous HBV epitope-reactive TCR. The HBV epitope may be HBc18-27 and/or HBs370-79.

In particular, the sequence encoding the α-chain comprises at least one sequence selected from SEQ ID NO:1 and SEQ ID NO:5, at least one sequence selected from SEQ ID NO:2 and SEQ ID NO:6 and at least one sequence selected from SEQ ID NO:3 and SEQ ID NO:7 and/or the sequence encoding the β-chain comprises at least one sequence selected from SEQ ID NO:13 and SEQ ID NO:17, at least one sequence selected from SEQ ID NO:14 and SEQ ID NO:18 and at least one sequence selected from SEQ ID NO:15 and SEQ ID NO:19. More in particular, the sequence encoding the α-chain may comprise SEQ ID NO:5, SEQ ID NO:6 and SEQ ID NO:7 and/or the sequence encoding the β-chain may comprise SEQ ID NO:17, SEQ ID NO:18 and SEQ ID NO:19.

In particular, the α-chain of the HBV epitope-reactive exogenous TCR may have at least 80% sequence identity to SEQ ID NO:4 or SEQ ID NO:8 and/or the β-chain of the HBV epitope-reactive exogenous TCR may have at least 80% sequence identity to SEQ ID NO:16 or SEQ ID NO:20. More in particular, the sequence encoding the α-chain may be selected from the group consisting of SEQ ID NO:4 and SEQ ID NO:8, and/or the sequence encoding the β-chain may be selected from the group consisting of SEQ ID NO:16 and SEQ ID NO:20. More in particular, the sequence of the α-chain of the HBc18-27 epitope reactive exogenous TCR may be selected from the group consisting of SEQ ID NO:4 and SEQ ID NO:8, and/or the sequence of the β-chain of the HBc18-27 epitope reactive exogenous TCR may be selected from the group consisting of SEQ ID NO:16 and SEQ ID NO:20.

In particular, the sequence encoding the α-chain comprises SEQ ID NO:40, SEQ ID NO:41 and SEQ ID NO:42 and/or the sequence encoding the β-chain comprises SEQ ID NO:48, SEQ ID NO:49, and SEQ ID NO:50. More in particular, the α-chain of the HBV epitope-reactive exogenous TCR may have at least 80% sequence identity to SEQ ID NO:43 and the β-chain of the HBV epitope-reactive exogenous T cell receptor has at least 80% sequence identity to SEQ ID NO:51. Even more in particular, the sequence encoding the α-chain comprises SEQ ID NO:43, and/or the sequence encoding the β-chain comprises SEQ ID NO:51. More in particular, the sequence of the α-chain of the HBs370-79 epitope reactive exogenous TCR may comprise SEQ ID NO:43 and/or the sequence of the β-chain of the HBs370-79 epitope reactive exogenous TCR may comprise SEQ ID NO:51.

According to another aspect, the present invention provides at least one isolated polypeptide encoded by at least one polynucleotide of the present invention.

According to still another aspect, the present invention provides at least one isolated polypeptide comprising at least one sequence selected from the group consisting of SEQ ID NO:9, SEQ ID NO:10 and SEQ ID NO:11 and at least one further sequence selected from the group consisting of SEQ ID NO:21, SEQ ID NO:22 and SEQ ID NO:23. In particular, the sequence may have at least 80% amino acid identity to SEQ ID NO:12 and the further sequence may have at least 80% amino acid identity to SEQ ID NO:24.

The present invention also provides at least one isolated polypeptide comprising at least one sequence selected from the group consisting of SEQ ID NO:44, SEQ ID NO:45 and SEQ ID NO:46 and/or at least one further sequence selected from the group consisting of SEQ ID NO:52, SEQ ID NO:53 and SEQ ID NO:54. In particular, the sequence may have at least 80% amino acid identity to SEQ ID NO:47 and the further sequence may have at least 80% amino acid identity to SEQ ID NO:55.

The polypeptide according to the present invention may be at least one HBV epitope-reactive exogenous TCR. In particular, the HBV epitope may be HBc18-27, HBs370-79 and/or a mutant thereof. More in particular, the polypeptide may be at least one soluble TCR or a fragment thereof. Even more in particular, the soluble TCR or fragment thereof may be linked to at least one anti-viral drug.

According to one aspect, the present invention provides at least one construct comprising the polynucleotide of the present invention operably connected to at least one promoter.

According to another aspect, the present invention provides at least one vector comprising the construct according to the present invention or the polynucleotide according to the present invention.

According to still another aspect, the present invention provides at least one T cell comprising the vector or the construct according to the present invention.

According to one aspect, the present invention provides at least one method of preparing at least one T cell comprising at least one HBV epitope-reactive exogenous TCR for delivery to at least one subject the method comprising transducing at least one T cell isolated from the subject with the construct of or the vector of the present invention.

According to another aspect, the present invention provides at least one method of preparing at least one HBV epitope-reactive exogenous TCR comprising:
(a) isolating at least one HBV-epitope reactive T cell from at least one HBV-exposed individual that resolved HBV infection;
(b) cloning at least one polynucleotide sequence encoding at least one α- and/or β-chain of at least one TCR cell receptor from the HBV-epitope reactive T cell of step (a);
(c) delivering the polynucleotide sequence of step (b) to at least one cell; and
(d) incubating the cell under conditions suitable for expression of the HBV epitope-reactive exogenous T cell receptor by the cell.

In particular, the method of preparing at least one HBV epitope-reactive exogenous TCR comprises the isolation of at least one T cell, step (a) which may be HBc18-27 epitope reactive and/or HBs370-79 epitope reactive.

According to one aspect, the present invention provides at least one cell according to the present invention, for use in the treatment of HBV infection and/or HBV-related hepatocellular carcinoma.

According to another aspect, the present invention provides at least one method of treating HBV and/or inhibiting reactivation of HBV in at least one subject comprising administering to the subject at least one immunotherapeutically effective amount of cells, at least one vector and/or at least one polypeptide according to any aspect of the present invention.

According to still another aspect, the present invention provides at least one method of treating HBV-related hepatocellular carcinoma in at least one subject comprising administering to the subject at least one immunotherapeutically effective amount of cells, at least one vector and/or at least one polypeptide according to any aspect of the present invention.

According to one aspect, the present invention provides at least one in vitro method for diagnosing at least one subject that is able to resolve HBV infection, the method comprising:
(a) providing at least one sample from at least one subject;
(b) detecting the presence of at least one polynucleotide comprising, substantially consisting of or consisting of at least one nucleic acid sequence selected from SEQ ID NO: 4, SEQ ID NO: 8, SEQ ID NO: 16, SEQ ID NO: 20, SEQ ID NO: 43, SEQ ID NO: 51, a homologue and/or a fragment thereof; and/or
(c) detecting the presence of at least one polypeptide comprising, substantially consisting of or consisting of the amino acid sequence of SEQ ID NO: 12, SEQ ID NO: 24, SEQ ID NO: 47, SEQ ID NO: 55, a homologue and/or a fragment thereof;
wherein the presence of the polynucleotide and/or the polypeptide is indicative of the subject being able to resolve the HBV infection.

According to yet another aspect, the present invention provides at least one in vitro method for diagnosing at least one subject as having or as being at risk of having HBV infections and/or HBV related hepatocellular carcinoma, the method comprising:
(a) providing at least one sample from at least one subject;
(b) detecting the presence of at least one polynucleotide comprising, substantially consisting of or consisting of at least one nucleic acid sequence selected from SEQ ID NO: 4, SEQ ID NO: 8, SEQ ID NO: 16, SEQ ID NO: 20, SEQ ID NO: 43, SEQ ID NO: 51, a homologue and/or a fragment thereof; and/or
(c) detecting the presence of at least one polypeptide comprising, substantially consisting of or consisting of the amino acid sequence of SEQ ID NO: 12, SEQ ID NO: 24, SEQ ID NO: 47, SEQ ID NO: 55, a homologue and/or a fragment thereof;
wherein the absence of the polynucleotide and/or the polypeptide correlates with the likelihood of the subject as having or as being at risk for having HBV-infection and/or HBV-related hepatocellular carcinoma.

According to another aspect, the present invention provides at least one use of at least one cell, at least one vector and/or at least one polypeptide according to any aspect of the present invention in the preparation of a medicament for treating HBV infection and/or HBV-related hepatocellular carcinoma.

According to still another aspect, the present invention provides at least one kit for detecting and/or treatment of HBV infection and/or HBV-related hepatocellular carcinoma, the kit comprising at least one cell, at least one vector and/or at least one polypeptide according to any aspect of the present invention.

BRIEF DESCRIPTION OF THE FIGURES

FIG. 1 was partly taken from Schumacher et al., 2002.

FIG. 2 (B) shows a graph with the results of V beta typing of a potential T cell clone, C183, which was derived from a resolved HLA-A201 HBV patient using staining with a panel of TCR V beta monoclonal antibodies (MAbs). MAbs reacting with the human TCR V beta region are almost as specific as a private idiotypic MAb in identifying T cell clones. This method was thus used to evaluate expression of V beta gene families. The clone, C183, which was found to be highly specific to HBV core 18-27 (HBc18-27) epitope. The results suggest that all T cells were Vβ8 positive.

FIG. 4 (A) shows the results of HBc18-27 specific Cytotoxic T lymphocyte (CTL), C183, incubated with parental, vector only, HepG2 cell line (HepG2TA2-7) for 5 h as a control. The control was tested for cytokine release and cytotoxic degranulation (CD107a+ staining), which revealed that C183 did not respond to the control cell line HepG2TA2-7 as there was no activation to degranulate (CD107a+) and did not produce IFN-γ.

FIG. 4 (B) shows that C183 T cell clone activation after co-culture with HepG2.105 cells which expressed different levels of the HBV antigen stimulated IFN-γ production and degranulation, indicating the C183 T cell clone recognizes the HBc18-27 epitope processed and presented by hepatocellular carcinoma cells. 84% of T cell clones were activated after 5 h co-culture with HepG2 cells expressing HBV.

FIG. 7 (A) shows the FACS analysis of peripheral blood lymphocytes (PBL) when they were mock transduced (negative control) or transduced with the HBc18-27 A201 TCR comprised of Vβ8.2 and Vα3 chains. PBL were stained for Vβ8 chain 3 days after transduction to determine expression of the introduced HBc18-27 TCR. Mock transduced PBL expressed endogenous levels of Vβ8 (CD8+=1.8%; CD4+=2.1). Expression of Vβ8 increased substantially after transduction with HBc18-27 A201 TCR compared to mock transduced cells, which expressed only endogenous levels of Vβ8, indicating successful transduction and expression.

FIG. 7 (B) shows the results obtained when mock or HBc18-27 TCR transduced cells were stained with HBc18-27-A201 specific pentamer to determine if the Vα3 chain was expressed and properly paired with Vβ8.2 chain on the cell surface. Pentamer analysis showed that only HBc18-27 TCR transduced T cells expressed the appropriate α and β chains recognized by the HBc18-27-A201 specific pentamer and that the α and β chains were properly paired on the cell surface. No staining was detected in Mock transduced cells because PBL came from a healthy donor which was HLA-A2 negative.

FIG. 7 (C) shows the mean frequency of Vβ8+ T cells from 5 healthy, 5 HBeAg+ chronic HBV patients (HBV DNA>$10^7$ copies/ml), and 5 HBeAg-chronic HBV patients (HBV DNA<$10^6$ copies/ml). This indicates that the transduced Vβ8 TCR chain is expressed equally well in chronic HBV patients and healthy donors.

FIG. 7 (D) shows the mean frequency of HBc18-27-A201 specific pentamer+ T cells from 5 healthy, 5 HBeAg+ chronic HBV patients (HBV DNA>$10^7$ copies/ml), and 5 HBeAg− chronic HBV patients (HBV DNA<$10^6$ copies/ml). This indicates that the properly paired transduced TCR is expressed equally well in chronic HBV patients and healthy donors.

FIG. 8 (B) shows that HBc18-27 TCR transduced T cells from chronic HBV patients are equally functional to healthy donors. Mean frequency of IFN-γ, TNF-α and IL-2 positive cells from 5 healthy, 5 HBeAg+ chronic HBV patients (HBV DNA>$10^7$ copies/ml), and 5 HBeAg− chronic HBV patients (HBV DNA<$10^6$ copies/ml) are shown. The results show that T cells transduced with HBc18-27-A201 TCR become multifunctional.

FIG. 9 (A) shows the results when IFN-γ+ CD8+ HBc18-27 TCR transduced T cells and C183 T cell clones were co-cultured with T2 cells pulsed with increasing concentrations of HBc18-27 peptide for 5 h and then stained for IFN-γ. Data is presented as mean percentage of maximum response for HBc18-27 TCR transduced T cells derived from 5 healthy donors, 5 HBeAg+ chronic HBV patients (HBV DNA>$10^7$ copies/ml), and 5 HBeAg− chronic HBV patients (HBV DNA<$10^6$ copies/ml) where C183 is 100% specific while TCR transduced cell frequency varies. Results show that the affinity for the viral epitope of CD8+ HBc18-27 TCR transduced T cells derived from patient T cells was identical when compared to the original C183 T cell clone and recognized the epitope down to concentrations of 0.1-1 pg/ml.

FIG. 9 (B) shows the results when IFN-γ+ CD4+ HBc18-27 TCR transduced T cells and C183 T cell clones were co-cultured with T2 cells pulsed with increasing concentrations of HBc18-27 peptide for 5 h and then stained for IFN-γ. Data is presented as mean percentage of maximum response for HBc18-27 TCR transduced T cells derived from 5 healthy donors, 5 HBeAg+ chronic HBV patients (HBV DNA>$10^7$ copies/ml), and 5 HBeAg– chronic HBV patients (HBV DNA<$10^6$ copies/ml) where C183 is 100% specific while TCR transduced cell frequency varies. CD4+ HBc18-27 TCR transduced cells derived from patient T cells were less sensitive compared to C183 but 50% of HBc18-27 specific T cells were activated at 100 pg/ml indicating that the introduced HBc18-27 TCR was highly sensitive, even in the absence of the CD8 co-receptor.

FIG. 10 (A) shows histograms with the percentage of Vβ8+ T cells from mock, HBc18-WT-TCR and HBc18-Opt-TCR transduced PBL cells. Frequency of Vβ8+ cells was comparable between the optimized and wild type HBc18-TCR transduced cells.

FIG. 10 (B) shows the comparison of the expression level of Vβ8 in mock, HBc18-WT-TCR and HBc18-Opt-TCR transduced T cells. To compare the level of expression, mean fluorescent intensity (MFI) for Vβ8+ cells was used. The results show that there was no significant difference in the level of Vβ8 expression between optimized and wild type TCR transduced cells.

FIG. 10 (C) shows the results obtained from HBc18-27 HLA-A2 specific pentamer staining. Cells from each group mentioned above were stained with anti-CD8 and HBc18-27 HLA-A2 specific pentamers. Nearly a two-fold increase in the frequency of pentamer positive cells in T cells transduced with HBc18-Opt-TCR constructs were shown compared to the wild type TCR suggesting that the Vα3 chain may be expressed more efficiently from the codon optimized construct compared to the wild type sequence.

FIG. 12 (B) EBV transformed B cells expressing HLA-A0201, -A0206 or -A0207 subtypes were loaded with increasing concentrations of HBV genotype B/C HBc18-27 epitope (sequences provided in Table 1) and co-cultured with HBc-18-27 TCR transduced T cells for 5 h. T cell activation was measured by intracellular cytokine staining for IFN-γ. The results show that the HBc-18-27 TCR transduced T cells recognize the HBc18-27 eptiope presented by multiple HLA-A2 subtypes.

FIG. 12 (C) show the results when HLA-A2+ T2 cells were loaded with each of the mutant peptides of HBc18-27 epitope and co-cultured with HBc-18-27 TCR transduced T cells for 5 h. T cell recognition of the mutant peptides was determined by intracellular cytokine staining for IFN-γ. The sequences of the mutant peptides are provided in Table 1. As can be seen from the results, the HBc-18-27 TCR transduced T cells recognized various mutants of the HBc18-27 eptiope. The Unstim 1 and Unstim 2 refer to the control where the HLA-A2+ T2 cells were not loaded with any mutant peptide.

FIG. 13 (B) DiOC labeled HCC cell lines (HepG2, SNU-387, SNU-368) were loaded with increasing concentrations of HBc18-27 peptides and co-cultured with HBc-18-27 TCR transduced T cells at Effector to target ratio of 1:1 for 6 h in the presence of Propidium Iodide (PI). Dying target cells were DiOC+/PI+. Results are representative of 3 experiments. Effector T cells were considered to be IFN-γ+/CD8+ cells determined by intracellular cytokine staining after stimulation with peptide pulsed T2 cells. The results showed that HBc18-27 TCR transduced T cells are able to kill multiple HLA-A2+ HCC cell lines.

FIG. 14 (B) shows that HBs370-79 TCR transduced T cells recognize genotypic variants of the HBs370-79 epitope (The sequences of the genotypic variants are provided in Table 2). HBs370-79 TCR transduced T cells were co-cultured with HLA-A2+ T2 cells loaded with 1 μg/ml peptide of each genotype for 5 h and activation was assessed by CD107a labeling and staining for IFN-γ. Genotype A & D sequences are identical. The results show that HBs370-79 specific TCR recognizes genotypic variants of the HBs370-79 epitope.

DETAILED DESCRIPTION OF THE INVENTION

Figure 1:
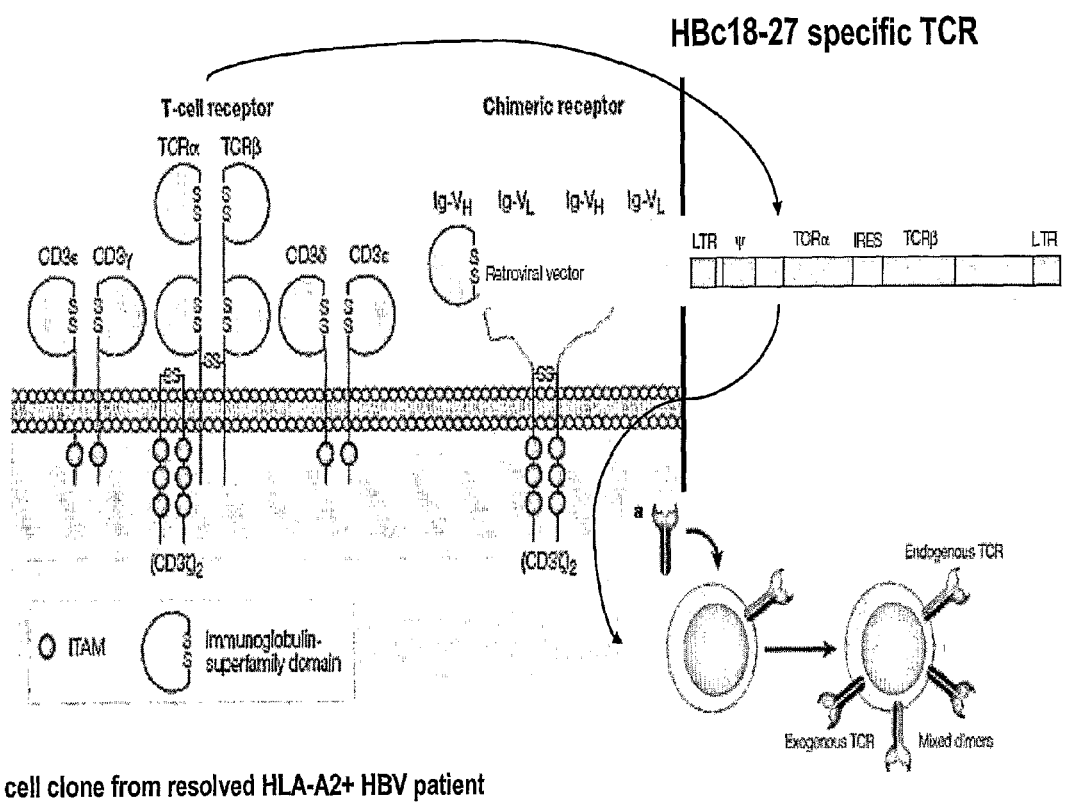
FIG. 1 shows a schematic diagram of the steps involved in producing a cell comprising at least one HBV epitope-reactive exogenous T cell receptor. It comprises the isolation of a T cell clone from an HLA-A2 positive HBV patient who has resolved the infection, using the T cell clone to form a retroviral vector construct encoding HBV T cell receptor and using the vector to form cells that express the HBV epitope-reactive exogenous T cell receptor.

Bibliographic references mentioned in the present specification are for convenience listed in the form of a list of references and added at the end of the examples. The whole content of such bibliographic references is herein incorporated by reference.

DEFINITIONS

For convenience, certain terms employed in the specification, examples and appended claims are collected here.

The term "comprising" is herein defined to be that where the various components, ingredients, or steps, can be conjointly employed in practicing the present invention. Accordingly, the term "comprising" encompasses the more restrictive terms "consisting essentially of" and "consisting of."

With the term "consisting essentially of" it is understood that the exogenous TCR polypeptide and/or polynucleotide according to the invention "substantially" comprises the indicated sequence as "essential" element. Additional sequences may be included at the 5' end and/or at the 3' end. Accordingly, a polypeptide "consisting essentially of" sequence X will be novel in view of a known polypeptide accidentally comprising the sequence X.

With the term "consisting of" it is understood that the polypeptide and/or polynucleotide according to the invention corresponds to at least one of the indicated sequence (for example a specific sequence indicated with a SEQ ID Number or a homologous sequence or fragment thereof).

The term "exogenous T cell receptor" (TCR) is herein defined as a recombinant TCR which is expressed in a cell by introduction of exogenous coding sequences for a TCR. In particular, the HBV epitope-reactive TCR may be expressed in a cell in which the TCR is either not natively expressed or is expressed at levels that are insufficient to induce a response by the cell or a responder cell upon TCR ligand binding.

The term "fragment" is herein defined as an incomplete or isolated portion of the full sequence of the HBV epitope-reactive exogenous TCR which comprises the active site(s) that confers the sequence with the characteristics and function of the HBV epitope-reactive exogenous TCR. In particular, it may be shorter by at least one nucleotide or amino acid. More in particular, the fragment comprises the active site(s) that enable the HBV epitope-reactive exogenous TCR to recognise the HBc18-27 epitope and/or the HBs370-79 epitope.

The term "HBV epitope-reactive T Cell Receptor (TCR)" is herein defined as a TCR which binds to an HBV epitope in the context of a Major Histocompatibility Complex (MHC) molecule to induce a helper or cytotoxic response in the cell expressing the recombinant TCR. In particular, the HBV epitope may be HBc18-27. More in particular, the HBV epitope may comprise the sequence of SEQ ID NO:25. The HBV epitope may be HBs370-79. More in particular, the HBV epitope may comprise the sequence of SEQ ID NO:56, SEQ ID NO:57 or SEQ ID NO:58.

The term "HBc 18-27 epitope" is herein defined as an epitope that can stimulate HLA class I restricted T cells. It may be used interchangeably in the present invention as HBc18, HBc18-27, HBc18-27 peptide and the peptide. The sequence of the epitope may be "FLPSDFFPSV" (SEQ ID NO:25). In the present invention, the term HBc18-27 is used to refer to the HBc18-27 epitope of genotype A/D prevalent amongst Caucasians of sequence SEQ ID NO:25 unless otherwise stated. The region of the T cell receptor that binds to the epitope is referred to as HBc18-27 TCR or HBc18 TCR.

The term "HBs370-79 epitope" is herein defined as an epitope that can stimulate HLA class I restricted T cells. The sequence of the epitope may be "SIVSPFIPLL" (SEQ ID NO:56). In the present invention, the term HBs370-79 is used to refer to the HBs370-79 epitope of genotype A/D prevalent amongst Caucasians of sequence SEQ ID NO:56 unless otherwise stated. The region of the T cell receptor that binds to the epitope is referred to as HBs370-79 TCR.

The term "immunotherapeutically effective amount" is herein defined as an amount which results in an immune-mediated prophylactic or therapeutic effect in the subject, i.e., that amount which will prevent or reduce symptoms at least 50% compared to pre-treatment symptoms or compared to a suitable control.

The term "isolated" is herein defined as a biological component (such as a nucleic acid, peptide or protein) that has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been isolated thus include nucleic acids and proteins purified by standard purification methods. The term also embraces nucleic acids, peptides and proteins prepared by recombinant expression in a host cell as well as chemically synthesized nucleic acids.

The term "operably connected" herein defined as a functional linkage between regulatory sequences (such as a promoter and/or array of transcription factor binding sites) and a second nucleic acid sequence, wherein the regulatory sequences direct transcription of the nucleic acid corresponding to the second sequence.

The term "mutant" or "mutant form" of a TCR epitope is herein defined as one which has at least one amino acid sequence that varies from at least one reference virus-encoded sequence via substitution, deletion or addition of at least one amino acid, but retains the ability to bind and activate the TCR bound and activated by the non-mutated epitope. In particular, the mutants may be naturally occurring or may be recombinantly or synthetically produced.

The term "soluble TCR" is herein defined as a soluble (secreted) form of the membrane bound TCR which is the molecule that is responsible for the T cell's recognition of the antigen for which it is specific. In its soluble form it is analogous to a monoclonal antibody except that it recognizes fragments of peptides associated with MHC molecules while antibodies recognize determinants on a whole protein. In particular, the isolated polypeptide of the present invention may be used for producing a soluble TCR using any method known in the art. More in particular, the soluble TCR may bind to the HBc18-27 and/or HBs370-79 epitope of HBV.

The term "subject" is herein defined as vertebrate, particularly mammal, more particularly human. For purposes of research, the subject may particularly be at least one animal model, e.g., a mouse, rat and the like. In particular, for the animal models, the sequence of the TCR α- and β-chains may be selected based on species. In some cases, transgenic animals expressing human MHC molecules may also be useful in evaluating specific aspects of the present invention.

A person skilled in the art will appreciate that the present invention may be practised without undue experimentation according to the method given herein. The methods, techniques and chemicals are as described in the references given or from protocols in standard biotechnology and molecular biology text books.

In one aspect of the present invention, there is provided at least one isolated cell comprising at least one HBV epitope-reactive exogenous T cell receptor (TCR) and/or fragment thereof. Such cells may be suitable for use in adoptive transfer protocols to provide a particularly effective mode of treatment. The isolated cells of the present invention may circumvent the problem of deletion and sub-optimal function of HBV-specific CD8+ and CD4+ cells which may be present in patients with chronic HBV infection. In particular, the TCR from a patient who resolved the HBV infection may be used to redirect the specificity of the lymphocytes of chronic HBV patients for TCR transfer.

In particular, HBV-reactive TCRs may be prepared by transforming or transducing at least one isolated cell with one or more polynucleotides encoding functional α- and/or β-chains and/or polypeptides of functional α- and/or β-chains that may assemble to form at least one functional HBV-epitope reactive TCR. In particular, the isolated cell may be isolated using any technique known in the art. More in particular, at least one cell isolation kit, Ficoll-Paque density gradient centrifugation, BD FACSAria Cell Sorting System and the like may be used to isolate the cell.

The isolated cell may be at least one autologous cell, i.e., they may be derived from at least one subject that may receive the resultant transduced or transformed cells. In particular, the isolated cells may be derived from the peripheral blood lymphocytes and/or hematopoietic stem cells of the subject.

More in particular, the isolated cell may be at least one T cell that innately expresses at least one CD4+ cell surface marker, at least one CD8+ cell surface marker, both CD4+ and CD8+ marker or neither CD4+ nor CD8+ cell surface markers. In particular, the cell according to the present invention may be at least one T cell that also natively expresses at least one TCR. The HBV-reactive exogenous TCR may bind the same epitope as the natively expressed TCR, and/or may bind a different epitope. In particular, the HBV-reactive exogenous TCR may be expressed in at least one cell in which the TCR may be either not natively expressed or may be expressed at levels that may be insufficient to induce response by the cell or responder cell upon TCR ligand binding. In particular, the isolated cell according to the present invention may be transduced with two or more different HBV-reactive exogenous TCRs, i.e., TCRs which bind to two or more different HBV epitopes.

HBV-exposed patients who have cleared their viral infections, may provide excellent source of HBV-reactive T cells expressing high affinity TCRs. In particular, HBV-epitope reactive TCRs may be prepared by isolating at least one HBV-reactive T cell from at least one HBV-exposed aviremic individual, and cloning the polynucleotide sequence encoding the α- and β-chains of the TCR from the HBV reactive T cell. Once these sequences have been cloned using standard methods known in the art, the sequences may be delivered to at least one isolated cell and the isolated cell may be incubated under conditions suitable for expression of the TCR by the isolated cell. More in particular, the suitable conditions may include standard cell culture conditions. When the TCR is expressed in vitro or ex vivo, the cell expressing the TCR may be evaluated for reactivity with HBV epitopes, among other parameters of interest, as known in the art and as exemplified below. In some protocols, i.e., those wherein the vector may be administered to at least one subject, the TCR may also be expressed in vivo to provide a therapeutic effect in at least one subject in need thereof, i.e., at least one subject with acute or chronic HBV infection or HBV-associated condition.

The HBV-reactive TCRs according to the present invention may be functional in the isolated cell in which they may be expressed. In particular, they may be functional heterodimers of α and β TCR chains associated with a CD3 complex that recognizes at least one HBV epitope in the context of at least one Class I or Class II MHC molecule. In humans, the MHC restriction of at least one epitope may be dependent on at least one particular Human Leukocyte Antigen (HLA) expressed by at least one cell presenting the antigen. HBV-reactive TCRs that may recognize HBV epitopes restricted to any HLA type (i.e., HLA-A, HLA-B, HLA-C, HLA-DPA1, HLA-DPB1, HLA-DQA1, HLA-DQB1, HLA-DRA, and HLA-DRB1) may be used in the present invention. For purposes of study, the HBV-reactive TCR may recognize at least one HBV epitope in the context of at least one MHC molecule of at least one species other than human, e.g., H-2K of mouse.

In particular, the HBV-reactive TCR recognizes HBV epitopes that may be HLA-A2 restricted. Approximately 50% of the general population expresses the MHC class I molecule HLA-A2, an HLA-A serotype. Therefore, HLA-A2-restricted TCRs may find widespread therapeutic use. In particular, the subtype may identify gene products of many HLA-A*02 alleles, comprising HLA-A*0201, *0202, *0203, *0206, and *0207 gene products. There may be distinct differences in the subtypes between Caucasian and Asian populations. Whereas more than 95% of the HLA-A2 positive Caucasian population is HLA-A0201 the HLA-A2 positive Chinese population may be broken down into 23% HLA-A0201; 45% HLA-A0207; 8% HLA-A0206; 23% HLA-A0203.

The TCRs of the present invention may be HBV-epitope reactive. A list of known immunoreactive HBV epitopes and their sequences may be found on page 233, chapter 11 (The effect of pathogens on the immune system: Viral hepatitis) of the book In immunodominance: The choice of the Immune System, J. A. Frelinger, ed (Weinheim: Wiley-VCH) which is herein incorporated by reference. The HBV epitope may comprise at least one core antigen, envelope antigen, surface antigen and/or mutants thereof.

In particular, the HBV epitope may comprise at least one hepatitis B core antigen, and/or mutants thereof. More in particular, the HBV epitope may comprise HBc18-27, and/or mutants thereof. The HBc18-27 epitope may comprise "FLPSDFFPSV" (SEQ ID NO:25) or mutants thereof. Furthermore, the HBc18-27 epitope present in genotype A and D which may comprise "FLPSDFFPSV" (SEQ ID NO: 25), which are most prevalent in Europe, differs from HBc18-27 epitope of genotypes B and C which may comprise "FLPSDFFPSI" (SEQ ID NO: 26), which are most prevalent in Asia.

In particular, the HBV epitope may comprise at least one hepatitis B envelope antigen, and/or mutants thereof. More in particular, the HBV epitope may comprise HBs370-79, and/or mutants thereof. The HBs370-79 epitope may comprise "SIVSPFIPLL" (SEQ ID NO:56) or mutants thereof. Furthermore, the HBs370-79 epitope present in genotype A and D which may comprise "SIVSPFIPLL" (SEQ ID NO:56), which are most prevalent in Europe, differs from HBs370-79 epitope of genotype B which may comprise "NILSPFMPLL" (SEQ ID NO: 57), and epitope of genotype C which may comprise "NILNPFLPLL" (SEQ ID NO: 58), which are most prevalent in Asia.

In particular, the cell according to the present invention may further comprise at least one second HBV epitope-reactive exogenous TCR and/or fragment thereof, wherein the second HBV-reactive exogenous TCR may be the same epitope as the first epitope or different from the first HBV epitope. In particular, the second HBV epitope may be HBs370-79 and the first epitope may be HBc18-27.

The exogenous TCR may comprise at least one α-chain comprising at least one amino acid sequence selected from the group consisting the sequences SEQ ID NO:9, SEQ ID NO:10 and SEQ ID NO:11 and/or mutants thereof. In particular, the exogenous TCR comprises at least one α-chain comprising the sequences SEQ ID NO:9, SEQ ID NO:10 and SEQ ID NO:11. More in particular, the α-chain comprises all three sequences, SEQ ID NO:9, SEQ ID NO:10 and SEQ ID NO:11. The α-chain may comprise the sequences of SEQ ID NO:9, SEQ ID NO:10 and SEQ ID NO:11 consecutively. In particular, the α-chain may consist essentially of the sequences SEQ ID NO:9, SEQ ID NO:10 and SEQ ID NO:11. All sequences used in the present invention are given in Tables 1 and 2.

The exogenous TCR may further comprise at least one β-chain comprising at least one amino acid sequence selected from the group consisting of the sequences SEQ ID NO:21, SEQ ID NO:22 and SEQ ID NO:23 and/or mutants thereof. In particular, the β-chain may comprise all three sequences, SEQ ID NO:21, SEQ ID NO:22 and SEQ ID NO:23. In particular, the β-chain may comprise the sequences of SEQ ID NO:21, SEQ ID NO:22 and SEQ ID NO:23 consecutively. More in particular, the β-chain may consist essentially of the sequences SEQ ID NO:21, SEQ ID NO:22 and SEQ ID NO:23.

In particular, the exogenous TCR may comprise at least one α-chain having at least 80% amino acid identity to SEQ ID NO:12 or a fragment thereof and/or at least one β-chain having at least 80% amino acid identity to SEQ ID NO:24 or a fragment thereof. In particular, the α-chain and β-chain may be at least about 85%, at least about 90%, or at least about 95% identical to SEQ ID NO:12 and SEQ ID NO:24 respectively. More in particular, the α-chain may comprise all sequences SEQ ID NO:9, SEQ ID NO:10 and SEQ ID NO:11 and β-chain may comprise all sequences SEQ ID NO:21, SEQ ID NO:22 and SEQ ID NO:23.

The exogenous TCR may comprise at least one α-chain comprising at least one amino acid sequence selected from the group consisting the sequences SEQ ID NO:44, SEQ ID NO:45 and SEQ ID NO:46 and/or mutants thereof. In particular, the exogenous TCR comprises at least one α-chain comprising the sequences SEQ ID NO:44, SEQ ID NO:45 and SEQ ID NO:46. More in particular, the α-chain comprises all three sequences, SEQ ID NO:44, SEQ ID NO:45 and SEQ ID NO:46. The α-chain may comprise the sequences of SEQ ID NO:44, SEQ ID NO:45 and SEQ ID NO:46 consecutively. In particular, the α-chain may consist essentially of the sequences SEQ ID NO:44, SEQ ID NO:45 and SEQ ID NO:46. All sequences used in the present invention are given in Tables 1 and 2.

The exogenous TCR may further comprise at least one β-chain comprising at least one amino acid sequence selected from the group consisting of the sequences SEQ ID NO:52, SEQ ID NO:53 and SEQ ID NO:54 and/or mutants thereof. In particular, the β-chain may comprise all three sequences, SEQ ID NO:52, SEQ ID NO:53 and SEQ ID NO:54. In particular, the β-chain may comprise the sequences of SEQ ID NO:52, SEQ ID NO:53 and SEQ ID NO:54 consecutively. More in particular, the β-chain may consist essentially of the sequences SEQ ID NO:52, SEQ ID NO:53 and SEQ ID NO:54.

In particular, the exogenous TCR may comprise at least one α-chain having at least 80% amino acid identity to SEQ ID NO:47 or a fragment thereof and/or at least one β-chain having at least 80% amino acid identity to SEQ ID NO:55 or a fragment thereof. In particular, the α-chain and β-chain may be at least about 85%, at least about 90%, or at least about 95% identical to SEQ ID NO:47 and SEQ ID NO:55 respectively. More in particular, the α-chain may comprise all sequences SEQ ID NO:44, SEQ ID NO:45 and SEQ ID NO:46 and β-chain may comprise all sequences SEQ ID NO:52, SEQ ID NO:53 and SEQ ID NO:54.

The sequences encoding the α-chain and β-chain have been determined to be the amino acid sequence for at least one productively rearranged α-chain and β-chain respectively of a TCR reactive against HBV epitope HBc18-27 and/or HBs370-79.

More in particular, the exogenous TCR reactive against HBV epitope HBc18-27 may comprise at least one α-chain of SEQ ID NO:12 and/or at least one β-chain of SEQ ID NO:24. Even more in particular, the exogenous TCR reactive against HBV epitope HBc18-27 may consists essentially of at least one α-chain of SEQ ID NO:12 and at least one β-chain of SEQ ID NO:24. The exogenous TCR reactive against HBV epitope HBc18-27 may consists of at least one α-chain of SEQ ID NO:12 and at least one β-chain of SEQ ID NO:24. In particular, the exogenous TCR reactive against HBV epitope HBc18-27 may consist of two α-chains and two β-chains.

More in particular, the exogenous TCR reactive against HBV epitope HBs370-79 may comprise at least one α-chain of SEQ ID NO:47 and/or at least one β-chain of SEQ ID NO:55. Even more in particular, the exogenous TCR reactive against HBV epitope HBs370-79 may consists essentially of at least one α-chain of SEQ ID NO:47 and at least one β-chain of SEQ ID NO:55. The exogenous TCR reactive against HBV epitope HBs370-79 may consists of at least one α-chain of SEQ ID NO:47 and at least one β-chain of SEQ ID NO:55. In particular, the exogenous TCR reactive against HBV epitope HBs370-79 may consist of two α-chains and two β-chains.

Percentage identity may be determined using the algorithm of Karlin and Altschul (Proc. Natl. Acad. Sci. 87: 2264-68 (1990), modified Proc. Natl. Acad. Sci. 90: 5873-77 (1993)). Such algorithm is incorporated into the BLASTx program, which may be used to obtain amino acid sequences homologous to a reference polypeptide. The present invention may also encompass TCR α- or β-chains having amino acid sequences including conservative amino acid substitutions. Such substitutions are well known in the art.

According to another aspect, the present invention provides at least one isolated polynucleotide comprising at least one sequence encoding at least one α-chain and/or at least one sequence encoding at least one β-chain wherein, the encoded α-chain and β-chain may be part of at least one HBV epitope-reactive TCR.

In particular, the sequence encoding the α-chain comprises at least one sequence selected from SEQ ID NO:1 and SEQ ID NO:5, at least one sequence selected from SEQ ID NO:2 and SEQ ID NO:6 and at least one sequence selected from SEQ ID NO:3 and SEQ ID NO:7 and/or the sequence encoding the β-chain comprises at least one sequence selected from SEQ ID NO:13 and SEQ ID NO:17, at least one sequence selected from SEQ ID NO:14 and SEQ ID NO:18 and at least one sequence selected from SEQ ID NO:15 and SEQ ID NO:19. More in particular, the sequence encoding the α-chain may comprise SEQ ID NO:5, SEQ ID NO:6 and SEQ ID NO:7 and/or the sequence encoding the β-chain may comprise SEQ ID NO:17, SEQ ID NO:18 and SEQ ID NO:19.

In particular, the sequence encoding the α-chain of the HBc-18-27 epitope-reactive TCR may have at least 80% sequence identity to SEQ ID NO:4 or SEQ ID NO:8 and/or the sequence encoding the β-chain of the HBc-18-27 epitope-reactive exogenous TCR may have at least 80% sequence identity to SEQ ID NO:16 or SEQ ID NO:20. In particular, the sequence(s) encoding the α-chain and β-chain may be at least about 85%, at least about 90%, or at least about 95% identical to SEQ ID NO:4 or SEQ ID NO:8 and SEQ ID NO:16 or SEQ ID NO:20 respectively. More in particular, the sequence encoding the α-chain may be selected from the group consisting of SEQ ID NO:4 and SEQ ID NO:8, and/or the sequence encoding the β-chain may be selected from the group consisting of SEQ ID NO:16 and SEQ ID NO:20. The HBc-18-27 epitope-reactive exogenous TCR may comprise two α-chains encoded by the sequence SEQ ID NO:8 and two β-chains encoded by SEQ ID NO:20. More in particular, the α-chain and β-chain may be encoded by nucleotide sequences that comprise the consecutive sequence shown in SEQ ID NO:4 or SEQ ID NO:8 and SEQ ID NO:16 or SEQ ID NO:20 respectively.

Even more in particular, the exogenous TCR may consists essentially of at least one α-chain encoded by SEQ ID NO:4 or SEQ ID NO:8 and at least one β-chain encoded by SEQ ID NO:16 or SEQ ID NO:20. The exogenous TCR may consist of at least one α-chain encoded by SEQ ID NO:4 or SEQ ID NO:8 and at least one β-chain encoded by SEQ ID NO:16 or SEQ ID NO:20. In particular, the exogenous TCR may consist of two α-chains encoded by SEQ ID NO:4 or SEQ ID NO:8 and two β-chains encoded by SEQ ID NO:16 or SEQ ID NO:20.

In particular, the sequence encoding the α-chain comprises SEQ ID NO:40, SEQ ID NO:41 and SEQ ID NO:42 and/or the sequence encoding the β-chain comprises SEQ ID NO:48, SEQ ID NO:49, and SEQ ID NO:50.

More in particular, the sequence encoding the α-chain of the HBs370-79 epitope-reactive exogenous TCR may have at least 80% sequence identity to SEQ ID NO:43 and the β-chain of the HBs370-79 epitope-reactive exogenous T cell receptor has at least 80% sequence identity to SEQ ID NO:51. In particular, the sequence(s) encoding the α-chain and β-chain may be at least about 85%, at least about 90%, or at least about 95% identical to SEQ ID NO:43 and/or SEQ ID NO:51 respectively. More in particular, the sequence encoding the α-chain may be SEQ ID NO:43 and SEQ ID NO:51, and/or the sequence encoding the β-chain may be SEQ ID NO:51. The HBs370-79 epitope-reactive exogenous TCR may comprise two α-chains encoded by the sequence SEQ ID NO:43 and two β-chains encoded by SEQ ID NO:51. More in particular, the α-chain and β-chain may be encoded by nucleotide sequences that comprise the consecutive sequence shown in SEQ ID NO:43 and SEQ ID NO:51 respectively.

According to another aspect, the present invention provides at least one isolated polypeptide encoded by the polynucleotides of the present invention.

According to still another aspect, the present invention provides at least one isolated polypeptide comprising at least one amino acid sequence selected from the group consisting of SEQ ID NO:9, SEQ ID NO:10 and SEQ ID NO:11. In particular, the polypeptide may have at least 80% amino acid identity to SEQ ID NO:12. More in particular, the polypeptide may be at least about 85%, at least about 90%, or at least about 95% identical to SEQ ID NO:12.

The present invention also provides at least one isolated polypeptide comprising at least one sequence selected from the group consisting of SEQ ID NO:44, SEQ ID NO:45 and SEQ ID NO:46. In particular, the polypeptide may have at least 80% amino acid identity to SEQ ID NO:47. More in particular, the polypeptide may be at least about 85%, at least about 90%, or at least about 95% identical to SEQ ID NO:47.

The polypeptide may further comprise at least one sequence selected from the group consisting of SEQ ID NO:21, SEQ ID NO:22 and SEQ ID NO:23. In particular, the further sequence may have at least 80% amino acid identity to SEQ ID NO:24. More in particular, the further sequence may be at least about 85%, at least about 90%, or at least about 95% identical to SEQ ID NO:24. Even more in particular, the polypeptide may comprise the consecutive sequence of amino acids shown in SEQ ID NO:12 and SEQ ID NO:24 respectively.

The polypeptide may further comprise at least one sequence selected from the group consisting of SEQ ID NO:52, SEQ ID NO:53 and SEQ ID NO:54. In particular, the further sequence may have at least 80% amino acid identity to SEQ ID NO:55. More in particular, the further sequence may be at least about 85%, at least about 90%, or at least about 95% identical to SEQ ID NO:55. Even more in particular, the polypeptide may comprise the consecutive sequence of amino acids shown in SEQ ID NO:47 and SEQ ID NO:55 respectively.

The polypeptide according to the present invention may be at least one HBV epitope-reactive exogenous TCR. In particular, the polypeptide may be functionally equivalent to a specifically exemplified TCR sequence that may have been modified by single or multiple amino acid substitutions, by addition and/or deletion of amino acids, or where one or more amino acids have been chemically modified, but which nevertheless retains the binding specificity and high affinity binding activity of the TCR protein of the present invention to the HBV epitope. In particular, the HBV epitope may be HBc18-27, HBs370-79 or a mutant thereof. More in particular, the polypeptide may be at least one soluble TCR. Even more in particular, the soluble TCR protein may lack the portions of the native cell-bound TCR and may be stable in solution (i.e., it does not generally aggregate in solution when handled as described herein and under standard conditions for protein solutions).

The soluble TCR may be prepared by any method known in the art. Examples of processes that may be used to prepare the soluble TCR may comprise but are not limited to constructing polymeric receptor chains in which an immunoglobulin heavy chain variable region from at least one phosphorylcholine-specific antibody may be substituted with TCR α and β variable regions, introducing translational termination codons upstream of the TCR transmembrane region or replacing the transmembrane domains of the TCR α and β chain cDNAs with a signal for glycosylphosphatidyl inositol (GPI) linkage from the carboxy terminus of the GPI linked protein Thy-1.

The soluble TCR may be linked to at least one anti-viral drug. The anti-viral drug may target HBV. For example, anti-viral drugs may comprise, but are not limited to, adefovir dipivoxil, interferon alfa-2b, pegylated interferon alfa-2a, lamivudine, entecavir, telbivudine and the like.

In particular, the soluble TCR may be linked to the anti-viral drugs to form soluble TCR-drug conjugates by any means known in the art. The link may be a chemical moiety comprising a covalent bond or a chain of atoms that covalently attaches a soluble TCR to a drug moiety. Linkers may comprise a divalent radical such as an alkylene, an arylene, a heteroarylene, moieties such as: —(CR2)nO(CR2)n-; repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, caproamide and the like.

According to one aspect, the present invention provides at least one construct comprising the polynucleotide of the present invention operably connected to at least one promoter. The coding sequences for α- and β-chains of the TCR may be operably connected to at least one promoter functional in the isolated cell. Suitable promoters may be constitutive and inducible promoters, and the selection of an appropriate promoter may be well within the skill in the art. For example, suitable promoters may comprise, but are not limited to, the retroviral LTR, the SV40 promoter, the CMV promoter and cellular promoters (e.g., the β-actin promoter).

According to another aspect, the present invention provides at least one vector comprising the construct according to the present invention or the polynucleotide according to the present invention. In particular, the vectors may comprise, but not limited to, lentiviral vectors, retroviral vectors, adenoviral vectors, adeno-associated virus vectors and Herpes Simplex Virus vectors. More in particular, retroviral vectors may be used for delivery of the constructs either in vitro, ex vivo or in vivo, as described in the examples.

According to still another aspect, the present invention provides at least one T cell comprising the vector, the construct or the polypeptide according to the present invention.

According to one aspect, the present invention provides at least one method of preparing at least one T cell comprising at least one HBV epitope-reactive exogenous TCR for delivery to at least one subject comprising transducing at least one T cell isolated from the subject with the construct of and/or the vector of the present invention. Constructs and vectors according to the present invention may be delivered to cells in vitro, ex vivo or in vivo using any number of methods known to those of skill in the art. For example, if the cells are in vitro or ex vivo, they may be transformed or transduced according to standard protocols, e.g., those described in Molecular Cloning: A Laboratory Manual, 3d ed., Sambrook and Russell, CSHL Press (2001), incorporated herein by reference. Examples of methods may comprise but are not limited to, the $CaCl_2$ chemical method, electroporation and the like. In particular, the constructs according to the present invention may be delivered into the cells in viva Suitable methods of delivery of polynucleotide constructs are known in the art, and may comprise but are not limited to, viral vectors, nanoparticles, gold particles, lipoplexes and/or polyplexes.

According to another aspect, the present invention provides at least one method of preparing at least one HBV epitope-reactive exogenous TCR comprising:
(a) isolating at least one HBV-epitope reactive T cell from at least one HBV-exposed individual that resolved HBV infection;
(b) cloning at least one polynucleotide sequence encoding at least one α- and/or β-chain of at least one TCR from the HBV-epitope reactive T cell of step (a);
(c) delivering the polynucleotide sequence of step (b) to at least one cell; and
(d) incubating the cell under conditions suitable for expression of the HBV epitope-reactive exogenous T cell receptor by the cell.

In particular, the HBV-epitope reactive T cell of step (a) mentioned above may be HBc18-27 epitope reactive and/or HBs370-79 reactive.

According to one aspect, the present invention provides at least one cell, at least one vector and/or at least one polypeptide according to all aspects of the present invention, for use in the treatment of HBV infection and/or HBV-related hepatocellular carcinoma.

According to another aspect, the present invention provides at least one method of treating HBV and/or inhibiting reactivation of HBV in at least one subject comprising administering to the subject at least one immunotherapeutically effective amount of cells, at least one vector and/or at least one polypeptide according to any aspect of the present invention.

A further possible application of the HBV-TCR redirected approach is in patients with hepatocellular carcinoma (HCC). Chronic infection with HBV is the most important risk factor for the development of this liver tumour and integration of HBV-DNA into hepatocytes frequently occurs in tumour transformed cells. The therapy of HCC by conventional chemotherapy, radiation or surgical resection presents severe limitations. HBV-specific T cells have the potential to recognize and kill HCC cells expressing HBV antigens and adoptive transfer of HBV-TCR-redirected T cells may have the potential to obtain regression of HCC. Such results were obtained in nasopharyngeal carcinoma, a tumour expressing an Epstein-Barr Virus (EBV) protein, where infusion of EBV-specific CD8+ cells showed promising results. Vectors comprising polynucleotides encoding TCRs, and/or cells comprising at least one HBV-epitope reactive TCR may thus be useful in the treatment of HCC.

Accordingly, the present invention provides at least one method of treating HBV-related hepatocellular carcinoma in at least one subject comprising administering to the subject at least one immunotherapeutically effective amount of cells, at least one vector and/or at least one polypeptide according to any aspect of the present invention.

Vectors comprising polynucleotides encoding TCRs, and/or cells comprising at least one HBV-epitope reactive TCR prepared as described above, may be suitably administered to a subject to treat acute or chronic HBV infection or conditions (including, e.g., hepatocellular carcinoma) in the subject.

The cells expressing HBV-epitope reactive TCRs, vectors comprising polynucleotides encoding HBV-epitope reactive TCR and/or the polypeptide encoding the HBV-epitope reactive TCR may be prophylactically administered to at least one subject to inhibit reactivation of HBV infection. In particular, vectors of the invention may be administered to cells from at least one subject ex vivo. More in particular, modes of administration of polynucleotide and/or viral vectors will be those that specifically and/or predominantly deliver the TCR coding sequences to T cells and/or hematopoietic stem cells. In the case of a retroviral vector, it may be anticipated that suitable dosages will range from about 0.1 µg/$10^6$ cells to about 10 µg/$10^6$ cells, such as in the range from about 1 µg/$10^6$ cells to about 5 µg/$10^6$ cells. More in particular, such dosages may prevent or reduce HBV-related symptoms at least 50% compared to pre-treatment symptoms or compared to a suitable control. Treatment with at least one retroviral vector according to the present invention may palliate or alleviate HBV infection and/or at least one associated condition, and/or may reduce incidence of progression to chronic HBV-associated conditions, without providing a cure. In particular, treatment may be used to cure or prevent an acute or chronic HBV infection or an associated condition, including hepatocellular carcinoma.

In particular, the quantity of cells that make up the immunotherapeutically effective amount of cells to be administered depends on the subject to be treated. This may be dependent on but not limited to, the capacity of the individual's immune system to mount TCR-mediated immune response, the age, sex and weight of the patient and the severity of the condition being treated. The number of variables in regard to at least one individual's prophylactic or treatment regimen may be large, and a considerable range of doses may be expected. In particular, cells may be administered in at least one amount from $5 \times 10^5$ cells/kg body weight to $1 \times 10^{10}$ cells/kg body weight. More in particular, $5 \times 10^6$ cells/kg body weight to $1 \times 10^8$ cells/kg body weight may be administered. The maximal dosage of cells and/or viral vector to be administered to the subject may be the highest dosage that does not cause undesirable and/or intolerable side effects. Suitable regimens for initial administration and additional treatments may also be contemplated and may be determined according to conventional protocols.

According to another aspect, the present invention provides at least one use of at least one cell, at least one vector according and/or at least one polypeptide according to any aspect of the present invention in the preparation of a medicament for treating HBV infection and/or HBV-related hepatocellular carcinoma.

Suitable solid or liquid medicament preparation forms may be, for example, granules, powders, tablets, coated tablets, (micro) capsules, suppositories, syrups, emulsions, suspensions, creams, aerosols, drops or injectable solutions in ampule form and also preparations with protracted release of active compounds, in whose preparation excipients and additives and/or auxiliaries such as disintegrants, binders, coating agents, swelling agents, lubricants, flavourings, sweeteners or solubilizers are customarily used as described above. The medicaments may be suitable for use in a variety of drug delivery systems.

According to one aspect, the present invention provides at least one in vitro method for diagnosing at least one subject that is able to resolve HBV infection, the method comprising:
(a) providing at least one sample from at least one subject;
(b) detecting the presence of at least one polynucleotide comprising, substantially consisting of or consisting of at least one nucleic acid sequence selected from SEQ ID NO: 4, SEQ ID NO: 8, SEQ ID NO: 16 and SEQ ID NO: 20, SEQ ID NO: 43, SEQ ID NO: 51, a homologue and/or a fragment thereof; and/or
(c) detecting the presence of at least one polypeptide comprising, substantially consisting of or consisting of the amino acid sequence of SEQ ID NO: 12, SEQ ID NO: 24, SEQ ID NO: 47, SEQ ID NO: 55, a homologue and/or a fragment thereof;
wherein the presence of the polynucleotide and/or the polypeptide is indicative of the subject being able to resolve the HBV infection.

According to yet another aspect, the present invention provides at least one in vitro method for diagnosing at least one subject as having or as being at risk of having HBV infections and/or HBV related hepatocellular carcinoma, the method comprising:
(a) providing at least one sample from at least one subject;
(b) detecting the presence of at least one polynucleotide comprising, substantially consisting of or consisting of at least one nucleic acid sequence selected from SEQ ID NO: 4, SEQ ID NO: 8, SEQ ID NO: 16 and SEQ ID NO: 20, SEQ ID NO: 43, SEQ ID NO: 51, a homologue and/or a fragment thereof; and/or
(c) detecting the presence of at least one polypeptide comprising, substantially consisting of or consisting of the amino acid sequence of SEQ ID NO: 12, SEQ ID NO: 24, SEQ ID NO: 47, SEQ ID NO: 55, a homologue and/or a fragment thereof;
wherein the absence of the polynucleotide and/or the polypeptide correlates with the likelihood of the subject as having or as being at risk for having HBV-infection and/or HBV-related hepatocellular carcinoma.

In particular, the test sample may be urine, blood, serum, sweat, and/or oral fluid samples. More in particular, the presence of at least one polynucleotide and/or polypeptide of the present invention may be determined using several methods known in the art. Some of the methods may comprise, but are not limited to, real time PCR, flow cytometry, PCR and/or geometric mean fluorescence intensity (MFI).

According to still another aspect, the present invention provides at least one kit for detecting and/or treatment of HBV infection and/or HBV-related hepatocellular carcinoma, the kit comprising at least one cell, at least one vector and/or at least one polypeptide according to any aspect of the present invention. In particular, the kit may comprise at least one manual providing instruction on how to use the kit.

TABLE 1

Sequences of HBV eptiope reactive exogenous TCR alpha 3 and beta 8 chains and naturally occurring HBc 18-27 epitope mutant peptides.

| Name | Sequence | SEQ ID NO: |
|---|---|---|
| CDR1 alpha 3 (WT) | AAAACTAGTATAAACAATTTA | 1 |
| CDR2 alpha 3 (WT) | TTAATACGTTCAAATGAAAGAGAG | 2 |
| CDR3 alpha 3 (WT) | TGTGCTACGTGGCTCTCTGGTTCTGCAAGGCAACTGACCTTT | 3 |
| TCR alpha 3 (WT) | ATGGAAACTCTCCTGGGAGTGTCTTTGGTGATTCTATGGCTT CAACTGGCTAGGGTGAACAGTCAACAGGGAGAAGAGGATCCT CAGGCCTTGAGCATCCAGGAGGGTGAAAATGCCACCATGAAC TGCAGTTACAAAACTAGTATAAACAATTTACAGTGGTATAGA CAAAATTCAGGTAGAGGCCTTGTCCACCTAATTTTAATACGT TCAAATGAAAGAGAGAAACACAGTGGAAGATTAAGAGTCACG CTTGACACTTCCAAGAAAAGCAGTTCCTTGTTGATCACGGCT TCCCGGGCAGCAGACACTGCTTCTTACTTCTGTGCTACGTGG CTCTCTGGTTCTGCAAGGCAACTGACCTTTGGATCTGGGACA CAATTGACTGTTTTACCTGATATCCAGAACCCTGACCCTGCC GTGTACCAGCTGAGAGACTCTAAATCCAGTGACAAGTCTGTC TGCCTATTCACCGATTTTGATTCTCAAACAAATGTGTCACAA AGTAAGGATTCTGATGTGTATATCACAGACAAAACTGTGCTA GACATGAGGTCTATGGACTTCAAGAGCAACAGTGCTGTGGCC TGGAGCAACAAATCTGACTTTGCATGTGCAAACGCCTTCAAC AACAGCATTATTCCAGAAGACACCTTCTTCCCCAGCCCAGAA AGTTCCTGTGATGTCAAGCTGGTCGAGAAAAGCTTTGAAACA GATACGAACCTAAACTTTCAAAACCTGTCAGTGATTGGGTTC CGAATCCTCCTCCTGAAAGTGGCCGGGTTTAATCTGCTCATG ACGCTGCGGCTGTGGTCCAGCTGA | 4 |
| CDR1 alpha 3 (OPT) | AAGACATCAATCAACAACTTG | 5 |
| CDR2 alpha 3 (OPT) | CTGATTCGGAGTAATGAGCGGAA | 6 |
| CDR3 alpha 3 (OPT) | TGTGCTACATGGCTGAGTGGCAGCGCACGGCAATTGACTTTT | 7 |

TABLE 1-continued

Sequences of HBV epitope reactive exogenous TCR alpha 3 and beta 8 chains and naturally occurring HBc 18-27 epitope mutant peptides.

| Name | Sequence | SEQ ID NO: |
|---|---|---|
| TCR alpha 3 (OPT) | ATGGAGACCCTTCTGGGAGTGTCCCTCGTGATTCTGTGGCTG CAGCTTGCTCGGGTGAATTCTCAGCAGGGCGAGGAAGACCCG CAGGCCCTTAGCATTCAGGAAGGGGAGAACGCTACCATGAAT TGCTCATACAAGACATCAATCAACAACTTGCAGTGGTACCGT CAGAACTCTGGGAGAGGACTCGTGCACCTGATCCTGATTCGG AGTAATGAGCGGGAAAAACACTCTGGAAGGCTGAGGGTGACC CTCGATACCTCTAAAAAATCCTCCTCCCTGCTGATAACCGCC AGCAGGGCCGCCGACACCGCTTCCTACTTCTGTGCTACATGG CTGAGTGGCAGCGCACGGCAATTGACTTTTGGGAGTGGCACT CAGCTGACAGTGCTGCCCGACATCCAGAATCCAGATCCCGCA GTGTATCAGCTGAGAGACTCAAAGTCAAGTGACAAGAGTGTG TGCCTGTTCACTGATTTTGACTCTCAGACCAACGTCTCTCAG TCTAAGGACAGCGACGTTTACATCACTGACAAAACTGTGCTG GACATGCGCAGTATGGACTTTAAATCAAATTCCGCCGTGGCT TGGAGCAATAAGTCTGACTTCGCCTGTGCTAATGCTTTTAAT AACTCCATCATTCCGGAGGATACATTTTTCCCTAGCCCCGAG TCATCCTGCGACGTGAAGCTGGTGGAGAAGTCATTCGAGACC GACACCAATCTTAACTTTCAGAACCTGTCCGTTATCGGGTTT AGAATCCTGCTGCTGAAGGTTGCCGGATTCAACCTGCTTATG ACGTTGCGCCTGTGGTCCAGCTGA | 8 |
| CDR1 alpha 3 | KTSINNL | 9 |
| CDR2 alpha 3 | LIRSNERE | 10 |
| CDR3 alpha 3 | CATWLSGSARQLTF | 11 |
| TCR alpha 3 | METLLGVSLVILWLQLARVNSQQGEEDPQALSIQEGENATMN CSYKTSINNLQWYRQNSGRGLVHLILIRSNEREKHSGRLRVT LDTSKKSSSLLITASRAADTASYFCATWLSGSARQLTFGSGT QLTVLPDIQNPDPAVYQLRDSKSSDKSVCLFTDFDSQTNVSQ SKDSDVYITDKTVDMRSMDFKSNSAVAWSNKSDFACANALFN NSIIPEDTFFPSPESSCDVKLVEKSFETDTNLNFQNLSVIGF RILLLKVAGFNLLMTLRLWSS. | 12 |
| CDR1 beta 8 (WT) | ATT TCA GGA CAC GAC TAC CTT | 13 |
| CDR2 beta 8 (WT) | TAC TTT AAC AAC AAC GTT CCG ATA | 14 |
| CDR3 beta 8 (WT) | TGT GCC AGC AGC AAT CGG GCG AGC TCC TAC AAT GAG CAG TTC TTC | 15 |
| TCR beta 8 (WT) | ATGGACTCCTGGACCCTCTGCTGTGTGTCCCTTTGCATCCTG GTAGCAAAGCACACAGATGCTGGAGTTATCCAATCACCCCGG CACGAGGTGACAGAGATGGGACAAGAAGTGACTCTGAGATGT AAACCAATTTCAGGACACGACTACCTTTTCTGGTACAGACAG ACCATGATGCGGGGACTGGAGTTGCTCATTTACTTTAACAAC AACGTTCCGATAGATGATTCAGGGATGCCCGAGGATCGATTC TCAGCTAAGATGCCTAATGCATCATTCTCCACTCTGAAGATC CAGCCCTCAGAACCCAGGGACTCAGCTGTGTACTTCTGTGCC AGCAGCAATCGGGCGAGCTCCTACAATGAGCAGTTCTTCGGG CCAGGGACACGGCTCACCGTGCTAGAGGACCTGAAAAACGTG TTCCCACCCGAGGTCGCTGTGTTTGAGCCATCAGAAGCAGAG ATCTCCCACACCCAAAAGGCCACACTGGTGTGCCTGGCCACA GGCTTCTACCCCGACCACGTGGAGCTGAGCTGGTGGGTGAAT GGGAAGGAGGTGCACAGTGGGGTCAGCACAGACCCGCAGCCC CTCAAGGAGCAGCCCGCCCTCAATGACTCCAGATACTGCCTG AGCAGCCGCCTGAGGGTCTCGGCCACCTTCTGGCAGAACCCC CGCAACCACTTCCGCTGTCAAGTCCAGTTCTACGGGCTCTCG GAGAATGACGAGTGGACCCAGGATAGGGCAAACCTGTCACC CAGATCGTCAGCGCCGAGGCCTGGGGTAGAGCAGACTGTGGC TTCACCTCCGAGTCTTACCAGCAAGGGGTCCTGTCTGCCACC ATCCTCTATGAGATCTTGCTAGGGAAGGCCACCTTGTATGCC GTGCTGGTCAGTGCCCTCGTGCTGATGGCCATGGTCAAGAGA AAGGATTCCAGAGGCTAG | 16 |
| CDR1 beta 8 (OPT) | ATC TCT GGG CAC GAC TAC CTG | 17 |
| CDR2 beta 8 (OPT) | TAT TTT AAT AAC AAT GTG CCT ATC | 18 |
| CDR3 beta 8 (OPT) | TGT GCC TCC TCC AAC CGG GCC TCC TCT TAT AAC GAG CAG TTC TTC | 19 |

TABLE 1-continued

Sequences of HBV eptiope reactive exogenous TCR alpha 3 and beta 8 chains and naturally occurring HBc 18-27 epitope mutant peptides.

| Name | Sequence | SEQ ID NO: |
|---|---|---|
| TCR beta 8 (OPT) | ATGGACAGCTGGACACTGTGCTGCGTGAGCCTGTGCATTCTG GTGGCCAAGCACACCGACGCCGGCGTGATCCAGAGCCCTCGC CACGAGGTGACCGAAATGGGCCAGGAGGTGACACTGCGCTGC AAGCCAATCTCTGGGCACGACTACCTGTTCTGGTACAGGCAG ACCATGATGAGGGGCCTGGAACTGCTGATCTATTTTAATAAC AATGTGCCTATCGATGACTCTGGCATGCCCGAGGACAGGTTC TCCGCCAAGATGCCCAACCCAGCTTCTCCACCCTGAAGGATC CAGCCCTCCGAACCTAGGGACTCCGCCGTGTACTTCTGTGCC TCCTCCAACCGGGCCTCCTCTTATAACGAGCAGTTCTTCGGC CCTGGAACCCGCCTGACCGTGCTGGAGGACCTGAAAAATGTG TTTCCCCCCGAGGTGGCCGTGTTTGAACCAAGCGAGGCCGAG ATCAGCCACACACAGAAGGCCACCCTGGTGTGTCTGGCCACC GGATTCTATCCCGATCACGTGGAGCTGAGCTGGTGGGTGAAC GGGAAGGAGGTGCACTCTGGCGTGAGCACCGACCCTCAGCCA CTGAAAGAGCAGCCCGCCCTGAATGATTCTCGGTACTGCCTG TCCAGCCGCCTGCGCGTGTCTGCCACCTTCTGGCAGAACCCC AGAAATCACTTCAGGTGCCAGGTGCAGTTCTATGGGCTGAGC GAGAACGACGAATGGACCCAGGACAGAGCCAAGCCTGTGACA CAGATCGTGTCTGCCGAAGCCTGGGGCAGAGCCGACTGCGGC TTTACCAGCGAGAGCTACCAGCAGGGCGTGCTGTCCGCCACA ATTCTGTACGAGATCCTGCTGGGAAAGGCCACACTGTACGCC GTGCTGGTGAGCGCCCTGGTGCTGATGGCCATGGTGAAGCGG AAAGACTCCCGGGGCTGA | 20 |
| CDR1 beta 8 | ISGHDYL | 21 |
| CDR2 beta 8 | YFNNNVPI | 22 |
| CDR3 beta 8 | CASSNRASSYNEQFF | 23 |
| TCR beta 8 | MDSWTLCCVSLCILVAKHTDAGVIQSPRHEVTEMGQEVTLRC KPISGHDYLFWYRQTMMRGLELLIYFNNNVPIDDSGMPEDRF SAKMPNASFSTLKIQPSEPRDSAVYFCASSNRASSYNEQFFG PGTRLTVLEDLKNVFPPEVAVFEPSEAEISHTQKATLVCLAT GFYPDHVELSWWVNGKEVHSGVSTDPQPLKEQPALNDSRYCL SSRLRVSATFWQNPRNHFRCQVQFYGLSENDEWTQDRAKPVT QIVSAEAWGRADCGFTSESYQQGVLSATILYEILLGKATLYA VLVSALVLMAMVKRKDSRG | 24 |
| HBc18-27 peptide (HBV genotype A/D/E/F) (WT C18-27) | FLPSDFFPSV | 25 |
| HBc18-27 peptide (HBV genotype B/C)(27I) | FLPSDFFPSI | 26 |
| Natural Variant 1 | FLPNDFFPSV | 27 |
| Natural Variant 2 | FLPNDFFPSA | 28 |
| Natural Variant 3 | FLPADFFPSI | 29 |
| Natural Variant 4 | FLPVDFFPSI | 30 |
| Natural Variant 5 | FLPTDYFPSV | 31 |
| Natural Variant 6 | FLPSDFYPPV | 32 |
| Natural Variant 7 (26G) | FLPSDFFPGV | 33 |
| Natural Variant 8 (25M, 26G) | FLPSDFFMGV | 34 |
| Natural Variant 9 (23Y) | FLPSDYFPSV | 35 |
| Natural Variant 10 (24L) | FLPSDFLPSV | 36 |
| Natural Variant 11 (21P) | FLPPDFFPSV | 37 |
| Natural Variant 12 (27A) | FLPSDFFPSA | 38 |
| Natural Variant 13 (24Y) | FLPSDFYPSV | 39 |

TABLE 2

Sequences of HBV epitope reactive exogenous TCR alpha 12 and beta 7.8 chains and naturally occurring HBe 370-79 epitope mutant peptides.

| Name | Sequence | SEQ ID NO: |
|---|---|---|
| CDR1 alpha 12 (WT) | GAC CGA GGT TCC CAG TCC | 40 |
| CDR2 alpha 12 (WT) | ATA TAC TCC AAT GGT | 41 |
| CDR3 alpha 12 (WT) | TGT GCC GTG AAC CTC TAT GCA GGC AAC ATG CTC ACC TTT | 42 |
| TCR alpha 12 (WT) | ATGATGAAATCCTTGAGAGTTTTACTAGTGATCCTGTGGCTT CAGTTGAGCTGGGTTTGGAGCCAACAGAAGGAGGTGGAGCAG AATTCTGGACCCCTCAGTGTTCCAGAGGGAGCCATTGCCTCT CTCAACTGCACTTACAGTGACCGAGGTTCCCAGTCCTTCTTC TGGTACAGACAATATTCTGGGAAAAGCCCTGAGTTGATAATG TTCATATACTCCAATGGTGACAAAGAAGATGGAAGGTTTACA GCACAGCTCAATAAAGCCAGCCAGTATGTTTCTCTGCTCATC AGAGACTCCCAGCCCAGTGATTCAGCCACCTACCTCTGTGCC GTGAACCTCATGCAGGCAACATGCTCACCTTTGGAGTGGGGA ACAAGGTTAATGGTCAAACCCCATATCCAGAACCCTGACCCT GCCGTGTACCAGCTGAGAGACTCTAAATCCAGTGACAAGTCT GTCTGCCTATTCACCGATTTTGATTCTCAAACAAATGTGTCA CAAAGTAAGGATTCTGATGTGTATATCACAGACAAAACTGTG CTAGACATGAGGTCTATGGACTTCAAGAGCAACAGTGCTGTG GCCTGGAGCAACAAATCTGACTTTGCATGTGCAAACGCCTTC AACAACAGCATTATTCCAGAAGACACCTTCTTCCCCAGCCCA GAAAGTTCCTGTGATGTCAAGCTGGTCGAGAAAAGCTTTGAA ACAGATACGAACCTAAACTTTCAAAACCTGTCAGTGATTGGG TTCCGAATCCTCCTCCTGAAAGTGGCCGGGTTTAATCTGCTC ATGACGCTGCGGCTGTGGTCCAGCTGA | 43 |
| CDR1 alpha 12 | DRGSQS | 44 |
| CDR2 alpha 12 | IYSNG | 45 |
| CDR3 alpha 12 | CAVNLYAGNMLTF | 46 |
| TCR alpha 12 | MMKSLRVLLVILWLQLSWVWSQQKEVEQNSGPLSVPEGAIAS LNCTYSDRGSQSFFWYRQYSGKSPELIMFIYSNGDKEDGRFT AQLNKASQYVSLLIRDSQPSDSATYLCAVNLYAGNMLTFGGG TRLMVKPHIQNPDPAVYQLRDSKSSDKSVCLFTDFDSQTNVS QSKDSDVYITDKTVLDMRSMDFKSNSAVAWSNKSDFACANAF NNSIIPEDTFFPSPESSCDVKLVEKSFETDTNLNFQNLSVIG FRILLLKVAGFNLLMTLRLWSS | 47 |
| CDR1 beta 7.8 (WT) | TCG GGT CAT GTA TCC | 48 |
| CDR2 beta 7.8 (WT) | TTC CAG AAT GAA GCT CAA | 49 |
| CDR3 beta 7.8 (WT) | TGT GCC AGC AGC TCG GAC TTT GGC AAT CAG CCC CAG CAT TTT | 50 |
| TCR beta 7.8 (WT) | ATGGGCACCAGGCTCCTCTGCTGGGTGGTCCTGGGTTTCCTA GGGACAGATCACACAGGTGCTGGAGTCTCCCAGTCCCCTAGG TACAAAGTCGCAAAGAGAGGACAGGATGTAGCTCTCAGGTGT GATCCAATTTCGGGTCATGTATCCCTTTTTTGGTACCAACAG GCCCTGGGCAGGGGCCAGAGTTTCTGACTTATTTCCAGAAT GAAGCTCAACTAGACAAATCGGGGCTGCCCAGTGATCGCTTC TTTGCAGAAAGGCCTGAGGGATCCGTCTCCACTCTGAAGATC CAGCGCACACAGCAGGAGGACTCCGCCGTGTATCTCTGTGCC AGCAGCTCGGACTTTGGCAATCAGCCCCAGCATTTTGGTGAT GGGACTCGACTCTCCATCCTAGAGGACCTGAACAAGGTGTTC CCACCCGAGGTCGCTGTGTTTGAGCCATCAGAAGCAGAGATC TCCCACACCCAAAAGGCCACACTGGTGTGCCTGGCCACAGGC TTCTTCCCTGACCACGTGGAGCTGAGCTGGTGGGTGAATGGG AAGGAGGTGCACAGTGGGGTCAGCACGGACCCGCAGCCCCTC AAGGAGCAGCCCGCCCTCAATGACTCCAGATACTGCCTGAGC AGCCGCCTGAGGGTCTCGGCCACCTTCTGGCAGAACCCCCGC AACCACTTCCGCTGTCAAGTCCAGTTCTACGGGCTCTCGGAG AATGACGAGTGGACCCAGGATAGGGCCAAACCCGTCACCCAG ATCGTCAGCGCCGAGGCCTGGGGTAGAGCAGACTGTGGCTTT ACCTCGGTGTCCTACCAGCAAGGGGTCCTGTCTGCCACCATC CTCTATGAGATCCTGCTAGGGAAGGCCACCCTGTATGCTGTG CTGGTCAGCGCCCTTGTGTTGATGGCCATGGTCAAGAGAAAG GATTTCTGA | 51 |

TABLE 2-continued

Sequences of HBV eptiope reactive exogenous TCR alpha 12 and beta 7.8 chains and naturally occurring HBe 370-79 epitope mutant peptides.

| Name | Sequence | SEQ ID NO: |
|---|---|---|
| CDR1 beta 7.8 | SGHVS | 52 |
| CDR2 beta 7.8 | FQNEAQ | 53 |
| CDR3 beta 7.8 | CASSSDFGNQPQHF | 54 |
| TCR beta 7.8 | MGTRLLCWVVLGFLGTDHTGAGVSQSPRYKVAKRGQDVALRC DPISGHVSLFWYQQALGQGPEFLTYFQNEAQLDKSGLPSDRF FAERPEGSVSTLKIQRTQQEDSAVYLCASSSDFGNQPQHFGD GTRLSILEDLNKVFPPEVAVFEPSEAEISHTQKATLVCLATG FFPDHVELSWWVNGKEVHSGVSTDPQPLKEQPALNDSRYCLS SRLRVSATFWQNPRNHFRCQVQFYGLSENDEWTQDRAKPVTQ IVSAEAWGRADCGFTSVSYQQGVLSATILYEILLGKATLYAV LVSALVLMAMVKRKDF | 55 |
| HBs370-79 peptide (HBV genotype A/D) | SIVSPFIPLL | 56 |
| HBs370-79 peptide (HBV genotype B) | NILSPFMPLL | 57 |
| HBs370-79 peptide (HBV genotype C) | NILNPFLPLL | 58 |

Having now generally described the invention, the same will be more readily understood through reference to the following examples which are provided by way of illustration, and are not intended to be limiting of the present invention.

EXAMPLES

Standard molecular biology techniques known in the art and not specifically described were generally followed as described in Sambrook and Russel, Molecular Cloning: A Laboratory Manual, Cold Springs Harbor Laboratory, New York (2001).

The following examples are provided to assist in a further understanding of the invention. The particular materials and conditions employed are intended to be further illustrative of the invention and are not limiting upon the reasonable scope of the appended claims.

Example 1

Cloning Hepatitis B Virus Specific T Cell Specific for HBV Core 18-27 Epitope (HBc18-27)

Peripheral blood lymphocytes (PBL) were isolated from fresh blood obtained from a HBV patient who was able to resolve the disease and who was of HLA haplotype HLA-A0201 herein referred to as "a resolved HLA-A201 HBV patient".

The blood was first heparinised and PBL were isolated using Ficoll-Paque density gradient centrifugation. PBL were then washed three times in Hanks Balanced Salt Solution (HBSS) (Invitrogen, Carlsbad, Calif.), resuspended in Aim-V medium, 2% human AB serum (Invitrogen, Carlsbad, Calif.), stimulated with 1 µM of HBV core 18-27 epitope ("HBc18-27 peptide"; FLPSDFFPSV; SEQ ID NO: 25; Primm SRL, Milano, Italy) plus 20 U/ml interleukin-2-(R&D systems, Minneapolis, Minn.) and plated in a 24-well plate at $4 \times 10^6$ cells/well for 10 days.

Figure 2:
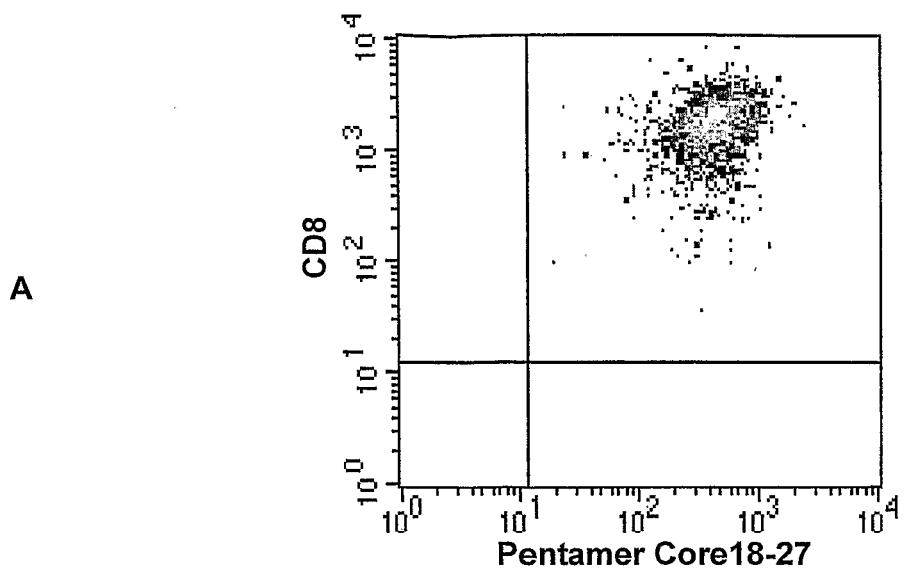
FIG. 2 (A) depicts FACS analysis of peripheral blood lymphocytes (PBL) which were stimulated with HBc18-27 peptide to generate T cell lines. The HBc18-27 specific T cell line was isolated using specific HBc18-27-HLA-A201 pentamers and magnetic separation. The isolated HBc18-27 specific T cell line was stained with HBc18-27-HLA-A201 specific pentamers to confirm clonality. The results show that 100% of the T cells were CD8+ and HLA-A2 pentamer positive, indicating clonality.
Figure 2:
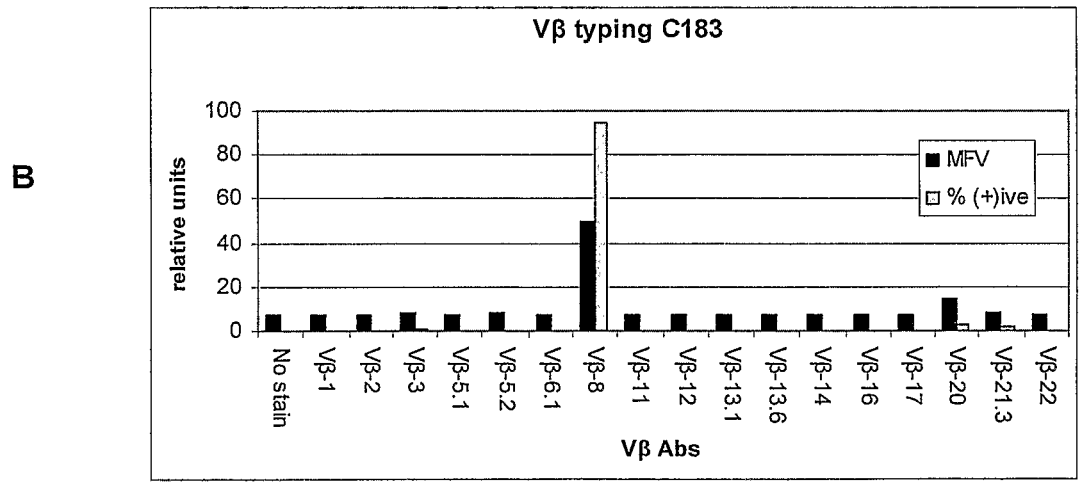

The HBc18-27-specific CD8+ T cells prepared as above were then labelled with phycoerythrin (PE)-conjugated HLA-A2 class I pentamers herein referred to as "HBc18-27-HLA-A201 pentamers" and/or "HLA-A2 pentamer" (Proimmune, Oxford, United Kingdom) bearing the HBc18-27 epitope for 30 min at 37° C. and purified via magnetic cell sorting using anti-PE microbeads (Miltenyi Biotech, Surrey, United Kingdom). Following isolation, cells were labelled with Cy-chrome-conjugated anti-CD8+ (BD Pharmingen, San Diego, Calif.) and the percentage of stained T cells were determined by Fluorescence-activated cell sorting (FACS) analysis using a FACScan flow cytometer (BD Biosciences, SanDiego, Calif.) and analyzed using CellQuest software (BD Biosciences). The flow cytometry method used is further described in Gehring et al., incorporated herein by reference. The results are shown in FIG. 2A.

The CD8+ and HBc18-HLA-A201 pentamer positive T cells as mentioned above, were then cloned using the limiting dilution assay as described in "Current Protocols in Immunology" Copyright © 2007 by John Wiley and Sons, Inc., and expanded in Aim-V 2% AB serum (Invitrogen, Carlsbad, Calif.), 20 U/ml IL-2, 10 ng/ml IL-7, and 10 ng/ml IL-15 (R&D systems, Minneapolis, Minn.) with 1.5 µg/ml phytohemagglutinin (Sigma-Aldrich, Dorset, United Kingdom) using allogeneic irradiated PBL as feeder cells. Cells were plated at 1 cell/well on 96 well plates and wells positive for T cell growth were tested for HBc18-27 reactivity by intracellular cytokine staining for IFN-γ according to the protocol provided in Gehring et al., incorporated herein by reference.

Highly positive wells for peptide reactivity were then screened using the specific HBc18-27 HLA-A201 pentamer (Proimmune, Oxford, United Kingdom) and a T cell clone, referred to herein as C183 was selected for further study. The results, depicted in FIG. 2A, demonstrate that 100% of CD8+ and HBc18-27-HLA-A201 pentamer-reactive T cells were detected. Clonality was tested using a panel of T cell receptor (TCR) Vβ monoclonal antibodies (Beckman Coulter, Fullerton, Calif.). This procedure involved the use of a panel of Vβ antibodies that stained all known Vβ chain family members and where positive staining for only one Vβ chain meant that it was highly likely that all of the T cells of that clone expressed the same TCR. Accordingly, the resultant TCR Vβ distribution for C183, shown in FIG. 2B demonstrates that all the T cells from C183 were Vβ8 positive suggesting homogeneity (likely that they were all derived from a single cell) and thus clonality.

C183 thus was shown to be a clonal, CD8+, HBc18-27 specific cytotoxic T cell clone and was grown and maintained in Aim-V, 2% AB serum, 20 U/ml IL-2, 10 ng/ml IL-7, and 10 ng/ml IL-15 (R&D Systems, Abingdon, United Kingdom) in a 5% $CO_2$ humidified incubator at 37° C.

Example 2

Recognition of Tumor Cells and Primary Human Hepatocytes by C183 T Cell Clone

HepG2 is a HLA-A2+, hepatocyte-like tumor cell line isolated from a primary hepatocellular carcinoma tumor (HCC). HepG2 cells (American Type Culture Collection, Rockford, Md.) were grown and maintained in RPMI 1640 supplemented with 10% heat-inactivated fetal bovine serum (FBS), 20 mM HEPES, 0.5 mM sodium pyruvate, 100 U/ml penicillin, 100 μg/ml streptomycin, MeM amino acids, L-glutamine, MeM nonessential amino acids (Invitrogen, Carlsbad, Calif.), and 5 μg/ml Plasmocin (InvivoGen, San Diego, Calif.) to prevent mycoplasma contamination. A derivative of this line, HepG2.105 (Kindly provided by Michael Nassal at the University of Freiberg) was engineered to express the entire HBV genome under the control of a doxycycline dependent regulator, which permits viral antigen to be expressed at various levels as described in Sun and Nassal, 2006. A vector control parental cell line, HepG2TA2-7 (Kindly provided by Michael Nassal at the University of Freiberg) was stably transfected with the doxycycline dependent regulator but not the HBV genome. Both cell lines HepG2.105 and HepG2TA2-7, were grown in Dulbecco's modified Eagle's medium supplemented with 10% tetracycline-approved FBS (BD Biosciences, San Diego, Calif.), 20 mM HEPES, 0.5 mM sodium pyruvate, 100 U/ml penicillin, 100 μg/ml streptomycin, MeM nonessential amino acids (Invitrogen), 200 μg/ml G418 sulfate, 80 μg/ml Hygromycin B (AutogenBioclear, Wiltshire, United Kingdom). Doxycycline (0.1 to 100 ng/ml, BD Biosciences) was added to cultures to regulate HBV expression.

Figure 3:
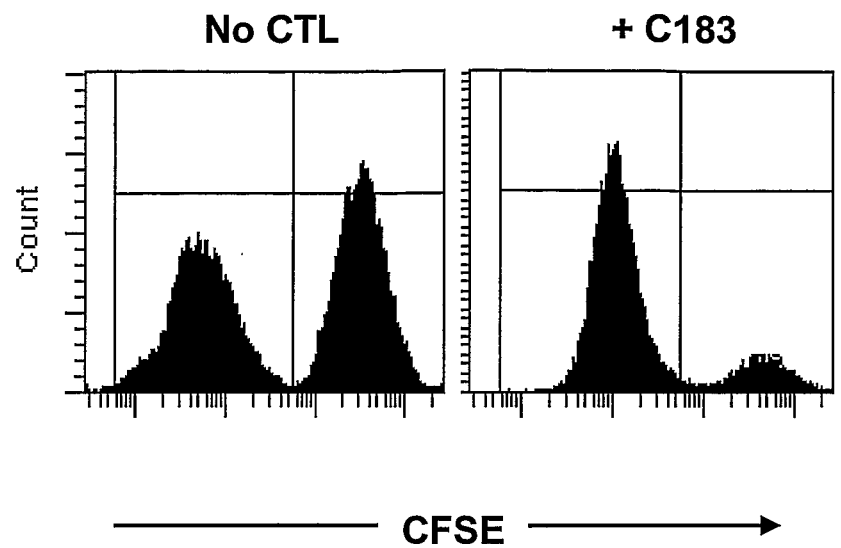
FIG. 3 shows the cytotoxic function of HBc18-27 specific Cytotoxic T lymphocyte (CTL) clone C183. CarboxyFluoroscein Succinimidyl Ester (CFSE) labelled HepG2 cells pulsed with HBc18-27 (8-10 M) epitope were mixed with HepG2 cells that were not HBc18-27 pulsed. The HepG2 cells were cultured in the presence or absence of CTL clones at a 1:1 ratio for 5 h. Cytotoxicity was determined by disappearance of CFSE labelled targets in the presence of C183 clone (+C183). After 5 h co-incubation, the results show that only CFSE negative cells (no HBc18-27 peptide) remained and nearly all HBc18-27 positive, CFSE positive HepG2 cells were eliminated by C183, indicating the T cell clone is capable of killing tumour cells presenting HBV antigens like HBc18-27. There was no significant difference in the cell count when no CTL was added (NO CTL).

The standard HepG2 cells were labeled with 0.75 μM carboxyfluorescein succinimidyl ester (CFSE; Invitrogen) for 10 min at 37° C. Cells were washed, and CFSE-labelled targets were pulsed with $10^{-8}$ M HBc18-27 peptide (Primm SRL, Milano, Italy) for 1 h on ice. Unlabelled (0 M HBc18-27 peptide) and CFSE-labelled (plus HBc18-27 peptide) HepG2 cells were mixed together in a 1:1 ratio, $2\times10^5$ cells of each HepG2 cell line, in 24-well plates and incubated overnight to permit HepG2 adherence. To determine if C183 was capable of killing HCC tumor cells, C183 clones obtained from Example 1 were co-cultured with the HepG2 cells that were adhered to the wells ("targets"). A total of $4\times10^5$ of C183 clones were added to the targets and incubated for 5 h at 37° C. The resultant effector (C183):target (unlabelled+CFSE-labelled HepG2 cells) ratio was 1:1. After 5 h co-incubation, HepG2 cells were collected via trypsinization and cytotoxicity was determined by comparing ratio of peptide pulsed targets to unpulsed targets in wells +/- the addition of C183. The results shown in FIG. 3 depict that CFSE negative cells (no HBc18-27 peptide) which were co-cultured with C183 remained and nearly all HepG2 cells which were HBc18-27 and CFSE positive were eliminated by C183 as shown in the last column. The results indicate that the HBc18-27 specific cytotoxic T cell clone, C183 was capable of killing tumor cells presenting HBV peptides.

Further, to determine if C183 can recognize endogenously processed antigen presented by HCC cells, C183 was co-cultured with HepG2.105 or HepG2TA2-7 control line and then tested for cytokine production and cytotoxic degranulation (CD107a+ staining), an indirect measure of killing. $1\times10^5$ cells of each HepG2.105 and HepG2TA2-7 cell line were seeded separately into 96-well plates and incubated overnight to permit HepG2 adherence. For cytotoxic degranulation assays, CD107a-PE antibody (BD Pharmingen, San Diego) was first added to all wells before a total of $1\times10^5$ of C183 clones were added to each well with the adhered HepG2.105 or HepG2TA2-7 control line and incubated for 5 h at 37° C. The resultant effector (C183):target (HepG2.105 or HepG2TA2-7 control line) ratio was 1:1. Following the incubation, C183 T cells were harvested, washed and stained with Cy-chrome conjugated anti-CD8+ (BD Pharmingen, San Diego, Calif.) then permeabilized and fixed using Cytofix/Cytoperm (BD Pharmingen, San Diego) according to the manufacturer's instructions. Cells were washed and incubated with PE-conjugated anti-human IFN-γ antibody (R&D systems) for 30 min on ice then washed and analyzed by flow cytometry using the FACScan flow cytometer (BD Biosciences, SanDiego, Calif.) and analyzed using CellQuest software (BD Biosciences). The flow cytometry method used is further described in Gehring et al. incorporated herein by reference.

Figure 4:
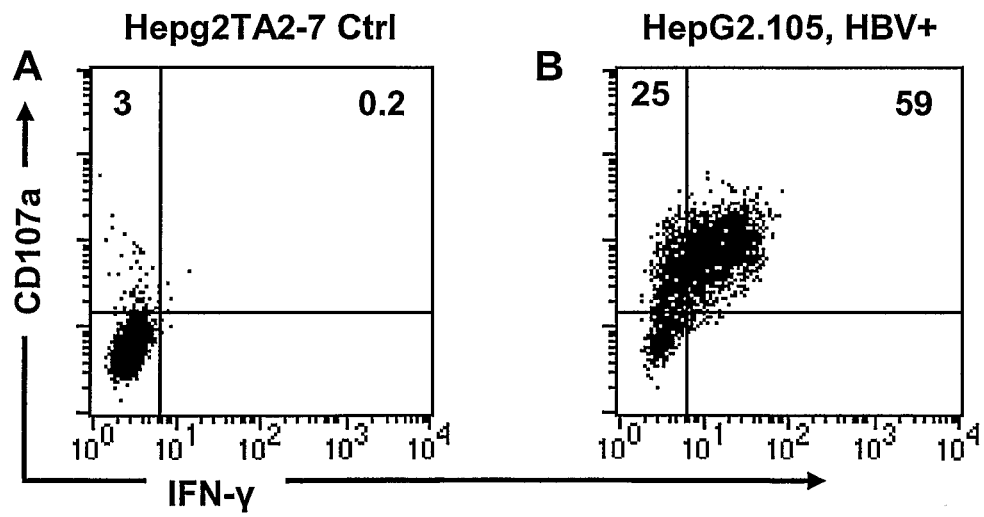
FIG. 4 shows that C183 T cell clone recognizes endogenously processed viral antigen presented by hepatocellular carcinoma cells.

As shown in FIG. 4A, C183 did not respond to the control cell line HepG2TA2-7 that was HBV negative. However, as shown in FIG. 4B, co-culture of C183 with HepG2.105 cells expressing HBV, stimulated IFN-γ production and degranulation, indicating that C183 clone recognized the HBc18-27 epitope endogenously processed and presented by hepatocellular carcinoma cells.

In order to determine if C183 T cell clone can respond to naturally infected hepatocytes, primary hepatocytes were isolated from HLA-A2+ or HLA-A2-explanted chronic HBV livers and co-cultured with C183 according to the procedure described below.

Liver tissue was obtained from both HLA-A2+ or HLA-A2-explanted chronic HBV patients under informed consent according to ethical and moral guidelines of the institution. Tissue sections were collected in William's E medium (Sigma-Aldrich, Dorset, United Kingdom) and maintained at 4° C. for a maximum of 2 h before cell isolation. Hepatocytes were isolated by enzyme perfusion described for use with human liver by Strain et al. (Strain, Ismail et al., 1991) with some modifications. Briefly, a section of liver of about 100 to 200 g was cut, and exposed vessels on a single surface were cannulated with 3-mm internal diameter tubing. The tissue was perfused sequentially at 50 ml/min with 500 ml PBS-HEPES wash solution to remove William's E medium, 500 ml PBS-HEPES-0.5 mM EGTA, and again with 500 ml PBS-HEPES wash solution (The solutions were obtained from Invitrogen Ltd.). Finally, 300 ml enzyme solution (0.05% collagenase (Roche, Indianapolis, Ind.), 0.012% hyaluronidase (Sigma, Dorset, United Kingdom), 0.025% Dispase II (Roche), 0.005% DNase (Roche) containing 5 mM $CaCl_2$), maintained at 41° C., was perfused with recirculation, and enzymatic digestion continued for 10 to 20 min until the liver was judged to be substantially softened. Tissue was mechanically dissociated in 200 ml Hanks' balanced salt solution (Invitrogen Ltd.) containing 10% FBS, 5 mM $CaCl_2$. The cell suspension was filtered through a 60-μm cell strainer and pelleted at 37×g for 10 min at 4° C. Cells were washed three times in Hanks' balanced salt solution, after which viability and yield were assessed. Purified hepatocytes were used immediately after isolation. 100,000 primary hepatocytes/well were added to 96 well plates and 75,000 C183 clones were added to respective wells for 5 h with anti-CD107a-PE antibody (BD Pharmingen, San Diego) for degranulation plus 10 µg/ml brefeldin A (Sigma-Aldrich). Following the incubation, T cells were harvested, washed and stained with Cychrome conjugated anti-CD8+ (BD Pharmingen, San Diego, Calif.) then permeabilized and fixed using Cytofix/Cytoperm (BD Pharmingen, San Diego) according to the manufacturer's instructions. Cells were washed and incubated with FITC-conjugated anti-human IFN-γ antibody (R&D systems, Abingdon, UK) for 30 min on ice then washed and analyzed by flow cytometry using the FACScan flow cytometer (BD Biosciences, SanDiego, Calif.) and analyzed using CellQuest software (BD Biosciences). The flow cytometry method used is further described in Gehring et al. incorporated herein by reference.

Figure 5:
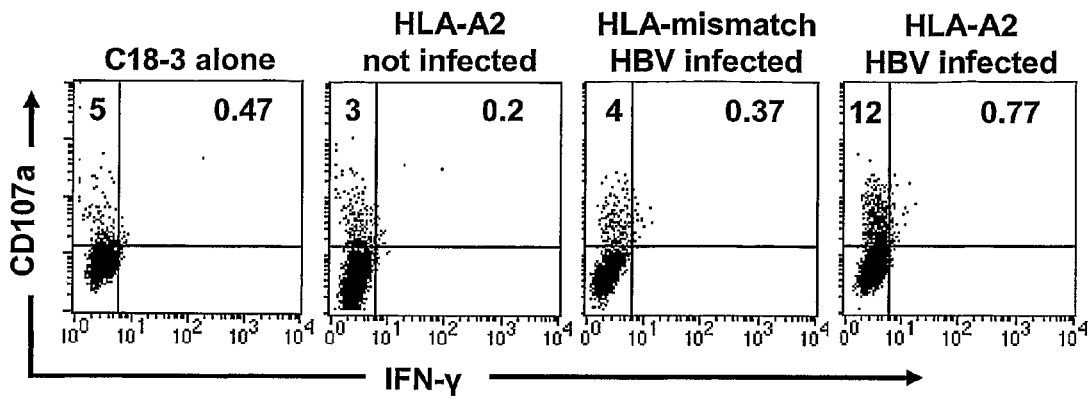
FIG. 5 shows the results of how C183 T cell clone responds to naturally infected hepatocytes. Primary hepatocytes which were isolated from HLA-A2+ or HLA-A2− explanted chronic HBV livers were co-cultured with C183. HBc18-27-specific C183 T cell clone degranulation and IFN-γ production was measured after incubation of C183 alone, with HLA-A2+ uninfected, with HLA-mismatch HBV infected or with HLA-A2+ HBV infected primary human hepatocytes. C183 activation (12% CD107a+) was only observed following incubation with HLA-A2+ HBV infected primary human hepatocytes indicating that the C183 T cell clone recognizes endogenously processed viral antigen presented by HBV infected primary hepatocytes that express the correct HLA molecules on their cell surface.

The results in FIG. 5 show that C183 discharged cytotoxic granules, measured by CD107a staining, in response to HLA-A2 positive HBV infected primary hepatocytes but not to HLA-A2 negative HBV infected hepatocytes or HLA-A2+ uninfected hepatocytes, indicating that the C183 can recognize naturally infected primary human hepatocytes.

Example 3

Recognition of Additional HLA-A2 Subtypes and Variant Peptides

Chronic HBV infection is predominantly an Asian problem and it is thus important to know if the HBc18-27 specific TCR can recognize HLA-A2 subtypes that dominate in the Asian population. HBV has a total of five genotypes (A, B, C, D and G). The HBc18-27 epitope expressed by HBV genotypes B and C (FLPSDFFPSI; SEQ ID NO:26) are the most prevalent in Asia. Genotypes A and D, most prevalent in Europe and United states, (FLPSDFFPSV; SEQ ID NO:25) are characterized by a valine at position 27 whereas genotypes B and C are characterized by an isoleucine at position 27. This can have a profound impact on the ability of HBV patients to present the HBc18-27 epitope or it can affect TCR recognition of the epitope.

The ability of C183 to recognize HBc18-27 epitope from genotypes B and C, and A and D presented by different subtypes of the HLA-A2 MHC class I family was determined using Epstein-Barr virus (EBV) transformed B cells with known subtypes of HLA-A2. (Kindly provided by Professor Chan Soh Ha at WHO Immunology and Training Research Centre, Singapore). EBV transformed B cells from any other source may be used in this procedure. The EBV transformed B cells ($10^5$ cells/well) were loaded with increasing concentrations (1 pM-1000 pM) of HBc18-27 peptide from either HBV genotypes A/D or HBV genotypes B/C for 1 h at 25° C. (HBV Genotype A/D=FLPSDFFPSV; Primm SRL; HBV genotype B/C=FLPSDFFPSI, Genscript, Piscataway, N.J.) EBV B cells were washed with HBSS to remove excess peptide and co-cultured with $7.5×10^4$ C183 for 5 h in the presence of 10 ug/ml brefeldin A. IFN-γ production was measured by intracellular cytokine staining to determine T cell activation as described in Gehring et al. incorporated herein by reference.

Figure 6:
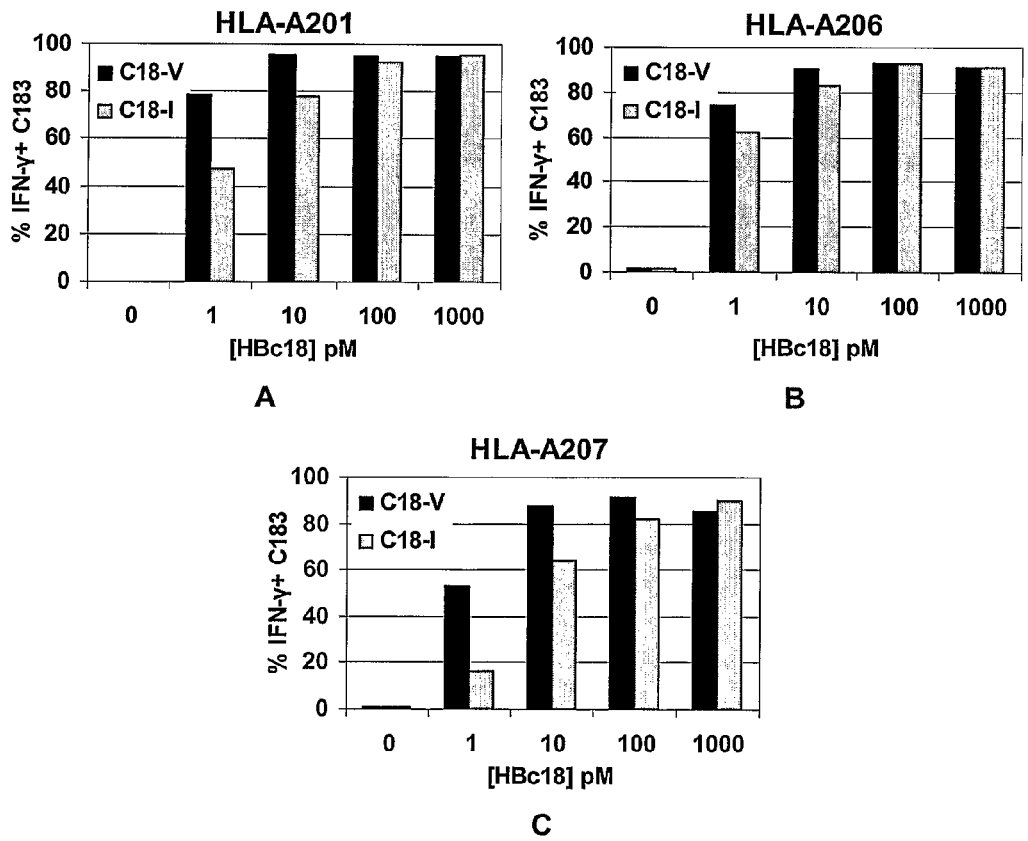
FIG. 6 shows the ability of T cell clone, C183, to recognize the HBc18-27 epitope from HBV genotypes B and C (grey bars, Asia virus; C18-I) and HBV genotypes A and D (black bars, European/American virus; C18-V) presented by different subtypes of the HLA-A2 MHC class I family. Epstein-Barr virus (EBV) transformed B cells with known subtypes of HLA-A2 were loaded with increasing concentrations of HBc18-27 epitope from different genotypes of HBV and co-cultured with C183 T cell clone for 5 h. IFN-γ production was measured to determine T cell activation. Data shows that (A) HLA-A201; (B) HLA-A206; and (C) HLA-A207 MHC class I molecules could present the HBV epitope from all genotypes and, were recognized by C183 and thus stimulated efficient IFN-γ production by the T cells. C183 T cell clone was found to be able to recognize the HBc18-27 epitope with high sensitivity (≤1 pM) from genotypes B and C or genotypes A and D and the epitope was recognized almost equally when presented by the three most dominant HLA-A2 subtypes A0201 (A), A0206 (B) and A0207 (C).

The results are shown in FIG. 6. The results show the ability of C183 to recognize the HBc18-27 epitope from four different HBV genotypes (A, B, C and D) and that the HBc18-27 epitopes were presented by the three most dominant HLA-A2 subtypes (HLA-A201, HLA-A206, and HLA-A207). The C183 T cell response is plotted at % IFN-γ+ cells. The black bars represent the frequency of IFN-γ+C183 T cells able to respond to the HBc18-27 epitope from HBV genotypes A/D (C18-V) whereas the grey bars represent the frequency of C183 T cells able to respond to HBc18-27 epitope from HBV genotypes B/C(C18-I) The data shows that HBc18-27 epitopes presented by (A) HLA-A201; (B) HLA-A206; and (C) HLA-A207 MHC class I molecules were recognized by C183. C183 recognized the HBc18-27 epitope with high sensitivity (≤1 pM) from all genotypes and the epitope was recognized almost equally when presented by the three most dominant HLA-A2 subtypes (A) A0201, (B) A0206 and (C) A0207.

Figure 12:
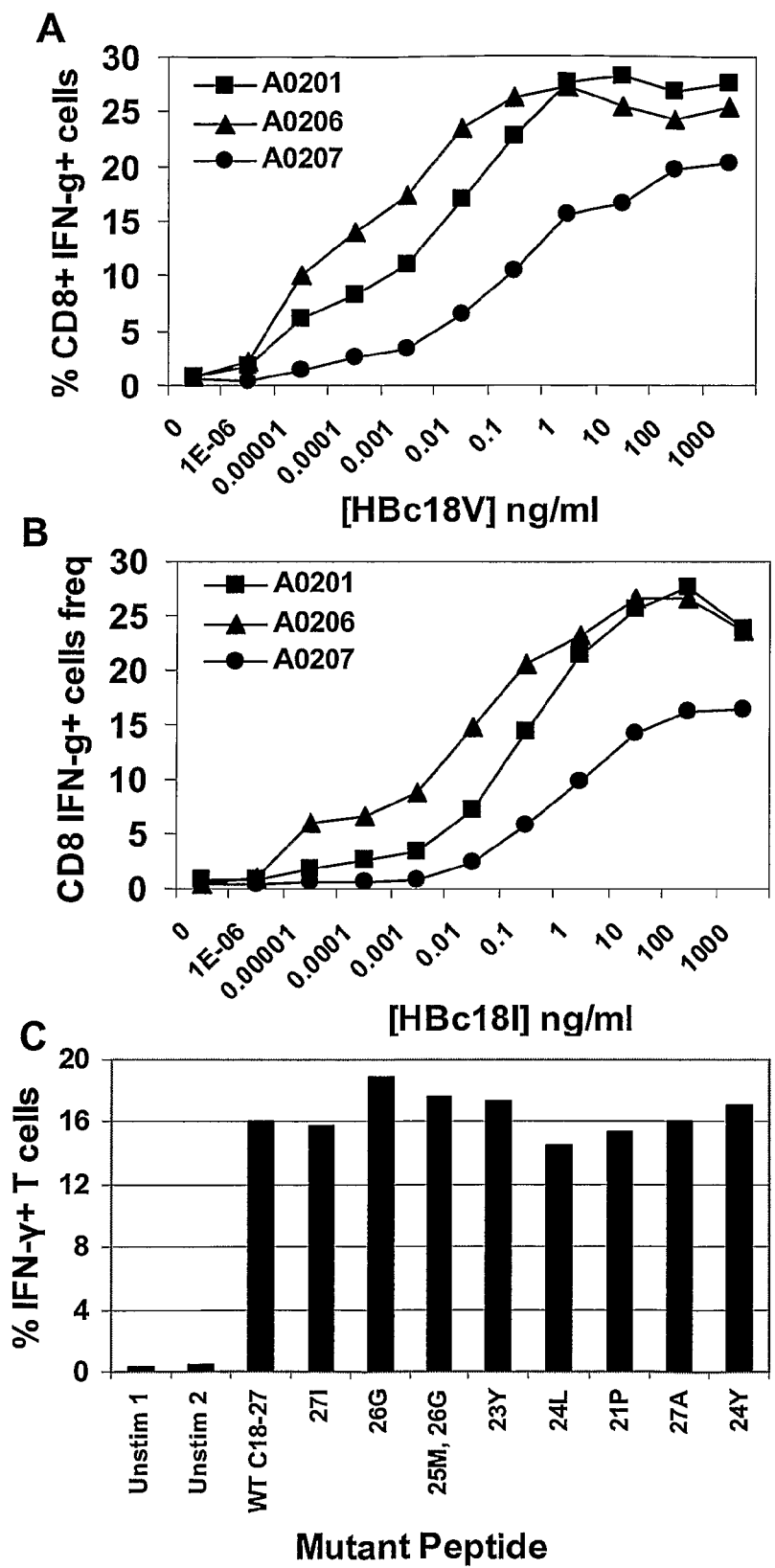
FIG. 12 (A) EBV transformed B cells expressing HLA-A0201, -A0206 or -A0207 subtypes were loaded with increasing concentrations of HBV genotype A/D HBc18-27 epitope (sequence provided in Table 1) and co-cultured with HBc-18-27 TCR transduced T cells for 5 h. T cell activation was measured by intracellular cytokine staining for IFN-γ. The results show that the HBc-18-27 TCR transduced T cells recognize the HBc18-27 eptiope presented by multiple HLA-A2 subtypes.

To further show that the HBc-18-27 TCR transduced T cells recognize the HBc18-27 eptiope presented by multiple HLA-A2 subtypes and various mutants of the HBc18-27 epitope, EBV transformed B cells expressing HLA-A0201, -A0206 or -A0207 subtypes were loaded with increasing concentrations of HBV genotype A/D HBc18-27 epitope (FIG. 12 (A)) and HBV genotype B/C HBc18-27 epitope, (FIG. 12 (B)) (sequence provided in Table 1) and co-cultured with HBc-18-27 TCR transduced T cells for 5 h. T cell activation was measured by intracellular cytokine staining for IFN-γ. The results as shown in FIGS. 12 (A) and (B) show that the HBc-18-27 TCR transduced T cells recognize the HBc18-27 eptiope presented by multiple HLA-A2 subtypes.

FIG. 12 (C) shows the results when HLA-A2+ T2 cells were loaded with each of the mutant peptides of HBc18-27 epitope and co-cultured with HBc-18-27 TCR transduced T cells for 5 h. T cell recognition of the mutant peptides was determined by intracellular cytokine staining for IFN-γ. The sequences of the mutant peptides are provided in Table 1. As can be seen from the results, the HBc-18-27 TCR transduced T cells recognized various mutants of the HBc18-27 epitope. The Unstim 1 and Unstim 2 refer to the control where the HLA-A2+ T2 cells were not loaded with any peptide.

Example 4

Isolation of C183 T Cell Receptor Alpha and Beta Chain DNA

Total RNA was isolated from $5×10^6$ C183 clones using TRIzol (Invitrogen). TCR alpha and beta chain cloning was performed on a contract basis by Primm SRL (Milano, Italy) and supplied in Topo blunt II cloning vector for downstream cloning.

The sequence analysis revealed the presence of one TCR beta chain, Vβ8.2, and one TCR alpha chain, Vα3 in C183. Further DNA sequence analysis using the Immunogenetics V-Quest algorithm (http://imgt.cines.fr/IMGT_vquest/share/textes/) identified 3 unique Complementarity Determining Region (CDR) in the Vα3 chain (CDR1α: SEQ ID NO:9, CDR2α: SEQ ID NO:10, CDR3α: SEQ ID NO:11) and the three unique CDR in the Vβ8.2 chain (CDR1β: SEQ ID NO:21, CDR2β: SEQ ID NO:22, CDR3β: SEQ ID NO:23).

Example 5

Retroviral Constructs Containing HBc18-27 Specific TCR (HBc18-27 TCR) and Lymphocyte Transduction TCR Vα3 and TCR Vβ8.2 cDNA prepared according to Example 4 above, were cloned individually into retroviral vector MP71 as described in Engels, Cam et al. 2003. (Kindly provided by Professor Hans Stauss, Royal Free and UCL Medical School, London, UK) using a 5' Not-1 site and 3' BsrG1 sites (New England Biolabs, Ipswich, Mass.). TCR Vα3, Vβ8.2 and MP71 vector were digested for 1 h at 37° C. with 10 U of each enzyme. Digested products were isolated on 1% agarose gel by electrophoresis and purified using Qiagen gel extraction kit. TCR chains and MP71 vector were mixed in 1:1 ratio and ligated overnight at 4° C. with T4 DNA ligase (Promega) to form retroviral constructs-MP71-TCR Vα3 and MP71-TCR Vβ8.2. These constructs were then sequenced to confirm DNA insert was correct.

To determine the expression and function of the cloned TCR, the constructs were used for preparation of retroviral supernatant which was further used for T cell transduction as explained below. Expression of inserted alpha and beta chains was driven by viral long terminal repeats (LTR) found in each construct.

Retroviral supernatants were prepared using a transient transfection method which comprised using Phoenix amphotropic packaging cell line (Clontech Laboratories, US) that was first plated at $2 \times 10^6$ cells/dish and allowed to adhere for 24 h in Iscove's Modified Dulbecco's Medium (IMDM), 10% FBS, 25 mM HEPES, Glutamax (Invitrogen) and 25 ug/ml Plasmocin (Invivogen). Cells were transiently co-transfected using the CaCl$_2$ method for 24 h with 9 μg each of MP71-TCR Vα3, MP71-TCR Vβ8.2 together with 6 μg of amphotropic envelope (kindly provided by Professor Hans Stauss, Royal Free and UCL Medical School, London, UK) IMDM was then replaced with Aim-V 2% human AB serum and phoenix cells were incubated for an additional 24 h before retroviral supernatants were collected for transduction.

Healthy donor and chronic HBV patient peripheral blood lymphocytes (PBL) were used to test expression and functionality of the cloned HBc18-27 TCR. Peripheral blood mononuclear cells (PBMC) were isolated from volunteers under informed consent by ficoll density gradient centrifugation. PBMC were stimulated with 600 U/ml interleukin-2 (IL-2; R&D Systems) and 50 ng/ml anti-CD3 (OKT-3; eBioscience, San Diego, Calif.) for 48 h. Untreated 24 well tissue culture plates were coated with 30 ug/ml Retronectin (Takara Bio, Otsu Shiga, Japan) overnight at 4° C. Wells were then washed with HBSS and blocked with PBS 2% BSA for 30 min. Lymphocytes were harvested, washed, counted and $5 \times 10^5$ cells plated into retronectin coated wells and mixed with the retroviral supernatants collected as described above. Mock transduced cells which were included as negative control, were cultured with the supernatant from Phoenix cells that were not transfected with retroviral vectors. IL-2 was added to wells to final concentration of 600 U/ml. The lymphocytes were incubated for 24 h in the retroviral supernatant, after which time the medium was replaced with Aim-V 2% human AB serum plus 100 U/ml IL-2. Transduced and mock transduced cells were grown for additional 3 days. After 3 days, the cell surface expression of the TCR was measured in both the TCR transduced and mock transduced cells by immunofluorescence staining. CD8-PE-Cy7 (BD Biosciences), Vβ8-PE expression (Beckman Coulter) and HLA-A201-HBc18-PE pentamer (Proimmune) staining were quantified by flow cytometry. Flow cytometry was performed on stained cells using a FACs Canto flow cytometer (BD Biosciences), and data were analyzed with the FACs Diva program (BD Biosciences).

As shown in FIG. 7A, expression of Vβ8 was significantly increased in HBc18-27 TCR transduced lymphocytes compared to mock transduced cells, which expressed only endogenous levels of Vβ8. Vβ8 expression was observed in both CD8+ and CD8- cells. To properly bind pentamer requires the cooperative interaction of a correctly paired, introduced alpha and beta chain as well as the co-receptor CD8. The CD8+ HBc18-27 TCR transduced T cells bound HBc18-27-HLA-A201 pentamers indicating that the Vα3 TCR chain was also expressed and the introduced TCR was correctly paired on the cell surface of transduced lymphocytes (FIG. 7B).

Figure 7:
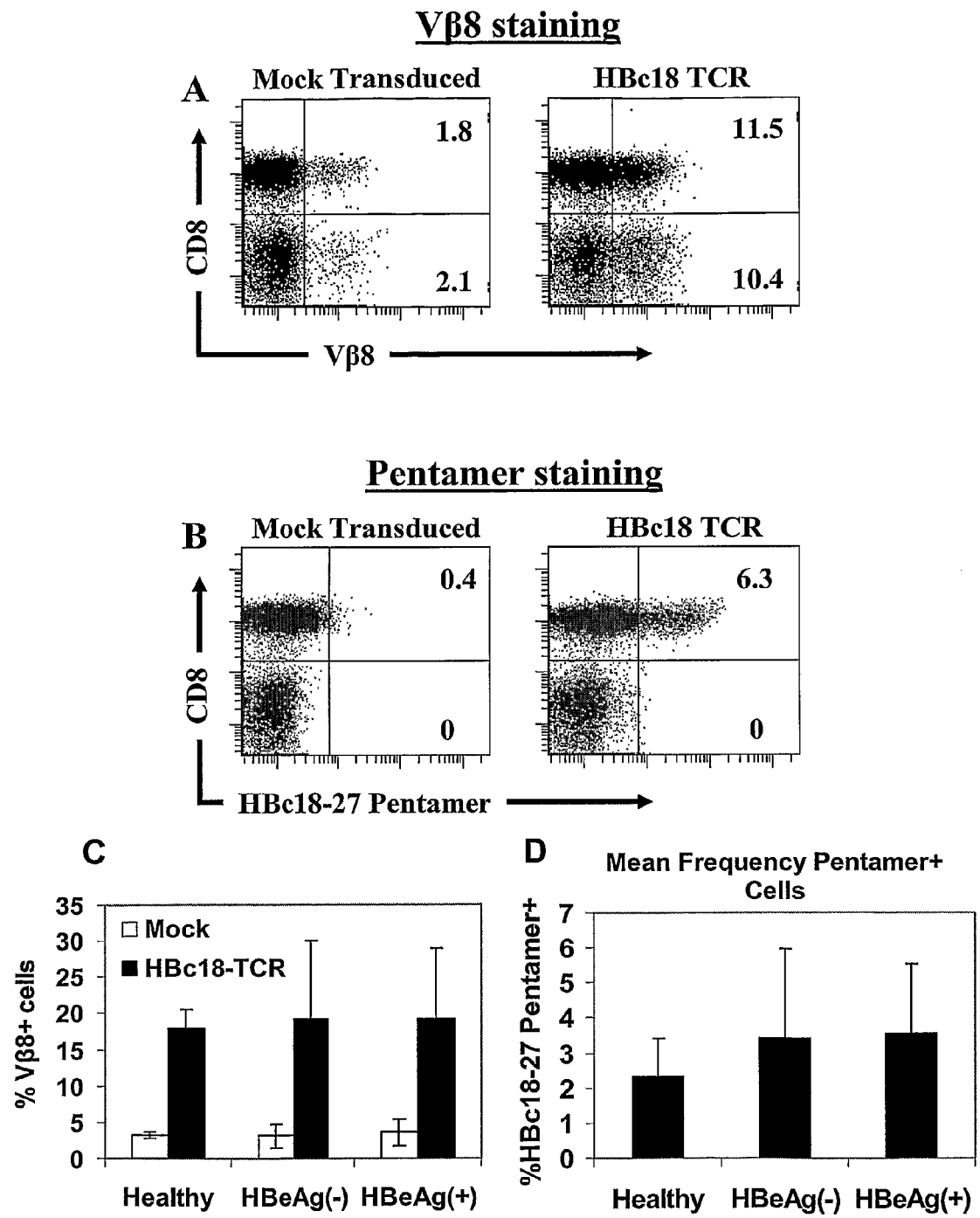
FIG. 7 shows the analysis of T Cell Receptor (TCR) transduction efficiency.

The HBc18-27 TCR transduction efficiency is confirmed in FIG. 7 (C) which show the mean frequency of Vβ8+ T cells from 5 healthy, 5 HBeAg+ chronic HBV patients (HBV DNA>$10^7$ copies/ml), and 5 HBeAg- chronic HBV patients (HBV DNA<$10^6$ copies/ml). FIG. 7 (D) which shows the mean frequency of HBc18-27-A201 specific pentamer+ T cells from 5 healthy, 5 HBeAg+ chronic HBV patients (HBV DNA>$10^7$ copies/ml), and 5 HBeAg- chronic HBV patients (HBV DNA<$10^6$ copies/ml) confirms that the transduced HBc18-27 TCR was correctly paired and bound HBc18-27-HLA-A201 pentamers. These data demonstrate that T cells from both healthy donors and chronic HBV patients could be transduced with the HBc18 TCR with similar efficiency.

Example 6

Function of HBc18-27 TCR Transduced T Cells

To confirm that the introduced HBc18-27 TCR was functional, HLA-A2 positive T2 cells (American Type Culture Collection (Rockford, Md.)) were used to stimulate HBc18-27 TCR transduced or mock transduced lymphocytes. T2 cells were cultured in RPMI 1640 supplemented with 10% heat-inactivated fetal bovine serum (FBS), 20 mM HEPES, 0.5 mM sodium pyruvate, 100 U/ml penicillin, 100 μg/ml streptomycin, MeM amino acids, Glutamax, MeM nonessential amino acids (Invitrogen Ltd) and 5 μg/ml Plasmocin (InvivoGen, San Diego, Calif.). The T2 cells were pulsed with 1 μg/ml HBc18-27 peptide for 1 hr and then washed to remove excess peptide.

In order to stimulate the HBc18-27 TCR transduced lymphocytes, referred to herein as HBc18-27 TCR transduced T cells, that were prepared according to Example 5, the HBc18-27 TCR transduced or mock transduced T cells were co-cultured overnight with the two different types of T2 cells (pulsed with HBc18-27 peptide and not pulsed) at 37° C. with 2 ug/ml brefeldin A. The HBc18-27 TCR transduced and mock transduced T cells were then washed and stained with anti-CD8-PE-Cy7 (BD Pharmingen, San Diego, Calif.) fixed and permeablized using cytofix/cytoperm (BD Biosciences) according to manufacturer's instructions. T cells were then stained for TNF-α-Alexa 488, IL-2-PE and IFN-γ-APC (BD Biosciences) for 30 min on ice. Cells were washed and analyzed by flow cytometry using FACs Canto flow cytometer (BD Biosciences), and data were analyzed with the FACs Diva program (BD Biosciences).

The results are shown in FIG. 8A. The mock transduced T cells failed to produce any cytokines (i.e. IFN-γ, TNF-α or IL-2) in the presence or absence of HBc18-27 epitope. HBc18-27 TCR transduced T cells did not respond to T2 cells in the absence of peptide (FIG. 8A, row 1) but produced IFN-γ, TNF-α and IL-2 in response to HBc18-27 peptide loaded T2 cells (FIG. 8A, row 3) indicating that the introduced HBc18-27 TCR was functional when expressed in primary T cells. Furthermore, the introduced HBc18-27 TCR was functional in CD8- cells (CD4+ cells) as well as CD8+, expanding its potential usefulness for immunotherapy because CD4+ T cells provide additional IL-2 to maintain T cell survival and co-stimulatory ligands such as CD40L, which has the potential to boost B cell responses.

Figure 8:
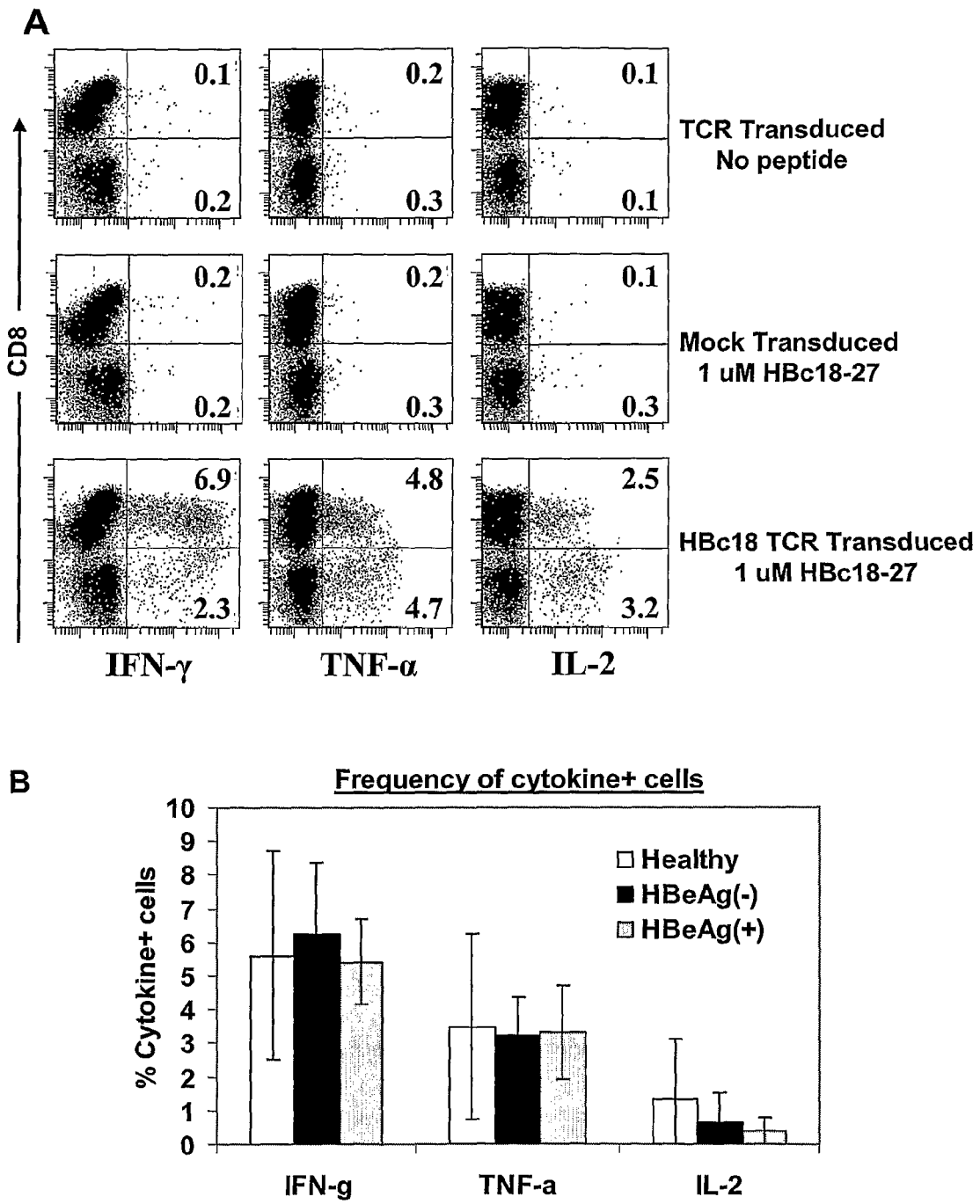
FIG. 8 (A) shows the FACS analysis of T cells transduced with HBc18-27 A201 TCR to confirm that the introduced HBc18-27 TCR was functional. HBc18-27 TCR transduced or mock transduced T cells were co-cultured overnight with HLA-A2+ T2 cells which were first pulsed with HBc18-27 peptide ("peptide") and incubated for 5 h. The function of the T cells was then assessed by intracellular cytokine staining for IFN-γ (left column), TNF-α (middle column) and IL-2 (right column). In the absence of peptide, HBc18-27 TCR transduced cells were not activated (top row). Mock transduced cells were not activated by peptide pulsed T2 cells (middle row). HBc18-27 TCR transduced cells were stimulated to produce IFN-γ, TNF-α, and IL-2 following co-culture with peptide pulsed T2 cells (bottom row). Both CD8+ and CD8− (CD4+ T cells) were capable of producing all three cytokines confirming function of the introduced TCR in CD4+ T cells and multifunctional capacity of TCR re-directed cells.

FIG. 8 (B) shows that HBc18-27 TCR transduced T cells from chronic HBV patients are equally functional to transduced T cells from healthy donors. Mean frequency of IFN-γ, TNF-α and IL-2 positive cells, as seen in FIG. 8A, from 5 healthy, 5 HBeAg+ chronic HBV patients (HBV DNA>$10^7$ copies/ml), and 5 HBeAg− chronic HBV patients (HBV DNA<$10^6$ copies/ml) are shown. The results show that T cells transduced with HBc18-27-A201 TCR become multifunctional with similar frequencies of cytokine positive cells in each patient group.

Example 7

Affinity of HBc18-27 TCR Transduced T Cells

Figure 9:
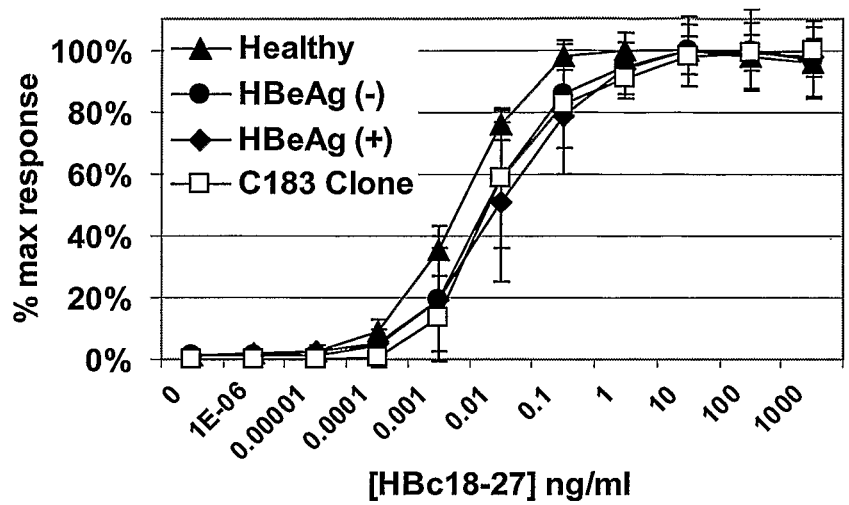
FIG. 9 shows the affinity of HBc18-27 TCR transduced T cells from healthy and chronic HBV patients compared to original C183 T cell clone.
Figure 9:
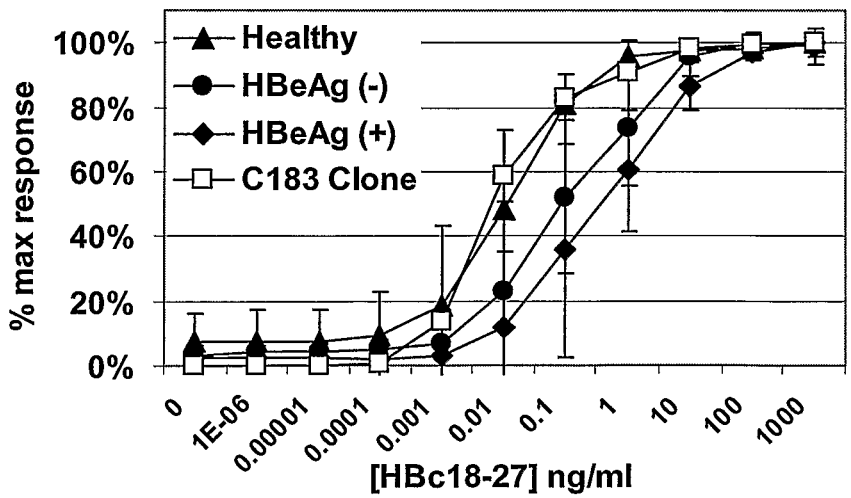

Due to the possible decreased level of expression of the introduced HBc18-27 TCR, it was possible that the engineered T cells may have a lower affinity for the actual viral epitope compared to the original T cell clone, C183. To test this hypothesis, HLA-A2 positive T2 cells (American Type Culture Collection, Rockford, Md.) were pulsed with HBc18-27 peptide at concentrations ranging from 1 fg/ml to 1 μg/ml according to the protocol described in Example 6. Peptide loaded T2 cells were co-cultured with HBc18-27 TCR transduced T cells from 5 healthy donors, 5 HBeAg+ chronic HBV patients (HBV DNA>$10^7$ copies/ml), and 5 HBeAg− chronic HBV patients (HBV DNA<$10^6$ copies/ml) and the original T cell clone C183 for 5 h. T cell activation was measured by intracellular cytokine staining for IFN-γ. Results are displayed at percent of maximum IFN-γ response because the frequency of HBc18-27 TCR transduced cells varied among patients while C183 was always 100% specific for the HBc18-27 epitope. The results showed that CD8+ HBc18-27 TCR transduced T cells displayed an affinity identical to C183 down to 1 pg/ml (FIG. 9A).

The affinity of HBc18-27 TCR transduced CD4+ T cells was determined in the same assay. CD8− HBc18-27 specific cells were considered CD4+ T cells because they were capable of responding to the HBc18-27 epitope in an antigen specific, dose dependent fashion. CD4+ HBc18-27 TCR transduced T cells showed slightly lower affinity compared to C183. The difference in the affinity to the viral epitope between CD8+ and CD4+ T cells may likely be due to CD8+ co-receptor binding, which stabilizes TCR interaction with the HLA-A2 molecule. The CD8+ co-receptor is absent on CD4+ T cells and therefore affinity is slightly reduced but still highly sensitive.

Example 8

Codon Optimization of HBc18-27 TCR DNA Sequence

Due to the presence of redundancy in the genetic code, most amino acids can be coded for by multiple codons, which are used with different frequencies and efficiencies within organisms and can actually result in less efficient translation of proteins. Due to genetic variation and the recombination events that occur during T cell development, DNA encoding for the HBc18-27 TCR may be comprised of codons that are not optimally translated within humans. Therefore, codon optimization for both the Vβ8.2 and Vα3 chains of the HBc18-TCR was done to result in a more efficient expression of HBc18-27 TCR and increased sensitivity and function (Service by Genscript, Piscataway, N.J.).

Codon optimized Vα3 and Vβ8.2 were cloned individually into MP71 vector using 5'Not-1 and 3'BsrG1 restriction enzyme sites as described above. In order to confirm that the codon optimized TCR, referred to herein as HBc18-Opt-TCR, was still capable of being expressed, PBL were transduced with the HBc18-Opt-Vα3 and HBc18-Opt-Vβ8.2 TCR constructs as described above. For the HBc18-27 wild type TCR, referred to herein as HBc18-WT-TCR, PBL were also transduced with the HBc18-WT-Vβ8.2 (MP71-TCR Vβ38.2 from example 7) and HBc18-WT-Vα3 (MP71-TCR Vα3 from example 7) for comparison. HBc18-27 transduced PBL were analyzed for Vβ8 expression and the ability to bind HBc18-HLA-A201 pentamers (Proimmune, Oxford, United Kingdom) by flow cytometry 3 days after transduction. Results showed that the frequency of Vβ8+ T cells was similar between PBL transduced with HBc18-Opt-TCR (21.5%) compared to HBc18-WT-TCR (21.1%) transduced cells (FIG. 10A)

Figure 10:
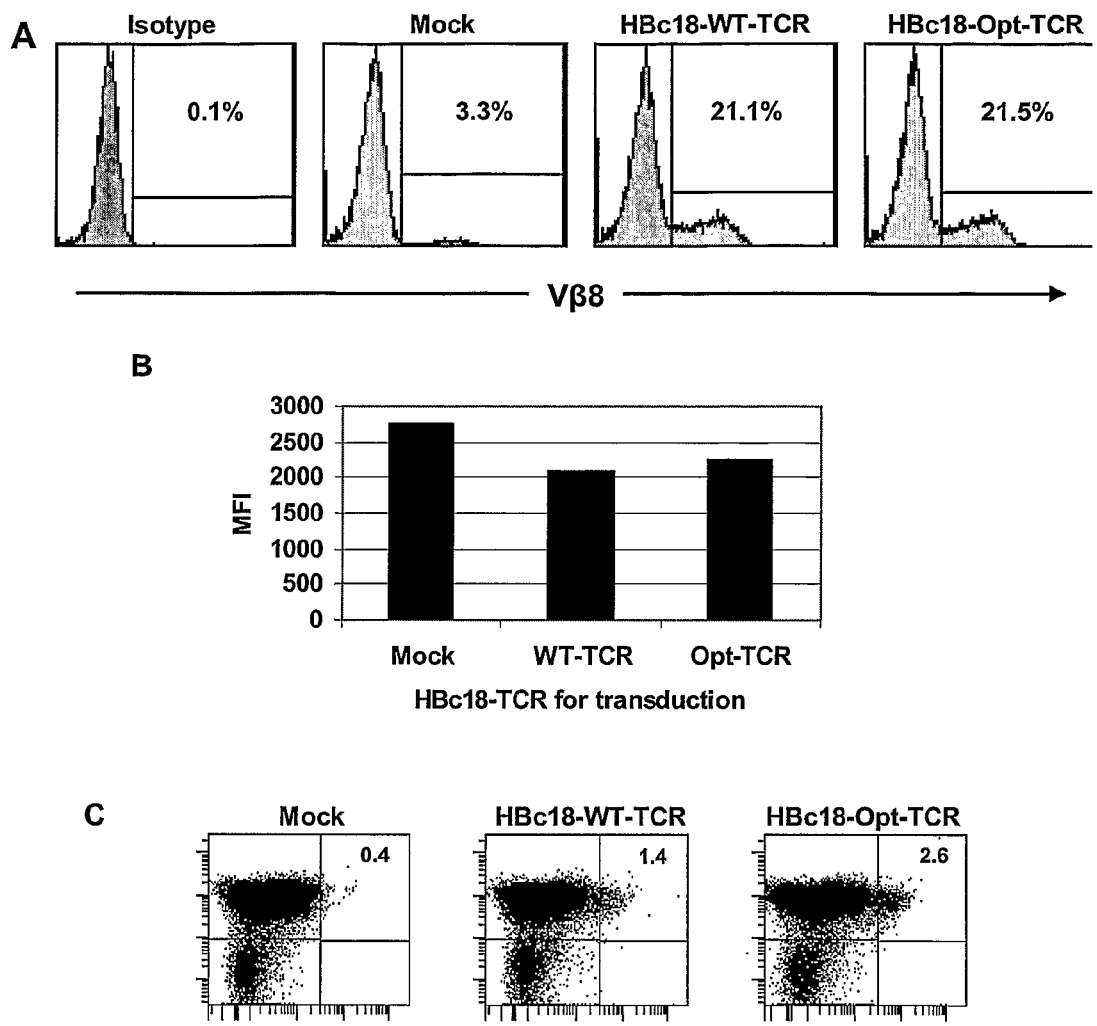
FIG. 10 shows the expression of optimized HBc18-Opt-TCR compared to the wild type HBc18-WT-TCR.

The amount of Vβ8 expressed in the HBc18-Opt-TCR transduced lymphocytes and HBc18-WT-TCR transduced lymphocytes was measured by mean fluorescence intensity (MFI) using the FACs Diva software (BD Biosciences) (FIG. 10B). Isotype values were subtracted to determine specific MFI. The results showed that the amount of Vβ8 expressed was almost identical in both the HBc18-Opt-TCR transduced lymphocytes and HBc18-WT-TCR transduced lymphocytes (FIG. 10B).

To determine the ability to bind HBc18-HLA-A201 pentamers, the HBc18-Opt-TCR transduced lymphocytes and HBc18-WT-TCR transduced lymphocytes were labelled with anti-CD8-PE-Cy7 (BD Pharmingen, San Diego, Calif.) and HBc18-HLA-A201 pentamers (Proimmune, Oxford, United Kingdom). The percentages of stained lymphocytes were determined by Fluorescence-activated cell sorting (FACS) analysis using a FACs Canto flow cytometer (BD Biosciences, SanDiego, Calif.) and analyzed using FACs Diva software (BD Biosciences). The results showed that the frequency of HBc18-HLA-A201 pentamer positive cells was two fold higher in cells transduced with HBc18-Opt-TCR than the HBc18-WT-TCR (FIG. 10C), suggesting that the Vα3 chain may be expressed more efficiently from the codon optimized construct compared to the wild type sequence. Because Vβ8 staining was equivalent in FIG. 10A increased pentamer binding is likely related to better expression of the Vα3 chain to increase expression of correctly paired HBc18-27 TCR on the cell surface.

Following confirmation that the HBc18-Opt-TCR was properly expressed in the transduced T cells, we tested functionality of the HBc18-Opt-TCR compared to the HBc18-WT-TCR. HBc18-Opt-TCR and HBc18-WT-TCR or mock transduced T cells were stimulated overnight with HLA-A2 positive T2 cells in the presence or absence of HBc18-27 peptide plus 2 μg/ml brefeldin A according to the protocol described in Example 6. T cells were then labelled with anti-CD8 PE-Cy7 (BD Pharmingen, San Diego, Calif.) and fixed and permeablized using cytofix/cytoperm according to manufacturer's instructions (BD Biosciences). Cells were then stained with anti-IFN-γ-APC (BD Biosciences) for 30 min on ice and T cell IFN-γ production was analyzed by flow cytometry.

Figure 11:
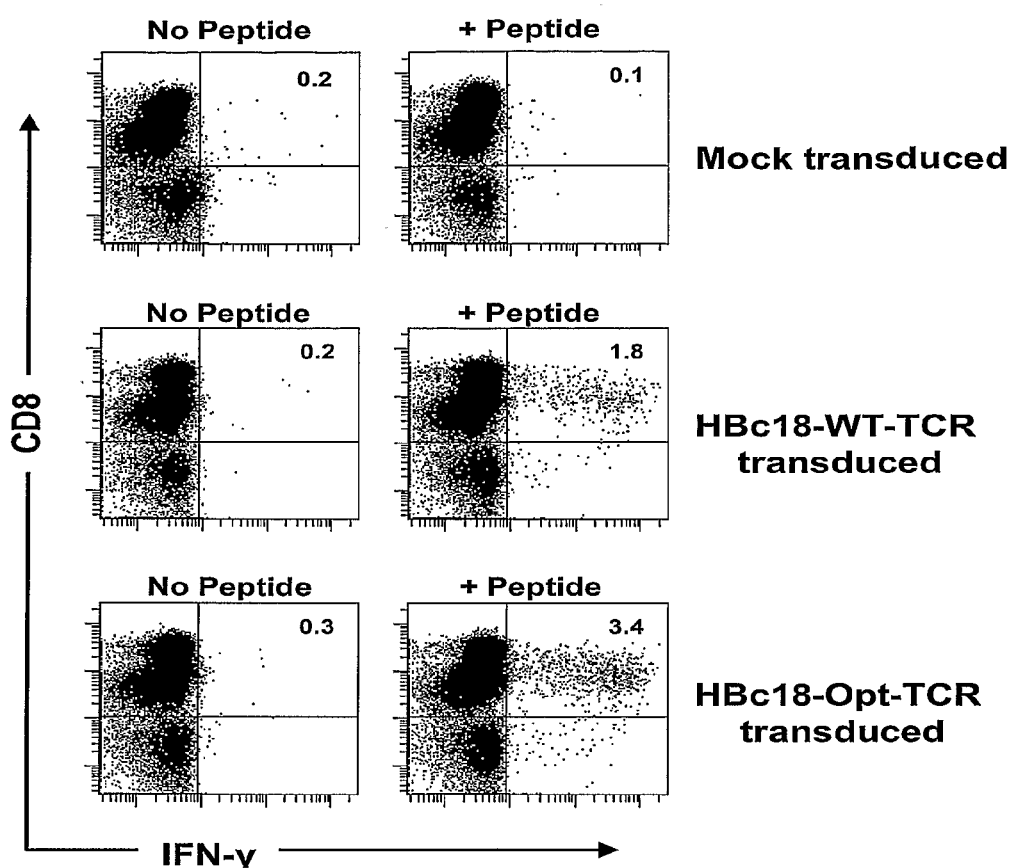
FIG. 11 shows that there is an increased frequency of IFN-γ positive cells in T cells transduced with HBc18-Opt-TCR compared to HBc18-WT-TCR constructs. Mock transduced T cells, HBc18-WT-TCR and HBc18-Opt-TCR were stimulated overnight with HLA-A2 positive T2 cells which were initially pulsed or not pulsed with HBc18-27 peptide, in the presence of 2 μg/ml brefeldin A. T cells were then labelled with anti-CD8 PE-Cy7 and stained for IFN-γ by intracellular cytokine staining. The results demonstrated that there was nearly a two fold increase in the frequency of IFN-γ positive T cells transduced with the HBc18-Opt-TCR compared to T cells transduced with the HBc18-WT-TCR. The increase in pentamer positive cells correlated with an increase in functional cells able to respond to peptide loaded target T cells.

The results show that there was nearly a two fold increase in the frequency of IFN-γ positive T cells transduced with the HBc18-Opt-TCR compared to T cells transduced with the HBc18-WT-TCR (FIG. 11). Mock transduced cells were negative in the presence of absence of HBc18-27 peptide.

Therefore, the increase in pentamer positive cells correlated with an increase in functional cells able to respond to peptide loaded targets.

Example 9

Figure 13:
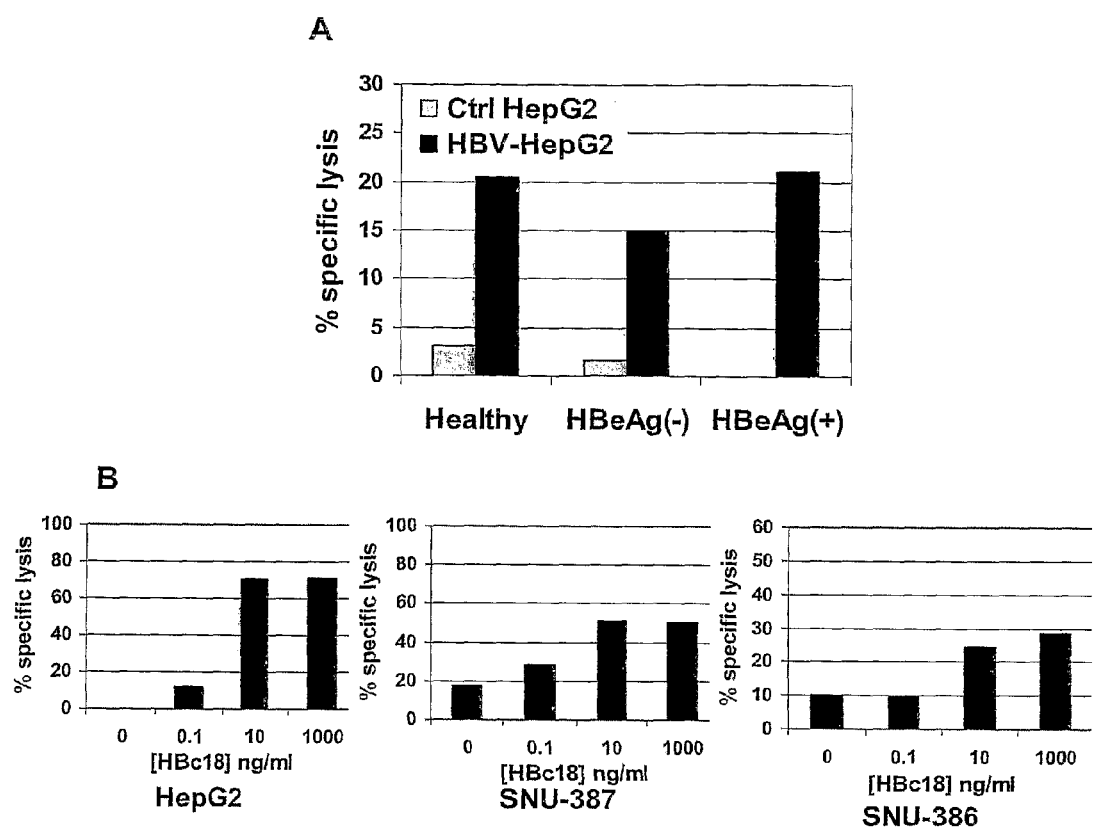
FIG. 13 (A) TCR transduced T cells from each patient group (healthy, HBeAg(–), HBeAg(+)) were co-cultured with DiOC labeled HepG2 cells expressing the entire HBV genome (HBV-HepG2) or the parental control cell line (Ctrl-HepG2) at Effector:Target ratio of 1:1 for 6 h in the presence of Propidium Iodide (PI). Dying target cells were DiOC+/PI+. Results are representative of 3 experiments. Effector T cells were considered to be IFN-γ+/CD8+ cells determined by intracellular cytokine staining after stimulation with peptide pulsed T2 cells. The results showed that HBc18-27 TCR transduced T cells can kill HCC cell lines which endogenously express HBV proteins or are loaded with the HBV 18-27 peptide.

HBc18-27 TCR Transduced T Cells Kill HCC Cell Lines Which Endogenously Express HBV Proteins or are Loaded with the HBV 18-27 Peptide HBc18-27 TCR transduced T cells from each patient group (healthy, HBeAg(−), HBeAg(+)) were co-cultured with DiOC labeled HepG2 cells expressing the entire HBV genome (HBV-HepG2) or the parental control cell line (Ctrl-HepG2) at Effector:Target ratio of 1:1 for 6 h in the presence of Propidium Iodide (PI). Dying target cells were DiOC+/PI+. T cells were excluded from the analysis by staining with anti-CD11a-APC (BD Bioscience). Results are representative of 3 experiments. Effector T cells were considered to be IFN-γ+/CD8+ cells determined by intracellular cytokine staining after stimulation with peptide pulsed T2 cells. The results as shown in FIG. 13 (A) show that HBc18-27 TCR transduced T cells from healthy donors or chronic HBV patients can kill HCC cell lines which endogenously express HBV proteins. This suggests that HBc18 TCR transduced T cells could recognize tumor cells from patients expressing the HBV core antigen.

To determine if TCR transduced T cells could kill multiple HLA-A2+ HCC cell lines, DiOC labeled HCC cell lines (HepG2 were obtained from ATCC; SNU-387, SNU-368 were obtained from the Korean cell line bank) were loaded with increasing concentrations of HBc18-27 peptides and co-cultured with HBc-18-27 TCR transduced T cells at Effector to target ratio of 1:1 for 6 h in the presence of Propidium Iodide (PI). Dying target cells were DiOC+/PI+. T cells were excluded from the analysis by staining with anti-CD11a-APC (BD Bioscience). Results are representative of 3 experiments. Effector T cells were considered to be IFN-γ+/CD8+ cells determined by intracellular cytokine staining after stimulation with peptide pulsed T2 cells. The results as shown in FIG. 13 (B) showed that HBc18-27 TCR transduced T cells are able to kill multiple HLA-A2+ HCC cell lines.

Example 10

Cloning Hepatitis B Virus Specific T Cell Specific for HBV Envelope 370-79 Eptitope (HBs370-79)

Peripheral blood lymphocytes (PBL) were isolated and prepared according to the method of Example 1 and stimulated with 1 μM of HBV envelope 370-79 epitope ("HBs370-79 peptide"; SIVSPFIPLL; SEQ ID NO: 56; Primm SRL, Milano, Italy) plus 20 U/ml interleukin-2-(R&D systems, Minneapolis, Minn.) and plated in a 24-well plate at $4 \times 10^6$ cells/well for 10 days.

The HBs370-79-specific CD8+ T cells were enriched using IFN-γ capture assay according to manufacturer's instructions. (Miltenyi Biotech, Surrey, United Kingdom).

The IFN-γ+HBs370-79− specific T cells were then cloned using the limiting dilution assay as described in "Current Protocols in Immunology" Copyright © 2007 by John Wiley and Sons, Inc., and expanded in Aim-V 2% AB serum (Invitrogen, Carlsbad, Calif.), 20 U/ml IL-2, 10 ng/ml IL-7, and 10 ng/ml IL-15 (R&D systems, Minneapolis, Minn.) with 1.5 μg/ml phytohemagglutinin (Sigma-Aldrich, Dorset, United Kingdom) using allogeneic irradiated PBL as feeder cells. Cells were plated at 1 cell/well on 96 well plates and wells positive for T cell growth were tested for HBs370-79 reactivity by intracellular cytokine staining for IFN-γ according to the protocol provided in Gehring et al. incorporated herein by reference. T cell clone, referred to herein as E10-1D was selected for further study.

E10-1D HBs370-79 specific cytotoxic T cell clone was grown and maintained in Aim-V, 2% AB serum, 20 U/ml IL-2, 10 ng/ml IL-7, and 10 ng/ml IL-15 (R&D Systems, Abingdon, United Kingdom) in a 5% $CO_2$ humidified incubator at 37° C.

Example 11

Figure 14:
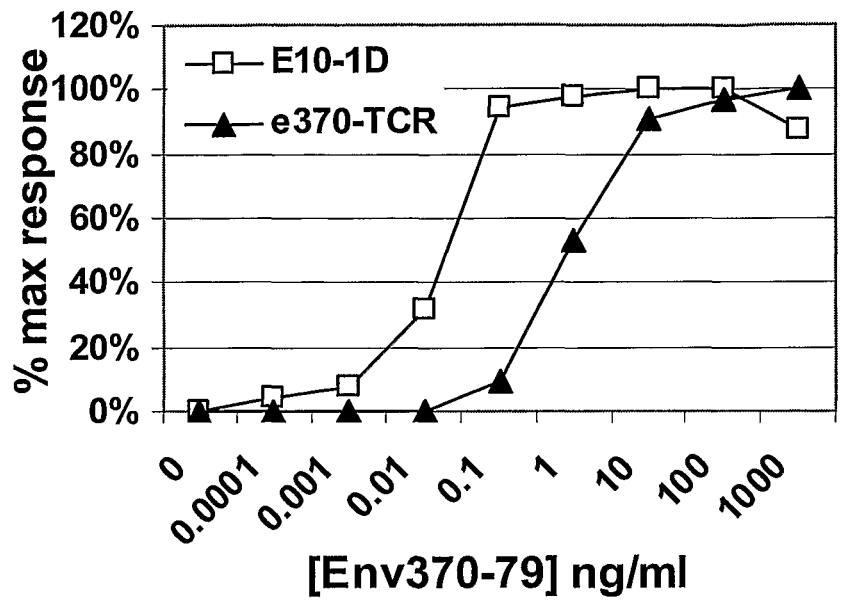
FIG. 14 (A) shows that the E10-1D T cell clone or HBs370-79 TCR transduced T cells, recognize HBs370-79 epitope loaded HLA-A2+ T2 cells. E10-1D T cell clone is made according to the method provided in Example 10. T2 cells were loaded with increasing concentrations of HBs370-79 peptide and co-cultured with E10-1D or HBs370-79 TCR transduced T cells for 5 h and stained for IFN-γ. Data presented as percent maximum response to normalize differing frequency of each line. The results show that HBs370-79 specific TCR is functional.
Figure 14:
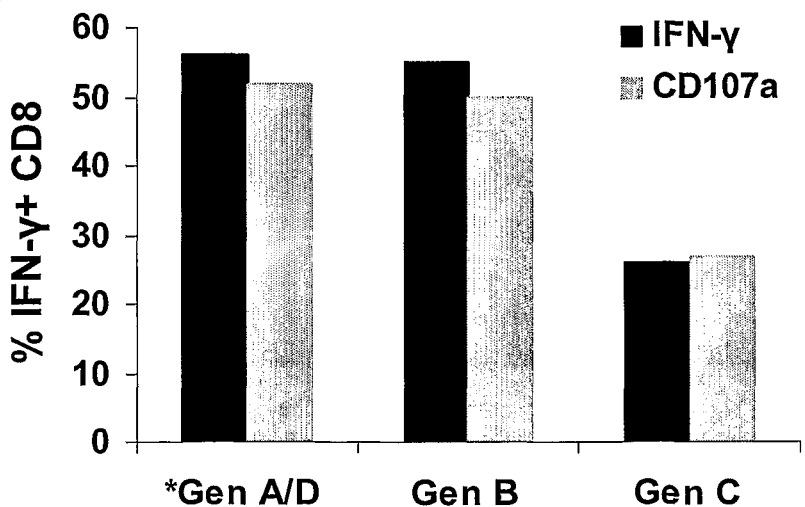

Affinity and Function of HBs370-79 Specific TCR Transduced T Cells and Recognition of Genotype Variant Peptides Experiments similar to that described in Example 6 were carried out with HBs370-79 specific TCR transduced T cells. The E10-1D T cell clone or HBs370-79 TCR transduced T cells, recognize HBs370-79 epitope loaded HLA-A2+ T2 cells. T2 cells were loaded with increasing concentrations of HBs370-79 peptide and co-cultured with E10-1D or HBs370-79 TCR transduced T cells for 5 h and stained for IFN-γ. Data presented as percent maximum response to normalize differing frequency of each line. The results as shown in FIG. 14 (A) show that HBs370-79 specific TCR is functional but that HBs370 TCR transduced T cells were lower affinity than the original T cell clone E10-1D.

Experiments similar to that described in Example 3 were also carried out with HBs370-79 specific TCR transduced T cells. HBs370-79 TCR transduced T cells recognize genotypic variants of the HBs370-79 epitope (The sequences of the genotypic variants are provided in Table 2). HBs370-79 TCR transduced T cells were co-cultured with HLA-A2+ T2 cells loaded with 1 μg/ml peptide of each genotype for 5 h and activation was assessed by CD107a labeling and staining for IFN-γ. Genotype A & D sequences are identical. The results as shown in FIG. 14 (B) show that HBs370-79 specific TCR recognizes genotypic variants of the HBs370-79 epitope.

REFERENCES

Engels, B., H. Cam, et al. (2003). "Retroviral vectors for high-level transgene expression in T lymphocytes." Hum Gene Ther 14(12): 1155-68.

Gehring A. J et al. (2007). The Level of Viral Antigen Presented by Hepatocytes Influences CD8 T-Cell Function. J Virol.; 81(6): 2940-2949.

Karlin S. and Altschul S. F, (1990). Methods for assessing the statistical significance of molecular sequence features by using general scoring schemes. Proc Natl Acad Sci USA.; 87(6): 2264-2268.

Maini, M. and Bertoletti A (2006) "The effect of pathogens on the immune system: Viral hepatitis". In immunodominance: The choice of the Immune System, J. A. Frelinger, ed (Weinheim: Wiley-VCH).

Molecular Cloning: A Laboratory Manual, 3d ed., Sambrook and Russell, CSHL Press (2001).

Schumacher et. al., (2002), Nat Rev. Immunol, Vol 2: 512.

Strain, A. J., et al. 1991. Native and recombinant human hepatocyte growth factors are highly potent promoters of DNA synthesis in both human and rat hepatocytes. J Clin Invest 87:1853-7.

Sun, D. and M. Nassal (2006). "Stable HepG2- and Huh7-based human hepatoma cell lines for efficient regulated expression of infectious hepatitis B virus." J Hepatol 45(5): 636-45.

The invention claimed is:

1. An isolated T-cell comprising at least one exogenous, HLA-A2-restricted T-cell receptor that recognizes a hepatitis B virus (HBV) core antigen or a mutant thereof comprising an HBc18-27 epitope that has the amino acid sequence of SEQ ID NO: 25 or SEQ ID NO: 26.

2. The isolated T-cell of claim 1, wherein the T-cell receptor comprises: i) a Vα3 chain comprising the amino acid sequence of SEQ ID NO: 9, SEQ ID NO: 10 or SEQ ID NO: 11, or ii) a Vβ8 chain comprising the amino acid sequence of SEQ ID NO: 21, SEQ ID NO: 22, or SEQ ID NO: 23.

3. The isolated T-cell of claim 1, wherein the T-cell receptor comprises a Vα3 chain having at least 90% amino acid identity to SEQ ID NO: 12 and a Vβ8 chain having at least 90% amino acid identity to SEQ ID NO: 24.

* * * * *